US011179412B2

(12) United States Patent
Tang et al.

(10) Patent No.: US 11,179,412 B2
(45) Date of Patent: Nov. 23, 2021

(54) METHODS OF TREATING CONDITIONS INVOLVING ELEVATED INFLAMMATORY RESPONSE

(71) Applicant: University of Pittsburgh—Of the Commonwealth System of Higher Education, Pittsburgh, PA (US)

(72) Inventors: Daolin Tang, Dallas, TX (US); Timothy Billiar, Presto, PA (US); Ling Zeng, Chongqing (CN)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 16/209,206

(22) Filed: Dec. 4, 2018

(65) Prior Publication Data

US 2019/0167710 A1 Jun. 6, 2019

Related U.S. Application Data

(60) Provisional application No. 62/594,162, filed on Dec. 4, 2017, provisional application No. 62/608,835, filed on Dec. 21, 2017.

(51) Int. Cl.

| | |
|---|---|
| ***A61K 48/00*** | (2006.01) |
| ***C07H 21/04*** | (2006.01) |
| ***A61K 31/7105*** | (2006.01) |
| ***A61K 31/439*** | (2006.01) |
| ***A61K 31/506*** | (2006.01) |
| ***A61P 37/06*** | (2006.01) |
| ***A61K 31/675*** | (2006.01) |
| ***C12N 15/113*** | (2010.01) |

(52) U.S. Cl.

CPC ........ *A61K 31/7105* (2013.01); *A61K 31/439* (2013.01); *A61K 31/506* (2013.01); *A61K 31/675* (2013.01); *A61P 37/06* (2018.01); *C12N 15/113* (2013.01); *C12N 15/1136* (2013.01); *C12N 2310/14* (2013.01); *C12N 2320/30* (2013.01)

(58) Field of Classification Search

CPC .. A61K 31/713; C07K 16/40; C12N 2310/14; C12N 15/113

See application file for complete search history.

(56) References Cited

U.S. PATENT DOCUMENTS

| | | | | |
|---|---|---|---|---|
| 5,032,401 | A | 7/1991 | Jamas et al. | |
| 5,607,677 | A | 3/1997 | Jamas et al. | |
| 8,101,348 | B2 | 1/2012 | Tuschl et al. | |
| 8,680,111 | B2 | 3/2014 | Bailey et al. | |
| 2004/0048795 | A1* | 3/2004 | Ivanova .................. | A61P 25/04 424/85.1 |
| 2005/0281781 | A1 | 12/2005 | Ostroff | |
| 2014/0186915 | A1* | 7/2014 | Mori .................... | C12N 9/0077 435/167 |
| 2015/0197525 | A1* | 7/2015 | Silverman ............ | A61K 31/454 514/171 |
| 2017/0081667 | A1 | 3/2017 | Chen et al. | |
| 2017/0281624 | A1 | 10/2017 | Peters et al. | |
| 2017/0304315 | A1* | 10/2017 | Haudenschild ......... | A61P 19/02 |
| 2018/0235933 | A1 | 8/2018 | Pencheva et al. | |
| 2018/0258040 | A1* | 9/2018 | Hatcher ................... | C12N 9/12 |

FOREIGN PATENT DOCUMENTS

| | | | |
|---|---|---|---|
| WO | 2008073687 | A2 | 6/2008 |
| WO | 2013132376 | A1 | 9/2013 |
| WO | 2014207606 | A1 | 12/2014 |
| WO | 2016209862 | A1 | 12/2016 |
| WO | 2017175091 | A1 | 10/2017 |

OTHER PUBLICATIONS

Ono et al. (Lung Cancer, 99, 2016, 151-154).*
Remington: The Science and Practice of Pharmacy, 21st Edition, ed. Lippincott, Williams & Wilkins, Baltimore, MD Easton, PA., 2005, Chapters 37, 39, 41, 42 and 45.
Rhodes et al., "Cell-free DNA and outcome in sepsis", Critical Care, 2012, pp. 1-2, vol. 16:170.
Rittirsch et al., "Immunodesign of experimental sepsis by cecal ligation and puncture", Nature Protocols, 2009, pp. 31-36, vol. 4:1.
Roskoski Jr., "Anaplastic lymphoma kinase (ALK): Structure, oncogenic activation, and pharmacological inhibition", Pharmacological Research, 2013, pp. 68-94, vol. 68.
Saukkonen et al., "Cell-Free Plasma DNA as a Predictor of Outcome in Severe Sepsis and Septic Shock", Clinical Chemistry, 2008, pp. 1000-1007, vol. 54:6.
Savan et al., "A novel role for IL-22R1 as a driver of inflammation", Blood, 2011, pp. 575-584, vol. 117:2.
Seo et al., "Akt Kinase-Mediated Checkpoint of cGAS DNA Sensing Pathway", Cell Reports, 2015, pp. 1-10, vol. 13.
Sharma et al., "Triggering the Interferon Antiviral Response Through an IKK-Related Pathway", Science, 2003, pp. 1148-1151, vol. 300.
Singer et al., "The Third International Consensus Definitions for Sepsis and Septic Shock (Sepsis-3)", JAMA, 2016, pp. 801-810, vol. 315:8.
Sirois et al., "RAGE is a nuleic acid receptor that promotes inflammatory responses to DNA", The Journal of Experimental Medicine, 2013, pp. 2447-2463, vol. 210:11.

(Continued)

*Primary Examiner* — Amy H Bowman
(74) *Attorney, Agent, or Firm* — The Webb Law Firm

(57) ABSTRACT

A method of treating a patient having an elevated inflammatory response, such as an elevated Type I interferon response, is provided. The method can be used to treat sepsis. The method comprises administering to a patient having an elevated inflammatory response, an inhibitor of anaplastic lymphoma kinase (ALK inhibitors) or expression of ALK, in an amount effective to treat the elevated inflammatory response.

10 Claims, 42 Drawing Sheets
(18 of 42 Drawing Sheet(s) Filed in Color)
Specification includes a Sequence Listing.

(56) References Cited

OTHER PUBLICATIONS

Sun et al., "Cyclic GMP-AMP Synthase is a Cytosolic DNA Sensor That Activates the Type I Interferon Pathway", Sciencexpress, 2012, pp. 786-791.
Surbatovic et al., "Cytokine Profile in Severe Gram-Positive and Gram-Negative Abdominal Sepsis", Scientific Reports, 2015, pp. 1-12.
Tanaka et al., "Sting Specifies IRF3 Phosphorylation by TBK1 in the Cytosolic DNA Signaling Pathway", Immunology, 2012, pp. 1-12, vol. 5:214.
Tang et al., "Endogenous HMGB1 regulates autophagy", J. Cell Biol., 2010, pp. 881-892, vol. 190:5.
Ulloa et al., "The 'cytokin profile': a code for sepsis", Trends in Molecular Medicine, 2005, pp. 1471-4914, vol. 11:2.
Vernersson et al., "Characterization of the expression of the ALK receptor tyrosine kinase in mice", Gene Expression Patterns, 2006, pp. 448-461, vol. 6.
Vincent et al., "Sepsis definitions: time for change", Lancet, 2013, pp. 774-775, vol. 381.
Wang et al., "Targeting HMGB1 in the treatment of sepsis", Expert Opin. Ther. Targets, 2014, pp. 257-268, vol. 18:3.
Wang et al., "S6K-STING interaction regulates cytosolic DNA-mediated activation of the transcription factor IRF3", Nature Immunology, 2016, pp. 514-522.
Wang et al., "STING Requires the Adaptor TRIF to Trigger Innate Immune Responses to Microbial Infection", Cell Host & Microbe, 2016, pp. 329-341, vol. 20.
Watts et al., "Silencing disease genes in the laboratory and the clinic", J Pathol, 2012, pp. 365-379, vol. 226.
Weber et al., "Interleukin-3 amplifies acute inflammation and is a potential therapeutic target in sepsis", Science, 2015, pp. 1260-1265, vol. 347:6227.
Weiss et al., "Anaplastic Lymphoma Kinase and Leukocyte Tyrosine Kinase: Functions and genetic interactions in learning, memory and adult neurogenesis" Pharmacology, Biochemistry and Behavior, 2012, pp. 566-574, vol. 100.
Woodward et al., "c-di-AMP Secreted by Intracellular Listeria monocytogenes Activates a Host Type I Interferon Response", Science, 2010, pp. 1703-1705, vol. 328.
Wu et al., "Cyclic GMP-AMP is an Endogenous Second Messenger in Innate Immune Signaling by Cytosolic DNA", Science, 2013, pp. 826-830, vol. 339.
Yamada et al., "Paracrine Receptor Activation by Microenvironment Triggers Bypass Survival Signals and ALK Inhibitor Resistance in EML4-ALK Lung Cancer Cells", Clin Cancer Res, 2012, pp. 3592-3602, vol. 18:13.
Yamaguchi et al., "Dual ALK and EGFR inhibition targets a mechanism of acquired resistance to the tyrosine kinase inhibitor crizotinib in ALK rearranged lung cancer", Lung Cancer, 2014, pp. 37-43, vol. 83.
Zhang et al., "Cyclic GMP-AMP Containing Mixed Phosphodiester Linkages is an Endogenous High-Affinity Ligand for STING", Molecular Cell, 2013, pp. 1-10, vol. 51.
Zhong et al., "The Adaptor Protein MITA Links Virus-Sensing Receptors to IRF3 Transcription Factor Activation", Immunity, 2008, pp. 538-550, vol. 29.
Ahn et al., "Self-DNA, STING-dependent signaling and the origins of autoinflammatory disease", Current Opinion in Immunology, 2014, pp. 121-126, vol. 31.
Andujar et al., "Beneficial Effects of Shikonin on Experimental Colitis Induced by Dextran Sulfate Sodium in Balb/C Mice", Evidence-Based Complementary and Alternative Medicine, 2012, pp. 1-15, vol. 2012.
Angus et al., "Severe Sepsis and Septic Shock", The New England Journal of Medicine, 2013, pp. 840-851, vol. 369:9.
Bakshi et al., "Identification of TBK1 complexes required for the phosphorylation of IRF3 and the production of Interferon ß", Biochemical Journal, 2017, pp. 1163-1174.
Barber, "STING: infection, inflammation and cancer", Nature, 2015, pp. 760-770, vol. 15.
Bilsland et al., "Behavioral and Neurochemical Alterations in Mice Deficient in Anaplastic Lymphoma Kinase Suggest Therapeutic Potential for Psychiatric Indications", Neuropsychopharmacology, 2008, pp. 685-700, vol. 33.
Bozza et al., "Cytokine profiles as markers of disease severity in sepsis: a multiplex analysis", Critical Care, 2007, pp. 1-8, vol. 11:R49.
Broz et al., "Newly described pattern recognition receptors team up against intracellular pathogens", Nature Reviews Immunology, 2013, pp. 551-565.
Buras et al., "Animal Models of Sepsis: Setting the Stage", Nature, 2005, pp. 854-865, vol. 4.
Burdette et al., "STING and the innate immune response to nucleic acids in the cytosol", Nature Immunology, 2013, pp. 19-26, vol. 14:1.
Burdette et al., "STING is a direct innate immune sensor of cyclic di-GMP", Nature, 2011, pp. 515-518, vol. 478.
Chakraborty et al., "Constitutive and ligand-induced EGFR signalling triggers distict and mutually exclusive downstream signalling networks", Nature Communications, 2014, pp. 1-15.
Chen et al., "Regulation and function of the cGAS-STING pathway of cytosolic DNA sensing", Nature Immunology, 2016, pp. 1142-1149, vol. 17:10.
Chiarle et al., "The analplastic lymphoma kinase in the pathogenesis of cancer", Nature Review, 2008, pp. 11-23, vol. 8.
Conlon et al., "Mouse, but not Human STING, Binds and Signals in Response to the Vascular Disrupting Agent 5,6-Dimethylxanthenone-4-Acetic Acid", The Journal of Immunology, 2013, pp. 5216-5225, vol. 190.
Corey, "Chemical modification: the key to clinical application of RNA interference?", J. Clin. Invest, 2007, pp. 3615-3622, vol. 117.
Danilchanka et al., "Cyclic Dinucleotides and the Innate Immune Response", Cell, 2013, pp. 962-970, vol. 154.
Davies et al., "Coordinated Regulation of Accessory Genetic Elements Produces Cyclic Di-Nucleotides for V. cholerae Virulence", Cell, 2012, pp. 358-370, vol. 149.
Dejager et al., "Cecal ligation and puncture: the gold standard model for polymicrobial sepsis?", Trends in Microbiology, 2011, pp. 198-208, vol. 19:4.
Deng et al., "Hemi: A Toolkit for Illustrating Heatmaps", Plos One, 2014, pp. 1-5, vol. 9:11.
Dinarello, "Interleukin-1 in the pathogenesis and treatment of inflammatory diseases", Blood, 2011, pp. 3720-3732, vol. 117:14.
Finlay et al., "Anti-Immunology: Evasion of the HOst Immune System by Bacterial and Viral Pathogens", Cell, 2006, pp. 767-782, vol. 124.
Fitzgerald et al., "IKKE and TBKI are essential components of the IRF3 signaling pathway", Nature Immunology, 2003, pp. 491-496, vol. 4:5.
Gatot et al., "Lipopolysaccharide-mediated Interferon Regulatory Factor Activation Involves TBK1-IKKE-dependent Lys63-linked Polyubiquitination and Phosphorylation of TANK/I-TRAF", Journal of Biological Chemistry, 2007, pp. 31131-31146, vol. 282:43.
Hefeneider et al., "Identification of a Cell-Surface DNA Receptor and Its Association with Systemic Lupus Erythematosus", J. Invest. Dermatol., 1990, pp. 79S-84S, vol. 94.
Heipertz et al., "STING and TRIF Contribute to Mouse Sepsis, Depending on Severity of the Disease Model", Shock, 2017, pp. 621-631, vol. 47:5.
Hotchkiss et al., "Sepsis-induced immunosuppression: from cellular dysfunctions to iummunotherapy", Nature, 2013, pp. 862-874, vol. 13.
Iwahara et al., "Molecular characterization of ALK, a receptor tyrosine kinase expressed specifically in the nervous system", Oncogene, 1997, pp. 439-449, vol. 14.
Ishikawa et al., "STING is an endoplasmic reticulum adaptor that facilitates innate immune signalling", Nature, 2008, pp. 674-678, vol. 455.
Ishikawa et al., "STING reulates intracellular DNA-mediated, type I interferon-dependent innate immunity", Nature, 2009, pp. 788-792, vol. 461.

(56) References Cited

OTHER PUBLICATIONS

Jensen, "Targeting the IL-1 family members in skin inflammation", Curr Opin Investig Drugs, 2010, pp. 1211-1220, vol. 11:11.
Jin et al., "MPYS is Required for IFN Response Factor 3 Activation and Type I IFN Production in the Response of Cultured Phagocytes to Bacterial Second Messengers Cyclic-di-AMP and Cyclic-di-GMP", J. Immunol, 2011, pp. 2595-2601, vol. 187.
Johnston Jr. et al., "Current Concepts: Immunology Monocytes and Macrophages", The New England Journal of Medicine, 1988, pp. 747-752, vol. 318:12.
Kaur et al., "Dual Regulatory Roles of the Phosphatidylinositol 3-Kinase in Interferon Signaling", J Immunol., 2008, pp. 7316-7323, vol. 181:10.
Kaur et al., "Rol of the Akt pathway in mRNA translation of interferon-stimulated genes", PNAS, 2008, pp. 4808-4813, vol. 105:12.
Kim et al., "Anticancer Flavonoids Are Mouse-Selective STING Agonists", ACS Chem. Biol., 2013, pp. 1396-1401, vol. 8.
Konno et al., "Cyclic Dinucleotides Trigger ULK1 (ATG1) Phosphorylation of STING to Prevent Sustained Innate Immune Signaling", Cell, 2013, pp. 688-698, vol. 155.
Kung et al., "Plasma nuclear and mitochondrial DNA levels as predictors of outcome in severe sepsis patients in the emergency room", Journal of Translational Medicine, 2012, pp. 1-8, vol. 10:130.
Li et al., "Ceritinib (LDK378): A Potent Alternative to Crizotinib for ALK-Rearranged Non-Small-Cell Lung Cancer", Clinical Lung Cancer, 2014, pp. 86-91, vol. 16.
Lima et al., "Single-Stranded siRNAs Activate RNAi in Animals", Cell, 2012, pp. 883-894, vol. 150.
Liu et al., "Phosphorylation of innate immune adaptor proteins MAVS, STING and TRIF induces IRF3 activation", Sciencexpress, 2015, pp. 1-17, www.sciencemag.org/content/early/recent.
Morris et al., "Fusion of a Kinase Gene, ALK, to a Nucleolar Protein Gene, NPM, in Non-Hodgkin's Lymphoma", Science, 1994, pp. 1281-1284, vol. 263.
Munford, "Endotoxemia-menace, marker, or mistake?", Journal of Leukocyte Biology, 2016, pp. 687-698, vol. 100.
NCBI Reference Sequence: NM_004304.4, "Homo sapiens ALK receiptor tyrosine kinase (ALK), transcript variant 1, mRNA", Printed Nov. 4, 2018.
NCBI Reference Sequence: NP_004295.2, "ALK tyrosine kinase receptor isoform 1 precursor [*Homo sapiens*]", Printed Feb. 10, 2019.
NCBI Reference Sequence: NM_004304.5, "*Homo sapiens* ALK receptor tyrosine kinase (ALK), transcript variant 1, mRNA", Printed Feb. 10, 2019.
Ou et al., "TBK1 Directly Engages Akt/PKB Survial Signaling to Support Oncogenic Transformation", Molecular Cell, 2011, pp. 458-470, vol. 41.
Pall, "The next-generation ALK inhibitors", Curr Opin Oncol, 2015, pp. 118-124, vol. 27:2.
Prantner et al., "5,6-Dimethylxanthenone-4-acetic Acid (DMXAA) Activates Stimulator of Interferon Gene (STING)-dependent Innate Immune Pathways and is Regulated by Mitochondrial Membrane Potential", The Journal of Biological Chemistry, 2012, pp. 39776-39788, vol. 287:47.
Presterl et al., "Cytokine Profile and Correlation to the APACHE III and MPM II Scores in Patient with Sepsis", Am J Respir Crit Care Med, 1997, pp. 825-832, vol. 156.

* cited by examiner

>NM_004304.5 Homo sapiens ALK receptor tyrosine kinase (ALK), transcript variant 1, mRNA
AGATGCGATCCAGCGGCTCTGGGGGCGGCAGCGGTGGTAGCAGCTGGTACCTCCCGCCGCCTCTGTTCGG
AGGGTCGCGGGGCACCGAGGTGCTTTCCGGCCGCCCTCTGGTCGGCCACCCAAAGCCGCGGGCGCTGATG
ATGGGTGAGGAGGGGGCGGCAAGATTTCGGGCGCCCCTGCCCTGAACGCCCTCAGCTGCTGCCGCCGGGG
CCGCTCCAGTGCCTGCGAACTCTGAGGAGCCGAGGCGCCGGTGAGAGCAAGGACGCTGCAAACTTGCGCA
GCGCGGGGGCTGGGATTCACGCCCAGAAGTTCAGCAGGCAGACAGTCCGAAGCCTTCCCGCAGCGGAGAG
ATAGCTTGAGGGTGCGCAAGACGGCAGCCTCCGCCCTCGGTTCCCGCCCAGACCGGGCAGAAGAGCTTGG
AGGAGCCAAAAGGAACGCAAAAGGCGGCCAGGACAGCGTGCAGCAGCTGGGAGCCGCCGTTCTCAGCCTT
AAAAGTTGCAGAGATTGGAGGCTGCCCCGAGAGGGGACAGACCCCAGCTCCGACTGCGGGGGGCAGGAGA
GGACGGTACCCAACTGCCACCTCCCTTCAACCATAGTAGTTCCTCTGTACCGAGCGCAGCGAGCTACAGA
CGGGGGCGCGGCACTCGGCGCGGAGAGCGGGAGGCTCAAGGTCCCAGCCAGTGAGCCCAGTGTGCTTGAG
TGTCTCTGGACTCGCCCCTGAGCTTCCAGGTCTGTTTCATTTAGACTCCTGCTCGCCTCCGTGCAGTTGG
GGGAAAGCAAGAGACTTGCGCGCACGCACAGTCCTCTGGAGATCAGGTGGAAGGAGCCGCTGGGTACCAA
GGACTGTTCAGAGCCTCTTCCCATCTCGGGGAGAGCGAAGGGTGAGGCTGGGCCCGGAGAGCAGTGTAAA
CGGCCTCCTCCGGCGGGATGGGAGCCATCGGGCTCCTGTGGCTCCTGCCGCTGCTGCTTTCCACGGCAGC
TGTGGGCTCCGGGATGGGGACCGGCCAGCGCGCGGGCTCCCCAGCTGCGGGGCCGCCGCTGCAGCCCCGG
GAGCCACTCAGCTACTCGCGCCTGCAGAGGAAGAGTCTGGCAGTTGACTTCGTGGTGCCCTCGCTCTTCC
GTGTCTACGCCCGGGACCTACTGCTGCCACCATCCTCCTCGGAGCTGAAGGCTGGCAGGCCCGAGGCCCG
CGGCTCGCTAGCTCTGGACTGCGCCCCGCTGCTCAGGTTGCTGGGGCCGGCGCCGGGGGTCTCCTGGACC
GCCGGTTCACCAGCCCCGGCAGAGGCCCGGACGCTGTCCAGGGTGCTGAAGGGCGGCTCCGTGCGCAAGC
TCCGGCGTGCCAAGCAGTTGGTGCTGGAGCTGGGCGAGGAGGCGATCTTGGAGGGTTGCGTCGGGCCCCC
CGGGGAGGCGGCTGTGGGGCTGCTCCAGTTCAATCTCAGCGAGCTGTTCAGTTGGTGGATTCGCCAAGGC
GAAGGGCGACTGAGGATCCGCCTGATGCCCGAGAAGAAGGCGTCGGAAGTGGGCAGAGAGGGAAGGCTGT
CCGCGGCAATTCGCGCCTCCCAGCCCCGCCTTCTCTTCCAGATCTTCGGGACTGGTCATAGCTCCTTGGA
ATCACCAACAAACATGCCTTCTCCTTCTCCTGATTATTTTACATGGAATCTCACCTGGATAATGAAAGAC
TCCTTCCCTTTCCTGTCTCATCGCAGCCGATATGGTCTGGAGTGCAGCTTTGACTTCCCCTGTGAGCTGG
AGTATTCCCCTCCACTGCATGACCTCAGGAACCAGAGCTGGTCCTGGCGCCGCATCCCCTCCGAGGAGGC
CTCCCAGATGGACTTGCTGGATGGGCCTGGGGCAGAGCGTTCTAAGGAGATGCCCAGAGGCTCCTTTCTC
CTTCTCAACACCTCAGCTGACTCCAAGCACACCATCCTGAGTCCGTGGATGAGGAGCAGCAGTGAGCACT
GCACACTGGCCGTCTCGGTGCACAGGCACCTGCAGCCCTCTGGAAGGTACATTGCCCAGCTGCTGCCCCA
CAACGAGGCTGCAAGAGAGATCCTCCTGATGCCCACTCCAGGGAAGCATGGTTGGACAGTGCTCCAGGGA
AGAATCGGGCGTCCAGACAACCCATTTCGAGTGGCCCTGGAATACATCTCCAGTGGAAACCGCAGCTTGT
CTGCAGTGGACTTCTTTGCCCTGAAGAACTGCAGTGAAGGAACATCCCCAGGCTCCAAGATGGCCCTGCA
GAGCTCCTTCACTTGTTGGAATGGGACAGTCCTCCAGCTTGGGCAGGCCTGTGACTTCCACCAGGACTGT
GCCCAGGGAGAAGATGAGAGCCAGATGTGCCGGAAACTGCCTGTGGGTTTTTACTGCAACTTTGAAGATG
GCTTCTGTGGCTGGACCCAAGGCACACTGTCACCCCACACTCCTCAATGGCAGGTCAGGACCCTAAAGGA
TGCCCGGTTCCAGGACCACCAAGACCATGCTCTATTGCTCAGTACCACTGATGTCCCCGCTTCTGAAAGT
GCTACAGTGACCAGTGCTACGTTTCCTGCACCGATCAAGAGCTCTCCATGTGAGCTCCGAATGTCCTGGC
TCATTCGTGGAGTCTTGAGGGGAAACGTGTCCTTGGTGCTAGTGGAGAACAAAACCGGGAAGGAGCAAGG
CAGGATGGTCTGGCATGTCGCCGCCTATGAAGGCTTGAGCCTGTGGCAGTGGATGGTGTTGCCTCTCCTC
GATGTGTCTGACAGGTTCTGGCTGCAGATGGTCGCATGGTGGGGACAAGGATCCAGAGCCATCGTGGCTT
TTGACAATATCTCCATCAGCCTGGACTGCTACCTCACCATTAGCGGAGAGGACAAGATCCTGCAGAATAC
AGCACCCAAATCAAGAAACCTGTTTGAGAGAAACCCAAACAAGGAGCTGAAACCCGGGGAAAATTCACCA
AGACAGACCCCCATCTTTGACCCTACAGTTCATTGGCTGTTCACCACATGTGGGGCCAGCGGGCCCCATG
GCCCCACCCAGGCACAGTGCAACAACGCCTACCAGAACTCCAACCTGAGCGTGGAGGTGGGGAGCGAGGG
CCCCCTGAAAGGCATCCAGATCTGGAAGGTGCCAGCCACCGACACCTACAGCATCTCGGGCTACGGAGCT
GCTGGCGGGAAAGGCGGGAAGAACACCATGATGCGGTCCCACGGCGTGTCTGTGCTGGGCATCTTCAACC
TGGAGAAGGATGACATGCTGTACATCCTGGTTGGGCAGCAGGGAGAGGACGCCTGCCCCAGTACAAACCA
GTTAATCCAGAAAGTCTGCATTGGAGAGAACAATGTGATAGAAGAAGAAATCCGTGTGAACAGAAGCGTG
CATGAGTGGGCAGGAGGCGGAGGAGGAGGGGGTGGAGCCACCTACGTATTTAAGATGAAGGATGGAGTGC
CGGTGCCCCTGATCATTGCAGCCGGAGGTGGTGGCAGGGCCTACGGGGCCAAGACAGACACGTTCCACCC
AGAGAGACTGGAGAATAACTCCTCGGTTCTAGGGCTAAACGGCAATTCCGGAGCCGCAGGTGGTGGAGGT
GGCTGGAATGATAACACTTCCTTGCTCTGGGCCGGAAAATCTTTGCAGGAGGGTGCCACCGGAGGACATT

FIG. 1A-1

CCTGCCCCCAGGCCATGAAGAAGTGGGGGTGGGAGACAAGAGGGGGTTTCGGAGGGGGTGGAGGGGGGTG
CTCCTCAGGTGGAGGAGGCGGAGGATATATAGGCGGCAATGCAGCCTCAAACAATGACCCCGAAATGGAT
GGGGAAGATGGGGTTTCCTTCATCAGTCCACTGGGCATCCTGTACACCCCAGCTTTAAAAGTGATGGAAG
GCCACGGGGAAGTGAATATTAAGCATTATCTAAACTGCAGTCACTGTGAGGTAGACGAATGTCACATGGA
CCCTGAAAGCCACAAGGTCATCTGCTTCTGTGACCACGGGACGGTGCTGGCTGAGGATGGCGTCTCCTGC
ATTGTGTCACCCACCCCGGAGCCACACCTGCCACTCTCGCTGATCCTCTCTGTGGTGACCTCTGCCCTCG
TGGCCGCCCTGGTCCTGGCTTTCTCCGGCATCATGATTGTGTACCGCCGGAAGCACCAGGAGCTGCAAGC
CATGCAGATGGAGCTGCAGAGCCCTGAGTACAAGCTGAGCAAGCTCCGCACCTCGACCATCATGACCGAC
TACAACCCCAACTACTGCTTTGCTGGCAAGACCTCCTCCATCAGTGACCTGAAGGAGGTGCCGCGGAAAA
ACATCACCCTCATTCGGGGTCTGGGCCATGGCGCCTTTGGGGAGGTGTATGAAGGCCAGGTGTCCGGAAT
GCCCAACGACCCAAGCCCCCTGCAAGTGGCTGTGAAGACGCTGCCTGAAGTGTGCTCTGAACAGGACGAA
CTGGATTTCCTCATGGAAGCCCTGATCATCAGCAAATTCAACCACCAGAACATTGTTCGCTGCATTGGGG
TGAGCCTGCAATCCCTGCCCCGGTTCATCCTGCTGGAGCTCATGGCGGGGGGAGACCTCAAGTCCTTCCT
CCGAGAGACCCGCCCTCGCCCGAGCCAGCCCTCCTCCCTGGCCATGCTGGACCTTCTGCACGTGGCTCGG
GACATTGCCTGTGGCTGTCAGTATTTGGAGGAAAACCACTTCATCCACCGAGACATTGCTGCCAGAAACT
GCCTCTTGACCTGTCCAGGCCCTGGAAGAGTGGCCAAGATTGGAGACTTCGGGATGGCCCGAGACATCTA
CAGGGCGAGCTACTATAGAAAGGGAGGCTGTGCCATGCTGCCAGTTAAGTGGATGCCCCCAGAGGCCTTC
ATGGAAGGAATATTCACTTCTAAAACAGACACATGGTCCTTTGGAGTGCTGCTATGGGAAATCTTTTCTC
TTGGATATATGCCATACCCCAGCAAAAGCAACCAGGAAGTTCTGGAGTTTGTCACCAGTGGAGGCCGGAT
GGACCCACCCAAGAACTGCCCTGGGCCTGTATACCGGATAATGACTCAGTGCTGGCAACATCAGCCTGAA
GACAGGCCCAACTTTGCCATCATTTTGGAGAGGATTGAATACTGCACCCAGGACCCGGATGTAATCAACA
CCGCTTTGCCGATAGAATATGGTCCACTTGTGGAAGAGGAAGAGAAAGTGCCTGTGAGGCCCAAGGACCC
TGAGGGGGTTCCTCCTCTCCTGGTCTCTCAACAGGCAAAACGGGAGGAGGAGCGCAGCCCAGCTGCCCCA
CCACCTCTGCCTACCACCTCCTCTGGCAAGGCTGCAAAGAAACCCACAGCTGCAGAGATCTCTGTTCGAG
TCCCTAGAGGGCCGGCCGTGGAAGGGGGACACGTGAATATGGCATTCTCTCAGTCCAACCCTCCTTCGGA
GTTGCACAAGGTCCACGGATCCAGAAACAAGCCCACCAGCTTGTGGAACCCAACGTACGGCTCCTGGTTT
ACAGAGAAACCCACCAAAAAGAATAATCCTATAGCAAAGAAGGAGCCACACGACAGGGGTAACCTGGGGC
TGGAGGGAAGCTGTACTGTCCCACCTAACGTTGCAACTGGGAGACTTCCGGGGGCCTCACTGCTCCTAGA
GCCCTCTTCGCTGACTGCCAATATGAAGGAGGTACCTCTGTTCAGGCTACGTCACTTCCCTTGTGGGAAT
GTCAATTACGGCTACCAGCAACAGGGCTTGCCCTTAGAAGCCGCTACTGCCCCTGGAGCTGGTCATTACG
AGGATACCATTCTGAAAAGCAAGAATAGCATGAACCAGCCTGGGCCCTGAGCTCGGTCGCACACTCACTT
CTCTTCCTTGGGATCCCTAAGACCGTGGAGGAGAGAGAGGCAATGGCTCCTTCACAAACCAGAGACCAAA
TGTCACGTTTTGTTTTGTGCCAACCTATTTTGAAGTACCACCAAAAAAGCTGTATTTTGAAAATGCTTTA
GAAAGGTTTTGAGCATGGGTTCATCCTATTCTTTCGAAAGAAGAAAATATCATAAAAATGAGTGATAAAT
ACAAGGCCCAGATGTGGTTGCATAAGGTTTTTATGCATGTTTGTTGTATACTTCCTTATGCTTCTTTCAA
ATTGTGTGTGCTCTGCTTCAATGTAGTCAGAATTAGCTGCTTCTATGTTTCATAGTTGGGGTCATAGATG
TTTCCTTGCCTTGTTGATGTGGACATGAGCCATTTGAGGGGAGAGGGAACGGAAATAAAGGAGTTATTTG
TAATGACTAA

FIG. 1A-2

>NP_004295.2 ALK tyrosine kinase receptor isoform 1 precursor [Homo sapiens]
MGAIGLLWLLPLLLSTAAVGSGMGTGQRAGSPAAGPPLQPREPLSYSRLQRKSLAVDFVVPSLFRVYARD
LLLPPSSSELKAGRPEARGSLALDCAPLLRLLGPAPGVSWTAGSPAPAEARTLSRVLKGGSVRKLRRAKQ
LVLELGEEAILEGCVGPPGEAAVGLLQFNLSELFSWWIRQGEGRLRIRLMPEKKASEVGREGRLSAAIRA
SQPRLLFQIFGTGHSSLESPTNMPSPSPDYFTWNLTWIMKDSFPFLSHRSRYGLECSFDFPCELEYSPPL
HDLRNQSWSWRRIPSEEASQMDLLDGPGAERSKEMPRGSFLLLNTSADSKHTILSPWMRSSSEHCTLAVS
VHRHLQPSGRYIAQLLPHNEAAREILLMPTPGKHGWTVLQGRIGRPDNPFRVALEYISSGNRSLSAVDFF
ALKNCSEGTSPGSKMALQSSFTCWNGTVLQLGQACDFHQDCAQGEDESQMCRKLPVGFYCNFEDGFCGWT
QGTLSPHTPQWQVRTLKDARFQDHQDHALLLSTTDVPASESATVTSATFPAPIKSSPCELRMSWLIRGVL
RGNVSLVLVENKTGKEQGRMVWHVAAYEGLSLWQWMVLPLLDVSDRFWLQMVAWWGQGSRAIVAFDNISI
SLDCYLTISGEDKILQNTAPKSRNLFERNPNKELKPGENSPRQTPIFDPTVHWLFTTCGASGPHGPTQAQ
CNNAYQNSNLSVEVGSEGPLKGIQIWKVPATDTYSISGYGAAGGKGGKNTMMRSHGVSVLGIFNLEKDDM
LYILVGQQGEDACPSTNQLIQKVCIGENNVIEEEIRVNRSVHEWAGGGGGGGATYVFKMKDGVPVPLII
AAGGGGRAYGAKTDTFHPERLENNSSVLGLNGNSGAAGGGGGWNDNTSLLWAGKSLQEGATGGHSCPQAM
KKWGWETRGGFGGGGGGCSSGGGGGGYIGGNAASNNDPEMDGEDGVSFISPLGILYTPALKVMEGHGEVN
IKHYLNCSHCEVDECHMDPESHKVICFCDHGTVLAEDGVSCIVSPTPEPHLPLSLILSVVTSALVAALVL
AFSGIMIVYRRKHQELQAMQMELQSPEYKLSKLRTSTIMTDYNPNYCFAGKTSSISDLKEVPRKNITLIR
GLGHGAFGEVYEGQVSGMPNDPSPLQVAVKTLPEVCSEQDELDFLMEALIISKFNHQNIVRCIGVSLQSL
PRFILLELMAGGDLKSFLRETRPRPSQPSSLAMLDLLHVARDIACGCQYLEENHFIHRDIAARNCLLTCP
GPGRVAKIGDFGMARDIYRASYYRKGGCAMLPVKWMPPEAFMEGIFTSKTDTWSFGVLLWEIFSLGYMPY
PSKSNQEVLEFVTSGGRMDPPKNCPGPVYRIMTQCWQHQPEDRPNFAIILERIEYCTQDPDVINTALPIE
YGPLVEEEEKVPVRPKDPEGVPPLLVSQQAKREEERSPAAPPPLPTTSSGKAAKKPTAAEISVRVPRGPA
VEGGHVNMAFSQSNPPSELHKVHGSRNKPTSLWNPTYGSWFTEKPTKKNNPIAKKEPHDRGNLGLEGSCT
VPPNVATGRLPGASLLLEPSSLTANMKEVPLFRLRHFPCGNVNYGYQQQGLPLEAATAPGAGHYEDTILK
SKNSMNQPGP

FIG. 1B

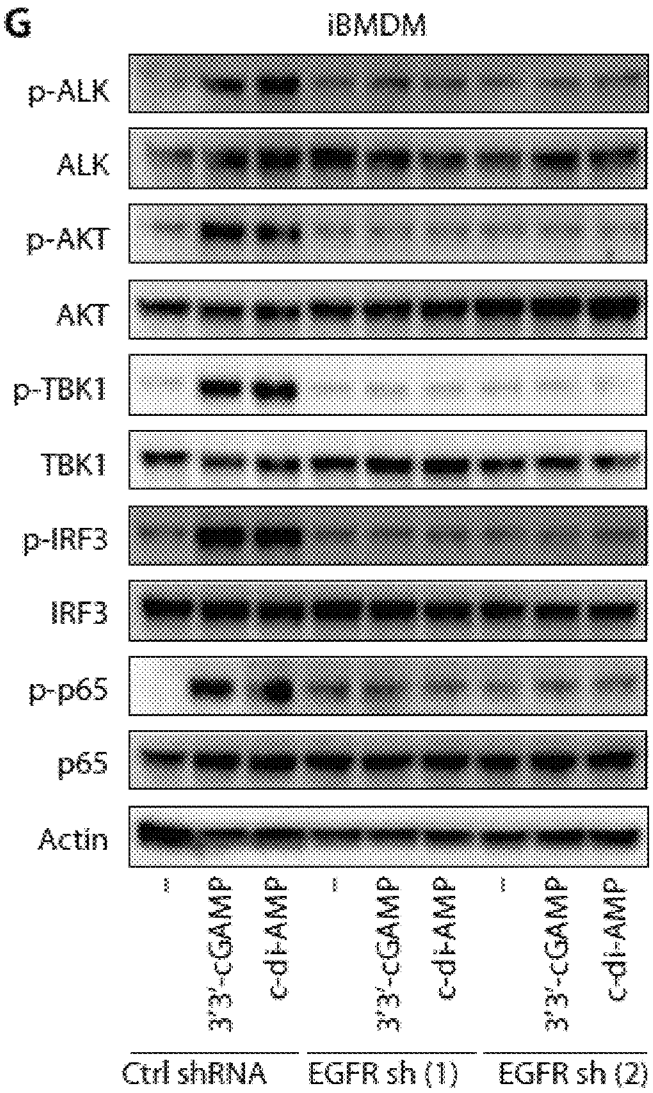
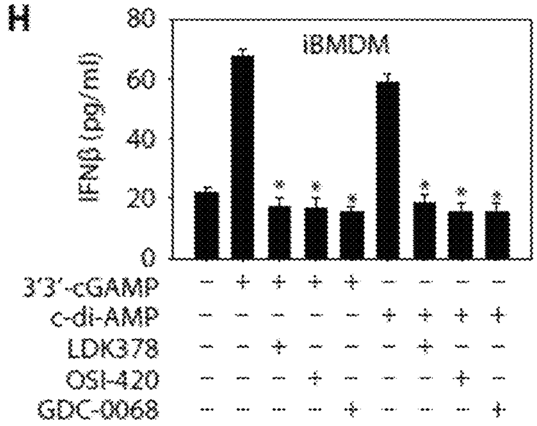
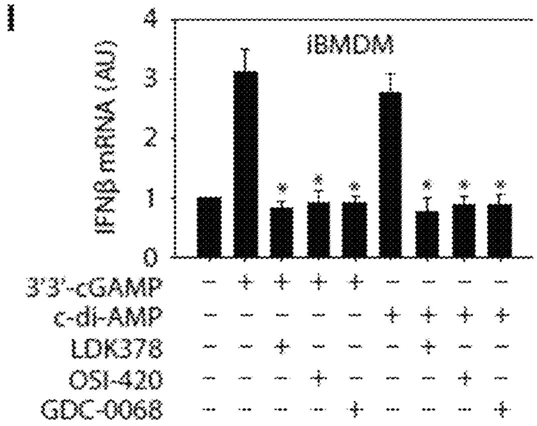
FIG. 9D

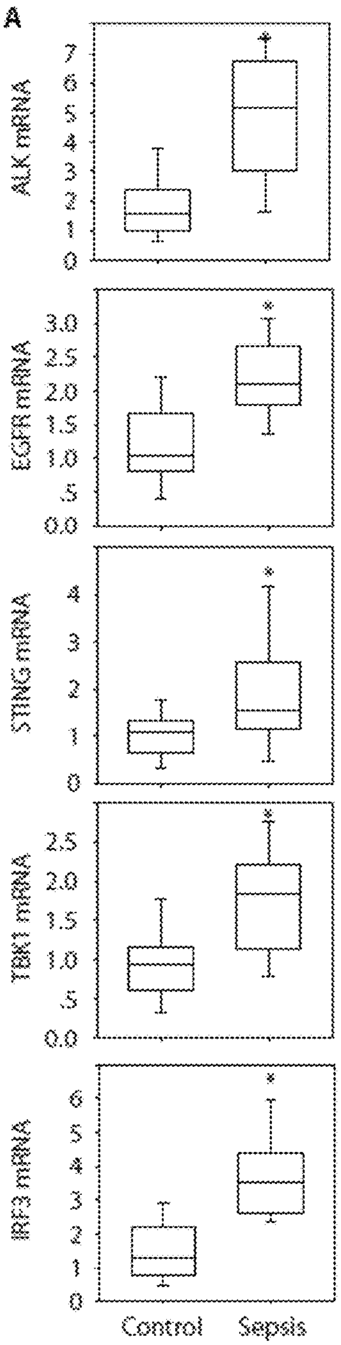
B
Clinical characteristics of sepsis patients and the healthy control individuals
| | Control group (*n* = 16) | Sepsis group (*n* = 16) |
|---|---|---|
| Age, mean (SD) | 38.9 (18.9) | 48.5 (14.3) |
| Gender *n* (%)<br>Male<br>Female | <br>10 (62.5)<br>6 (37.5) | <br>12 (75)<br>4 (25) |
| SOFA, mean (SD) | N/A | 5.8 (2.4) |
| In-hospital mortality, *n* (%)<br>Yes<br>No | <br>N/A<br>N/A | <br>4 (25)<br>12 (75) |
| Length of stay, days, median (range) | N/A | 24.5 (3, 49) |
N/A, not applicable
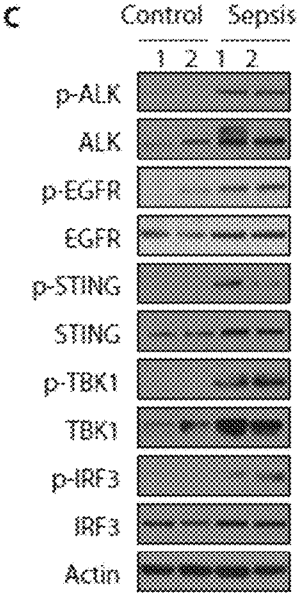
*Fig. 25*

METHODS OF TREATING CONDITIONS INVOLVING ELEVATED INFLAMMATORY RESPONSE

CROSS REFERENCE TO RELATED APPLICATIONS

This application claims the benefit of U.S. Provisional Patent Application No. 62/594,162 filed Dec. 4, 2017, and U.S. Provisional Patent Application No. 62/608,835 filed Dec. 21, 2017, each of which is incorporated herein by reference in its entirety.

STATEMENT REGARDING FEDERAL FUNDING

This invention was made with government support under Grant No. GM115366 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 6527-1806994_ST25.txt. The size of the text file is 26,716 bytes, and the text file was created on Dec. 3, 2018.

Provided herein are methods of reducing an inflammatory response in a patient and methods of treating diseases and conditions in a patient involving an elevated inflammatory response.

Sepsis is among the most common causes of death in hospitals and one of the most elusive syndromes in medicine. Although the word "sepsis" was first introduced by Hippocrates, clinical criteria for the definition of sepsis and septic shock remain challenging. Sepsis is now defined as life-threatening organ dysfunction due to a dysregulated host response to infection. Pathogenesis of the sepsis syndrome relies critically on the activation of innate immunity by a large family of pattern recognition receptors (PRRs) in response to microbial pathogens, including especially Gram-negative bacilli (*E. coli* and *P. aeruginosa*). Mechanistically, immune chemicals (cytokines, chemokines, and growth factors) released by various innate immune cells trigger both pro- and anti-inflammatory immune responses, which can lead to organ dysfunction or failure, and even death. In these contexts, pharmacological inhibition of key inflammatory regulators that control the overwhelming immune response could be useful for therapy for sepsis as well as for other diseases or conditions involving an elevated inflammatory response.

The stimulator of interferon genes (STING) is a transmembrane adaptor protein critically involved in the innate immune response to cyclic dinucleotides (CDNs) that are produced by bacteria or metabolized from double-stranded DNA (dsDNA) by cyclic-guanosine monophosphate-adenosine monophosphate (cGAMP) synthase (cGAS). Impairment of the STING pathway has been associated with the pathogenesis of several human diseases, including infections, inflammatory, and autoimmune diseases, and cancers. Structurally, STING forms a complex with the TANK-binding kinase 1 (TBK1) to enable its phosphorylation, which results in activation of both interferon (IFN) regulatory factor 3 (IRF3) and nuclear factor κB (NF-κB) signaling pathways, leading to the consequent production of type I IFNs and other proinflammatory cytokines. Despite substantial investigation of the signaling pathways leading to STING activation, other key regulators of the STING signaling pathway remain to be elucidated.

Treatment of diseases or conditions involving elevated inflammation is often difficult and complex. Further, recovery from conditions can be hampered by inflammation, and reduction of inflammation can lead to increased life span and/or health span. As such, methods of controlling inflammation in a patient are needed.

SUMMARY

As described herein, a method of decreasing inflammation, for example in treating an inflammatory disease or condition, in a patient is provided. The inflammation is caused, e.g., by activation of a type 1 IFN response, e.g., by STING. It is determined that kinase inhibitors, such as inhibitors of anaplastic lymphoma kinase (ALK inhibitors) decrease production of type I IFN (e.g. IFN-α and IFN-β) in cells stimulated with cyclic guanosine monophosphate-adenosine monophosphate (cGAMP, or 3'3'-cGAMP) and are therefore useful in treating an inflammatory disease.

In one aspect, a method of reducing a type I interferon (IFN) response in a patient having an inflammatory disease is provided. The method comprises administering to the patient an amount of an ALK inhibitor or an inhibitor of ALK expression effective to reduce a type I interferon response in a patient.

In another aspect, a method of treating an inflammatory disease in a patient is provided. The method comprises administering to the patient an amount of an ALK inhibitor effective to treat the inflammatory disease in a patient.

In another aspect, a method of improving a patient's health-span or life-span is provided. The method comprising administering to the patient an amount of an ALK inhibitor or an inhibitor of ALK expression effective to decrease a type I interferon (IFN) response or a stimulator of interferon genes (STING) response in a patient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B provide exemplary mRNA and protein sequences for ALK, including NM_004304.5 (FIG. 1A, SEQ ID NO: 1) and NP_004295.2 (FIG. 1B, SEQ ID NO: 1).

(FIG. 7A) Western blot analysis of ALK expression in ALK stable knockdown iBMDMs (n=3, data expressed as means±SD, *P<0.05 versus control shRNA group, t test). (FIGS. 7B-7D) Indicated iBMDMs were stimulated with 3'3'-cGAMP (10 μg/ml) or c-di-AMP (10 μg/ml) for 16 hours, and cell morphology (B), viability (C), and cell cycle phase (D) were assayed (bar=200 μM). (FIGS. 7E, 7F). Indicated iBMDMs were stimulated with indicated STING ligands (10 μg/ml) for 16 hours, and IFNβ protein release (E) and IFNβ mRNA (F) were assayed (n=3, data expressed as means±SD, *P<0.05 versus control shRNA group, ANOVA LSD test). (FIGS. 7G, 7H) Heatmap of IFNβ protein release (G) and IFNβ mRNA expression (FIG. 7H) changes in indicated ALK-WT and ALK-knockdown macrophages or monocytes after STING ligand (10 μg/ml) stimulation for 16 hours. (FIG. 7I) Western blot analysis of indicated protein expression in ALK-WT and ALK-knockdown iBMDMs after stimulation with 3'3'-cGAMP (10 μg/ml), c-di-AMP (10 μg/ml), or DMXAA (10 μg/ml) for 16 hours.

FIGS. 9A-9D. ALK/EGFR binding triggers AKT-dependent STING activation. (A) Western blot analysis of indicated protein expression in iBMDMs, RAW264.7, and THP1 cells after stimulation with 3'3'-cGAMP (10 μg/ml), c-di-AMP (10 μg/ml), or DMXAA (10 μg/ml) for 16 hours. (B) Heatmap of receptor tyrosine kinases phosphorylation changes in iBMDMs after 3'3'-cGAMP (10 μg/ml) or c-di-AMP (10 μg/ml) stimulation for 16 hours with or without pharmacologic (LDK378, 10 μM) or genetic inhibition of ALK. (C) Relative EGFR phosphorylation assayed in parallel to (B). (D) IP analysis of the interaction between ALK and EGFR in iBMDMs after 3'3'-cGAMP (10 μg/ml) or c-di-AMP (10 μg/ml) stimulation for 16 hours with or without LDK378 (10 μM) or OSI-420 (10 μM). (E) Western blot analysis of indicated protein expression in iBMDMs after treatment with 3'3'-cGAMP (10 μg/ml) or c-di-AMP (10 μg/ml) for 16 hours with or without LDK378 (10 μM), OSI-420 (10 μM), or GDC-0068 (10 μM). (F) Western blot analysis of EGFR expression in EGFR stable knockdown iBMDMs. (G) Western blot analysis of indicated protein expression in EGFR-WT and EGFR-knockdown iBMDMs after stimulation with 3'3'-cGAMP (10 μg/ml) or c-di-AMP (10 μg/ml) for 16 hours. (H, I) iBMDMs were treated with 3'3'-cGAMP (10 μg/ml) or c-di-AMP (10 μg/ml) for 16 hours with or without LDK378 (10 μM), OSI-420 (10 μM), or GDC-0068 (10 μM), and IFNβ protein release (H) and IFNβ mRNA expression (I) were assayed (n=3, data expressed as means±SD, *P<0.05 versus 3'3'-cGAMP or c-di-AMP group, ANOVA LSD test).

FIG. 25. Gene and protein changes in ALK-dependent STING pathways in human sepsis. (A) Box plots comparing measures of ALK, EGFR, STING, TBK1, and IRF3 mRNA in PBMC samples of sepsis patients (n=16) and healthy controls (n=16). The mRNAs are presented as median value (black line), interquartile range (box), and minimum and maximum of all data (black line). *, $P<0.05$ versus control group, t test. (B) Table depicting clinical characteristics of sepsis patients and healthy control individuals. (C) Western blot analysis of indicated protein expression in PBMC samples of sepsis patients and healthy controls.

DETAILED DESCRIPTION

Figure 2A:
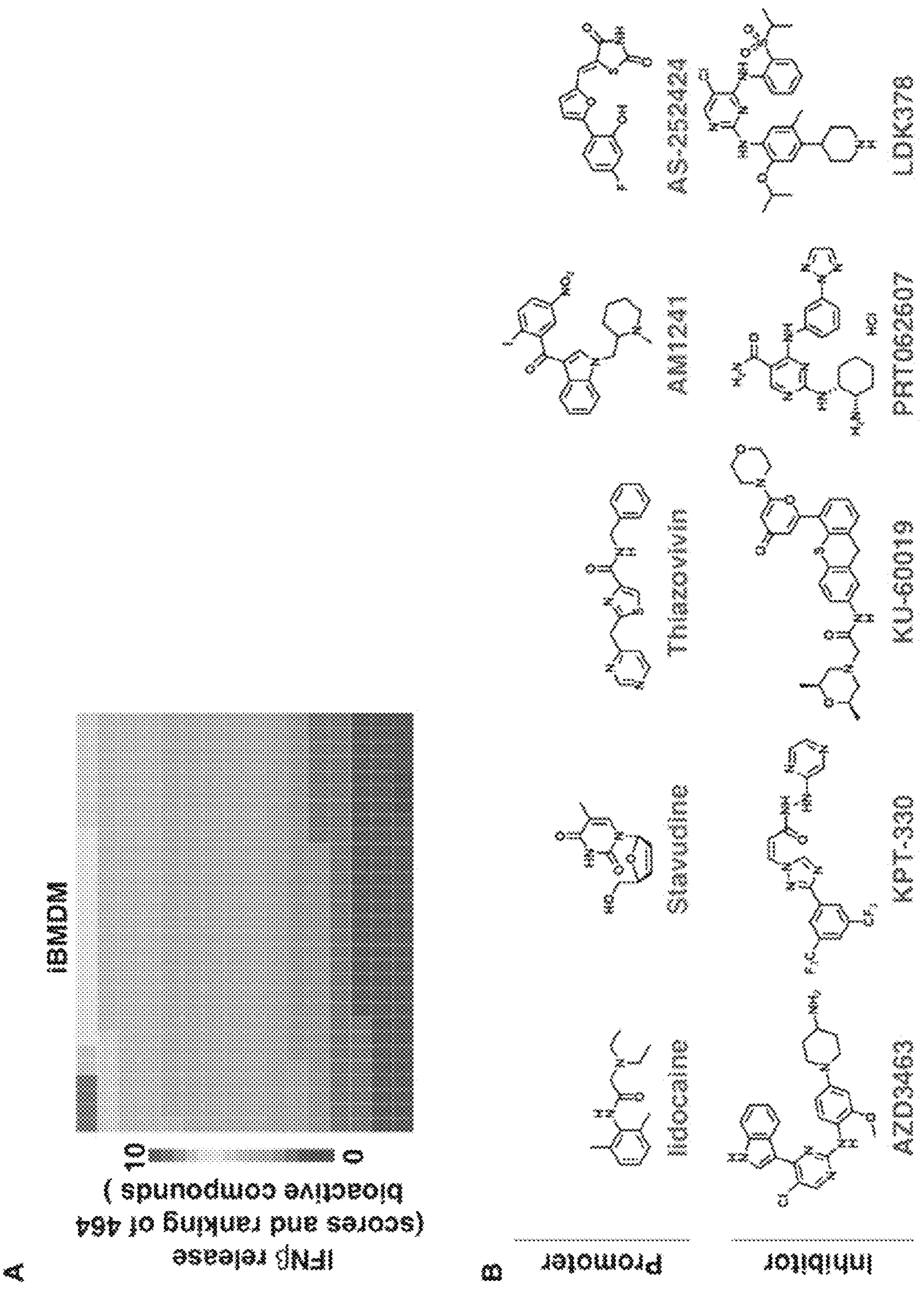
FIGS. 2A and 2B. Identification of bioactive compounds modulating STING activation. (Panel A (A)) Heatmap of STING activity changes based on IFNβ release from iBMDMs after 3'3'-cGAMP (10 μg/ml, 16 hours) stimulation in the absence or presence of 464 bioactive compounds (10 μM). (B) The structure of the compound identified to inhibit (blue) or promote (red) STING activity. (C-E) IFNβ release assayed using ELISA from iBMDMs (C), pPMs (D), and pPBMCs (E) treated with 3'3'-cGAMP (10 μg/ml) in the absence or presence of indicated bioactive compounds (10 μM) for 16 hours (n=3, data expressed as means±SD, *P<0.05 versus 3'3'-cGAMP group, ANOVA LSD test). (F) Heatmap of STING activity changes as judged by IFNβ release from iBMDMs after 3'3'-cGAMP (10 μg/ml, 16 hours) stimulation in the absence or presence of 174 signaling modulating compounds. The top five negative (inhibitory) and positive (agonistic) regulators are noted.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of"

limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

A "patient" is a human or animal, e.g., vertebrates or mammals, including rat, mouse, rabbit, pig, monkey, chimpanzee, cat, dog, horse, goat, guinea pig, and birds, and does not imply or require a doctor-patient or veterinarian-patient relationship.

As used herein, the "treatment" or "treating" of an inflammatory disease (e.g., a condition, syndrome, or disorder), such as those listed below, in a patient, means administration to a patient by any suitable dosage regimen, procedure and/or administration route of a composition, device, or structure with the object of achieving a beneficial or desirable clinical/medical end-point, including but not limited to, preventing, reducing, and/or eliminating any symptom of an inflammatory disease that, for example involves a type 1 interferon or stimulator of interferon genes (STING) response in a patient. An amount of any agent, administered by any suitable route, effective to treat a patient is an amount capable of preventing, reducing, and/or eliminating any symptom of an inflammatory disease that, for example involves a type 1 interferon or stimulator of interferon genes (STING) response, in a patient.

The compositions described herein can be administered by any effective route, such as parenteral, e.g., intravenous, intramuscular, subcutaneous, intradermal, etc., formulations of which are described below and in the below-referenced publications, as well as is broadly-known to those of ordinary skill in the art.

Suitable dosage forms may include single-dose, or multiple-dose vials or other containers, such as medical syringes, containing a composition comprising an active ingredient useful for treatment of an inflammatory disease that, for example involves a type 1 interferon or stimulator of interferon genes (STING) response, as described herein.

By "expression" or "gene expression," it is meant the overall flow of information from a gene, to produce a gene product. A "gene" is, without limitation, a functional genetic unit for producing a gene product, such as RNA or a protein in a cell, or other expression system encoded on a nucleic acid and comprising: a transcriptional control sequence, such as a promoter and other cis-acting elements, such as transcriptional response elements (TREs) and/or enhancers; an expressed sequence that typically encodes a protein (referred to as an open-reading frame or ORF) or functional/structural RNA, and a polyadenylation sequence. A "gene product" typically is a protein, optionally post-translationally modified, or a functional/structural RNA. Expression of a gene can be downregulated, that is lowering levels or activity of the gene product of the gene, for example by lowering transcription rates from the gene, reducing transcribed RNA levels, reducing or inhibiting post-transcriptional processing of the gene product, by enhanced degradation of the gene product thereby reducing the availability of the gene product, or by any other mechanism that renders the gene product less available. Downregulation of a gene can be accomplished, for example and without limitation, pharmacologically by administering to a patient an inhibitor of gene expression, or by RNA interference. Likewise, expression of a gene can be upregulated, that is increasing levels or activity of the gene product of the gene, for example by inducing or otherwise increasing transcription rates from the gene, by increasing RNA stability, by increasing post-transcriptional processing of the gene product, by reduced degradation of the gene product and thereby increasing the availability of the gene product, or by any other mechanism that renders the gene product more active or available. "Activity" of a gene product, such as an enzyme, refers to the overall ability of a gene product in a cell, tissue, or organism, to function, e.g. to catalyze a certain reaction, or to bind a binding partner such as a receptor, factor, protein, etc. Activity can be a function of expression of the gene product, or can be affected by extrinsic factors, such as, for example and without limitation, the presence of antagonists, agonists, cofactors; presence of or absence of substrate or product; presence of, absence of, or mutations in binding partners; and/or physical factors, such as pH or salt concentration.

Complementary refers to the ability of polynucleotides (nucleic acids) to hybridize to one another, forming inter-strand base pairs. Base pairs are formed by hydrogen bonding between nucleotide units in antiparallel polynucleotide strands. Complementary polynucleotide strands can base pair (hybridize) in the Watson-Crick manner (e.g., A to T, A to U, C to G), or in any other manner that allows for the formation of duplexes. When using RNA as opposed to DNA, uracil rather than thymine is the base that is considered to be complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be fully complementary, or have 100% sequence identity (gaps are not counted and the measurement is in relation to the shorter of the two sequences). In one aspect, a sequence that "specifically hybridizes" to another sequence, does so in a hybridization solution containing 0.5M sodium phosphate buffer, pH 7.2, containing 7% SDS, 1 mM EDTA, and 100 mg/ml of salmon sperm DNA at 65° C. for 16 hours and washing twice at 65° C. for twenty minutes in a washing solution containing 0.5×SSC and 0.1% SDS, or does so under conditions more stringent than 2×SSC at 65° C., for example, in 0.2×SSC at 55° C. A sequence that specifically hybridizes to another typically has at least 80%, 85%, 90%, 95%, or 99% sequence identity with the other sequence.

ALK (NCBI Gene ID: 238) is a gene encoding the anaplastic lymphoma kinase or ALK Receptor Tyrosine Kinase, which is a receptor tyrosine kinase. ALK plays an important role in the development of the brain and exerts its effects on specific neurons in the nervous system. This gene has been found to be rearranged, mutated, or amplified in a series of tumours including anaplastic large cell lymphomas, neuroblastoma, and non-small cell lung cancer. Exemplary mRNA and protein sequences (ALK tyrosine kinase receptor isoform 1 precursor) include NM_004304.5 (FIG. 1A, SEQ ID NO: 1) and NP_004295.2 (FIG. 1B, SEQ ID NO: 1), respectively.

In addition to ALK inhibitors, e.g. as described herein, ALK expression can be knocked down or decreased by use of RNA interference or antisense technologies, as are broadly-known. RNAi agents, such as siRNAs (short interfering RNA) or shRNAs (short hairpin RNAs), as are broadly-known. Exemplary human shRNAs targeting ALK include: CCGGGTGATAAATACAAGGCCCAGACTCGAGTCTGGGCCTTGTATTTATCA CTTTTT (SEQ ID NO: 3), or CCGGAGAAGAAGAAATCCGTGTGAA CTCGAGTTCACACGGATTTCTTCTTCTTTTT (SEQ ID NO: 4). RNAi agents can be pooled in order to better target mRNAs and to address allelic variation. Of note, unless otherwise specified, nucleotide sequences are provided in a 5' to 3' direction and protein sequences, in an N-terminal to C-terminal direction. siRNA agents that target ALK are commercially available, such as from Dharmacon of Lafayette, Colo., Santa Cruz Biotechnology, Inc., and Thermofisher Scientific. For example, ThermoFisher sells twelve different siRNAs targeting different locations in the ALK mRNA sequence, referencing locations (bases 1112, 1623, 1742, 1899, 2039, 2109, 2509, 2922, 2923, 3261, 3317, and 5025) in GenBank Accession No. NM_004304.4, a predecessor to Reference Sequence NM_004304.5 (FIG. 1A).

Transcription is the process by which the DNA gene sequence is transcribed into pre-mRNA (messenger RNA). The steps include: RNA polymerase, together with one or more general transcription factors, binds to promoter DNA. Transcription factors (TFs) are proteins that control the rate of transcription of genetic information from DNA to messenger RNA, by binding to a specific DNA sequence (e.g., the promoter region). The function of TFs is to regulate genes in order to make sure that they are expressed in the right cell at the right time and in the right amount throughout the life of the cell and the organism. The promoter region of a gene is a region of DNA that initiates transcription of that particular gene. Promoters are located near the transcription start sites of genes, on the same strand, and often, but not exclusively, are upstream (towards the 5' region of the sense strand) on the DNA. Promoters can be about 100-1000 base pairs long. Additional sequences and non-coding elements can affect transcription rates. If the cell has a nucleus (eukaryotes), the RNA is further processed. This includes polyadenylation, capping, and splicing. Polyadenylation is the addition of a poly(A) tail to a messenger RNA. The poly(A) tail consists of multiple adenosine monophosphates; in other words, it is a stretch of RNA that has only adenine bases. In eukaryotes, polyadenylation is part of the process that produces mature messenger RNA (mRNA) for translation. Capping refers to the process wherein the 5' end of the pre-mRNA has a specially altered nucleotide. In eukaryotes, the 5' cap (cap-0), found on the 5' end of an mRNA molecule, consists of a guanine nucleotide connected to mRNA via an unusual 5' to 5' triphosphate linkage. During RNA splicing, pre-mRNA is edited. Specifically, during this process introns are removed and exons are joined together. The resultant product is known as mature mRNA. The RNA may remain in the nucleus or exit to the cytoplasm through the nuclear pore complex.

RNA levels in a cell, e.g., mRNA levels, can be controlled post-transcriptionally. Native mechanisms, including: endogenous gene silencing mechanisms, interference with translational mechanisms, interference with RNA splicing mechanisms, and destruction of duplexed RNA by RNAse H, or RNAse H-like, activity. As is broadly-recognized by those of ordinary skill in the art, these endogenous mechanisms can be exploited to decrease or silence mRNA activity in a cell or organism in a sequence-specific, targeted manner. Antisense technology typically involves administration of a single-stranded antisense oligonucleotide (ASO) that is chemically-modified, e.g., as described herein, for bio-stability, and is administered in sufficient amounts to effectively penetrate the cell and bind in sufficient quantities to target mRNAs in cells. RNA interference (RNAi) harnesses an endogenous and catalytic gene silencing mechanism, which means that once, e.g., a microRNA, or double-stranded siRNA has been delivered, either by conjugation or in nanoparticles into the cytosol, they are efficiently recognized and stably incorporated into the RNA-induced silencing complex (RiSC) to achieve prolonged gene silencing. Both antisense technologies and RNAi have their strengths and weaknesses, either may be used effectively to decrease or silence expression of a gene or gene product, such as ALK (see, e.g., Watts, J. K., et al. Gene silencing by siRNAs and antisense oligonucleotides in the laboratory and the clinic (2012) 226(2):365-379).

The terms "iRNA," "RNAi agent," "iRNA agent," and "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits or knocks down, the expression of ALK mRNA in a cell, e.g., a cell within a subject, such as a mammalian subject.

In one aspect, an RNAi agent includes a single stranded RNAi that interacts with a target RNA sequence, e.g., a ALK mRNA sequence, to direct the cleavage of the target RNA. Without wishing to be bound by theory it is believed that long double stranded RNA introduced into cells is broken down into double stranded short interfering RNAs (siRNAs) comprising a sense strand and an antisense strand by a Type III endonuclease known as Dicer. Dicer, a ribonuclease-III-like enzyme, processes these dsRNA into 19-23 base pair short interfering RNAs with characteristic two base 3' overhangs. These siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. Thus, in one aspect the invention relates to a single stranded RNA (ssRNA) (the antisense strand of an siRNA duplex) generated within a cell and which promotes the formation of a RISC complex to effect silencing of the target gene. Accordingly, the term "siRNA" is also used herein to refer to an interfering RNA (i RNA).

In another aspect, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348, incorporated herein by reference for its technical disclosure, and in Lima et al., (2012) Cell 150: 883-894. Any of the RNAi agents described herein may be used as a single-stranded siRNA as described herein or as chemically modified by the methods described in Lima et al.

In another aspect, an "iRNA" or iRNA agent" for use in the compositions and methods described herein is a double stranded RNA and can be referred to herein as a "double stranded RNAi agent," "double stranded RNA (dsRNA) molecule," "dsRNA agent," or "dsRNA". The term "dsRNA", refers to a complex of ribonucleic acid molecules, having a duplex structure comprising two antiparallel and substantially complementary nucleic acid strands, referred to as having "sense" and "antisense" orientations with respect to a target RNA, e.g., an ALK mRNA. In some aspects, a double stranded RNA (dsRNA) triggers the degradation of a target RNA, e.g., an mRNA, through a post-transcriptional gene-silencing mechanism referred to herein as RNA interference or RNAi.

The majority of nucleotides of each strand of a dsRNA molecule may be ribonucleotides, but as described in detail herein, each or both strands can also include nucleotide analogs, where one or more non-ribonucleotides, e.g., a deoxyribonucleotide and/or a modified nucleotide. In addition, as used in this specification, an "RNAi agent" or "RNAi reagent" may include ribonucleotides with chemical modifications; an RNAi agent may include substantial modifications at multiple nucleotides. As used herein, the term "modified nucleotide" refers to a nucleotide having, independently, a modified sugar moiety, a modified inter-nucleotide linkage, and/or modified nucleobase. Thus, the term modified nucleotide encompasses substitutions, additions or removal of, e.g., a functional group or atom, to inter-nucleoside linkages, sugar moieties, or nucleobases. The modifications suitable for use in the reagents described herein include all types of modifications disclosed herein or known in the art. Any such modifications, as used in a siRNA type molecule, are encompassed by "RNAi agent" or "RNAi reagent" for the purposes of this disclosure.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some aspects, the hairpin loop can comprise at least 2, at least 3, at least 4, at least 5, at least 6, at least 7, at least 8, at least 9, at least 10, at least 20, at least 23, or more unpaired nucleotides. In some aspects, the hairpin loop can be 10 or fewer nucleotides. In some aspects, the hairpin loop can be 8 or fewer unpaired nucleotides. In some aspects, the hairpin loop can be 4-10 unpaired nucleotides. In some aspects, the hairpin loop can be 4-8 nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one aspect, an RNAi agent is a dsRNA, each strand of which comprises 19-23 nucleotides, that interacts with a target RNA sequence, e.g., an ALK mRNA, without wishing to be bound by theory, long double stranded RNA introduced into cells is broken down into siRNA by a Type III endonuclease known as Dicer. Dicer, a ribonuclease-III-like enzyme, processes the dsRNA into 19-23 base pair short interfering RNAs with characteristic two base 3' overhangs. The siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. In one aspect, an RNAi agent is a dsRNA of 24-30 nucleotides that interacts with a target RNA sequence, e.g., an ALK target mRNA sequence, to direct the cleavage of the target RNA.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one aspect of the dsRNA, at least one strand comprises a 3 ‘ overhang of at least 1 nucleotide. In another aspect, at least one strand comprises a 3’ overhang of at least 2 nucleotides, e.g., 2, 3, 4, 5, 6, 7, 9, 10, 11, 12, 13, 14, or 15 nucleotides. In other aspects, at least one strand of the RNAi agent comprises a 5' overhang of at least 1 nucleotide. In certain aspects, at least one strand comprises a 5' overhang of at least 2 nucleotides, e.g., 2, 3, 4, 5, 6, 7, 9, 10, 11, 12, 13, 14, or 15 nucleotides. In still other aspects, both the 3' and the 5' end of one strand of the RNAi agent comprise an overhang of at least 1 nucleotide.

In one aspect, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one aspect, the sense strand of a dsRNA has a 1-10 nucleotide, e.g., a 1, 2, 3, 4, 5, 6, 7, 8, 9, or 10 nucleotide, overhang at the 3'-end and/or the 5'-end. In certain aspects, the overhang on the sense strand or the antisense strand, or both, can include extended lengths longer than 10 nucleotides, e.g., 1-30 nucleotides, 2-30 nucleotides, 10-30 nucleotides, or 10-15 nucleotides in length. In certain aspects, an extended overhang is on the sense strand of the duplex. In certain aspects, an extended overhang is present on the 3 'end of the sense strand of the duplex. In certain aspects, an extended overhang is present on the 5 'end of the sense strand of the duplex. In certain aspects, an extended overhang is on the antisense strand of the duplex. In certain aspects, an extended overhang is present on the 3'end of the antisense strand of the duplex. In certain aspects, an extended overhang is present on the 5'end of the antisense strand of the duplex. In another aspect, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt.

Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double stranded over its entire length.

The term "antisense strand" or "guide strand" refers to the strand of an iRNA, e.g., a dsRNA, which includes a region that is substantially complementary to a target sequence, e.g., an ALK mRNA. As used herein, the term "region of complementarity" refers to the region on the antisense strand that is substantially complementary to a sequence, for example, a target sequence, e.g., an ALK mRNA sequence, e.g., as described herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand" or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some aspects, the cleavage region comprises three bases on either end of, and immediately adjacent to, the cleavage site. In some aspects, the cleavage region comprises two bases on either end of, and immediately adjacent to, the cleavage site. In some aspects, the cleavage site specifically occurs at the site bound by nucleotides 10 and 11 of the antisense strand, and the cleavage region comprises nucleotides 11, 12 and 13.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of a messenger RNA (mRNA)" refers to a polynucleotide that is substantially complementary to a contiguous portion of the mRNA of interest (e.g., an ALK mRNA).

Accordingly, in some aspects, the antisense strand polynucleotides disclosed herein are fully complementary to the target ALK mRNA sequence. In other aspects, the antisense strand polynucleotides disclosed herein are substantially complementary to the target ALK mRNA sequence and comprise a contiguous nucleotide sequence which is at least about 80% complementary over its entire length to the equivalent region of the nucleotide sequence of SEQ ID NO: 1, or a fragment thereof, such as about 85%, about 86%, about 87%, about 88%, about 89%, about 90%, about 91%, about 92%, about 93%, about 94%, about 95%, about 96%, about 97%, about 98%, or about 99% complementary.

It is understood that the sequence of the ALK mRNA must be sufficiently complementary to the antisense strand of the iRNA agent for the agent to be used in the indicated patient, e.g. human, mammalian, or vertebrate species.

The term "inhibiting," as used herein, is used interchangeably with "reducing," "silencing," "downregulating," "suppressing", "knocking down", and other similar terms, and includes any level of inhibition.

"Inhibiting expression of a ALK mRNA" includes any level of inhibition of an ALK mRNA, e.g., at least partial suppression of the expression of an ALK mRNA, such as an inhibition by at least about 20%. In certain aspects, inhibition is by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of an ALK may be assessed based on the level of any variable associated with ALK mRNA expression, e.g., ALK mRNA level or ALK protein level. The expression of an ALK mRNA may also be assessed indirectly based on assay of physiological markers associated with decreased expression of the ALK mRNA in a patient, such as type I IFN levels.

In one aspect, at least partial suppression of the expression of an ALK mRNA is assessed by a reduction of the amount of ALK mRNA that can be isolated from or detected in a cell or group of cells in which ALK is expressed. A reduction of the amount of ALK mRNA in a cell or tissue in which an ALK gene is transcribed and which has been treated such that the expression of an ALK mRNA is inhibited, is determined as compared to a second cell or tissue substantially identical to the first cell or tissue but which has not been so treated (control cells). The degree of inhibition may be expressed in terms of:

$$\left.\frac{(mRNA \text{ in control cells}) - (mRNA \text{ in treated cells})}{(mRNA \text{ in control cells})} \times 100\%\right)$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one aspect, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Patent Application Publication No. 2005/0281781, the technical disclosure of which are hereby incorporated herein by reference. In vitro introduction into a cell includes methods known in the art such as electroporation and lipofection. Further approaches are described herein below and/or are known in the art.

As used herein, and further to the discussion above regarding iRNA reagents, "agent" or "iRNA agent", when used in the context of an antisense, RNAi, or ribozyme, or other single-stranded or double-stranded RNA interfering nucleic acids, refers not only to RNA structures, but effective nucleic acid analog structures. In antisense and RNAi technologies, use of RNA poses significant delivery issues due to the lability of RNA molecules. As such, RNA is commonly chemically-modified to produce nucleic acid analogs, not only to enhance stability of the nucleic acid molecules, but often resulting in increased binding affinity, and with reduced toxicity. Such modifications are broadly-known to those of ordinary skill in the art, and are available commercially (see, e.g., Corey, D. R., Chemical modification: the key to clinical application of RNA interference? (2007) J Clin Invest.117(12):3615-3622, also describing RNAi, and United States Patent Application Publication No. 2017/0081667, incorporated herein by reference for its technical disclosure). Non-limiting examples of modifications to the nucleic acid structure in nucleic acid analogs include: modifications to the phosphate linkage, such as phosphoramidates or phosphorothioates; sugar modification, such as 2'-O, 4'-C methylene bridged, locked nucleic acid (LNA), 2'-methoxy, 2'-O-methoxyethyl (MOE), 2'-fluoro, S-constrained-ethyl (cEt), and tricyclo-DNA (tc-DNA); and non-ribose structures, such as phosphorodiamidate morpholino (PMO) and peptide-nucleic acids (PNA).

In addition to ALK RNAi agents described herein, antisense reagents (ASOs), other RNAi agents, ribozyme reagents, and other nucleic acid-based methods of reducing gene expression, can be designed and tested based on known sequences of ALK mRNAs and gene structure (exemplary sequences are provided herein and the ALK gene is well-studied). Based on the present disclosure, one of ordinary skill can design, and/or produce an active agent capable of knocking down ALK expression. Of note, a number of publications describe algorithms for generating candidate iRNA sequences, and publically-available software can be used to implement those algorithms. As such, typically, one only needs to enter an mRNA sequence into a calculator to produce candidate iRNAs.

Disclosed in WO 2016/209862, incorporated herein by reference for its technical description of RNAi agents, are details relating to iRNA structure, definition of required sequences and reagent size, definitions and descriptions of target sequences, methods of making iRNAs, variations or modifications in iRNA structures, such as nucleic acid analogs or mimetics, methods of modification of iRNAs such as ligand-modified iRNAs, including polysaccharide-modified or polypeptide-modified iRNAs and linkers that can be useful in targeting the iRNA, pharmaceutical compositions for delivery of iRNAs, delivery methods and delivery routes for iRNAs, including liposome or micellar delivery systems, and methods of determining whether iRNAs are effective. One of ordinary skill can identify and optimize ALK RNAi agents based on available knowledge and resources. Further disclosure herein of how to identify, make, or use ALK RNAi agents is unnecessary.

Conditions amenable to treatment by blocking or down-regulating a Type 1 IFN response (e.g., IFN-β) include, without limitation: sepsis; inflammatory bowel disease; rheumatoid arthritis; familial mediterranean fever (FMF); pyogenic arthritis; pyoderma gangrenosum; acne (PAPA); cryopyrin-associated periodic syndromes (CAPS); hyper IgD syndrome (HIDS); adult and juvenile Still disease; schnitzler syndrome; TNF receptor-associated periodic syndrome (TRAPS); Blau syndrome; Sweet syndrome; deficiency in IL-1 receptor antagonist (DIRA); recurrent idiopathic pericarditis; macrophage activation syndrome (MAS); urticarial vasculitis; antisynthetase syndrome; relapsing chondritis; Behget disease; Erdheim-Chester syndrome (histiocytosis); synovitis, acne, pustulosis, hyperostosis, osteitis (SAPHO); rheumatoid arthritis; periodic fever; aphthous stomatitis; pharyngitis; adenitis syndrome (PFAPA); urate crystal arthritis (gout); Type 2 diabetes; smoldering multiple myeloma; postmyocardial infarction heart failure; osteoarthritis; skin inflammation; inflammation associated with an infectious disease, such as inflammation associated with a viral infection, such as lung damage associated with influenza (see, e.g., Danarello, Calif., Interleukin-1 in the pathogenesis and treatment of inflammatory diseases, *Blood.* 2011 Apr. 7; 117(14): 3720-373) and Jensen, L E, Targeting the IL-1 family members in skin inflammation, *Curr Opin Investig Drugs.* 2010 November; 11(11): 1211-1220).

A more complete exemplary list of inflammatory diseases and conditions mediated by the inflammatory cytokine cascade (e.g., IFNα, IFNβ, TNF, and IL-6), include the following; grouped in disease categories: systemic inflammatory response syndrome, which includes sepsis syndrome, such as: gram positive sepsis, gram negative sepsis, culture negative sepsis, fungal sepsis, neutropenic fever, or urosepsis; meningococcemia; trauma hemorrhage; ionizing radiation exposure; acute pancreatitis; adult respiratory distress syndrome (ARDS); reperfusion injury, which includes: post-pump syndrome or ischemia-reperfusion injury; cardiovascular disease, which includes: cardiac stun syndrome, myocardial infarction, or congestive heart failure; infectious disease, which includes: hiv infection/hiv neuropathy, meningitis, hepatitis, septic arthritis, peritonitis, pneumonia epiglottitis, or *E. coli* 0157:H7; hemolytic uremic syndromic/thrombolytic thrombocytopenic purpura; malaria; dengue hemorrhagic fever; leishmaniasis; leprosy; toxic shock syndrome; streptococcal myositis; gas gangrene; *Mycobacterium tuberculosis; Mycobacterium avium intracellulare; Pneumocystis carinii* pneumonia; pelvic inflammatory disease; orchitis/epidydimitis; *Legionella*; lyme disease; influenza A; Epstein-Barr virus; viral associated hemiaphagocytic syndrome; viral encephalitis/aseptic meningitis; obstetric or gynecological conditions, including: premature labor, miscarriage, or infertility; inflammatory disease or autoimmune conditions, which includes: rheumatoid arthritis/seronegative arthropathies, osteoarthritis, inflammatory bowel disease, systemic lupus erythematosis, iridoeyelitis/uveitistoptic neuritis, idiopathic pulmonary fibrosis, systemic vasculitis/Wegener's gramilornatosis, sarcoidosis, or orchitis/vasectomy reversal procedures; allergic/atopic diseases, which includes: asthma, allergic rhinitis, eczema, allergic contact dermatitis, allergic conjunctivitis, or hypersensitivity pneumonitis; transplant-related conditions, including: organ transplant rejection or graft-versus-host disease; cachexia; congenital conditions, which include: cystic fibrosis, familial hematophagocytic lymphohistiocytosis or sickle cell anemia; dermatologic conditions, which includes: psoriasis and alopecia; neurologic, which includes: multiple sclerosis and migraine headache; renal conditions, which includes: nephrotic syndrome, hermodialysis, and uremia; toxicity, which includes: OKT3 therapy, anti-CD3 therapy, cytokine therapy, chemotherapy, radiation therapy, or chronic salicylate intoxication; or metabolic/idiopathic conditions, which include: wilson's disease, hemachromatosis, alpha-1 antitrypsin deficiency, diabetes, Hashimoto's thyroiditis, osteoporosis, hypothalamic-pituitary-adrenal axis evaluation, or primary biliary cirrhosis.

In one aspect, the method of reducing a Type I IFN response, e.g., a proinflammatory Type I IFN response is provided. In another aspect, a method of treating an inflammatory disease or condition, such as sepsis, is provided. The method comprise downregulation of anaplastic lymphoma kinase (ALK) expression or activity in a patient. By downregulating ALK in such patients, the Type I IFN response, and therefore inflammation, is downregulated. In one aspect, an ALK inhibitor is administered to a patient in an amount effective to decrease a Type I IFN response or a stimulator of interferon genes (STING) response in a patient. A type I interferon response results in, inter alia, the production of a type I IFN. By reducing a STING response, a type I IFN response is inhibited and therefore production of type I IFNs (e.g. IFN-α or IFN-β, or, IFN-ε, IFN-κ, IFN-τ, IFN-δ, IFN-ζ, IFN-ω, or IFN-υ) are reduced. In another aspect, ALK expression is knocked down, e.g., by a RNAi agent or by an antisense agent directed to the ALK mRNA.

A "kinase inhibitor" is a compound or composition that decreases kinase expression and/or activity, with the overall effect of decreasing kinase activity in a cell, tissue, or patient. Kinase inhibitors are a recognized class of pharmaceutical active agents. An "ALK inhibitor" is a compound or composition that decreases ALK expression and/or activity, with the overall effect of decreasing ALK activity in a cell, tissue, or patient. ALK inhibitors are a recognized class of pharmaceutical active agents. As described herein, the kinase inhibitors or ALK inhibitors are chosen for their ability to decrease production of a Type I IFN response in a patient suffering from an inflammatory disease, such as sepsis. In the Example below, kinase inhibitors, including ALK inhibitors, were evaluated for their ability to downregulate a STING response, and therefore a Type I IFN response. The following listed compounds have the ability to decrease IFN-β release in the described assay, with some exhibiting decreases of over 5% (less than a 0.95-fold increase in IFN-β release); over 25% (less than a 0.75-fold increase in IFN-β release); over 50% (less than a 0.50-fold increase in IFN-β release); over 75% (less than a 0.25-fold increase in IFN-β release); over 80% (less than a 0.20-fold increase in IFN-β release); over 85% (less than a 0.15-fold increase in IFN-β release); and over 90% (less than a 0.10-fold increase in IFN-β release). Structures for the following compounds are provided in priority U.S. Provisional Patent Application No. 62/594,162 filed Dec. 4, 2017, and U.S. Provisional Patent Application No. 62/608,835 filed Dec. 21, 2017, both of which are incorporated herein by reference in their entirety Non-limiting examples of target compounds exhibiting at least a 25% reduction of IFN-β release include (compound (description of compound action, —fold increase in IFN-β release)): N6022 (an inhibitor of S-nitrosoglutathione reductase, 0.75); SU11274 (a selective Met inhibitor, 0.75); Nebivolol (an inhibitor of β1-adrenoceptor, 0.75); GW3965 HCl (an LXR agonist for hLXRα and hLXRβ, 0.74); Sodium 4-Aminosalicylate (an antibiotic used to treat tuberculosis via NF-κB inhibition and free radical scavenging, 0.74); CNX-774 (an irreversible, orally active, and highly selective BTK inhibitor, 0.73); Temsirolimus (CCI-779, NSC 683864) (a specific mTOR inhibitor, 0.73); FG-4592 (an HIF-α prolyl hydroxylase inhibitor, 0.73); NMS-P937 (NMS1286937) (an orally available, selective PLK1 inhibitor, 0.73); Loxistatin Acid (E-64C) (an irreversible and membrane-permeant cysteine protease inhibitor, 0.70); Belinostat (PXD101) (an HDAC inhibitor, 0.70); Bisoprolol fumarate (a selective type β1 adrenergic receptor blocker, 0.70); U0126-EtOH (a highly selective inhibitor of MEK1/2, 0.70); Felodipine (a selective L-type $Ca^{2+}$ channel blocker, 0.69); Doxazosin Mesylate (a quinazoline-derivative, selectively antagonizes postsynaptic α1-adrenergic receptors, 0.69); BTZ043 Racemate (a decaprenylphosphoryl-β-D-ribose 2'-epimerase inhibitor, 0.69); ZM 447439 (a selective and ATP-competitive inhibitor for Aurora A and Aurora B, 0.69); Fostamatinib (R788) (a Syk inhibitor, 0.69); Mirabegron (a selective β3-adrenoceptor agonist, 0.69); PFK15 (a potent and selective 6-phosphofructo-2-kinase inhibitor, 0.68); Methotrexate (a nonspecific inhibitor of the dihydrofolate reductase, 0.68); OSI-906 (Linsitinib) (a selective inhibitor of IGF-1R, 0.66); Veliparib (ABT-888) (a potent inhibitor of PARP1 and PARP2, 0.66); Tandutinib (MLN518) (a potent FLT3 antagonist, 0.65); SGI-1776 free base (an ATP competitive inhibitor of Pim1, 0.65); SB742457 (a highly selective 5-HT6 receptor antagonist, 0.65); Refametinib (RDEA119 (Bay 86-9766) (a potent, ATP non-competitive and highly selective inhibitor of MEK1 and MEK2, 0.64); PluriSln #1 (NSC 14613) (an inhibitor of the stearoyl-coA desaturase 1, 0.62); Panobinostat (LBH589) (a broad-spectrum HDAC inhibitor, 0.61); NVP-ADW742 (an IGF-1R inhibitor, 0.61); Letrozole (a third generation inhibitor of aromatase, 0.61); PI-1840 (a reversible and selective chymotrypsin-like inhibitor, 0.60); Vemurafenib (PLX4032 (RG7204) (an inhibitor of B-Raf$^{V600E}$, 0.59); ML133 HCl (a selective potassium channel inhibitor, 0.59); KPT-185 (a selective CRM1 inhibitor, 0.59); Sotrastaurin (a potent and selective pan-PKC inhibitor, 0.59); Ridaforolimus (Deforolimus (MK-8669) (a selective mTOR inhibitor, 0.58); Empagliflozin (BI 10773) (a potent and selective SGLT-2 inhibitor, 0.57); Bergenin (a trihydroxybenzoic acid glycoside and the C-glycoside of 4-O-methyl gallic acid, 0.57); Icotinib (an EGFR inhibitor, 0.57); Mubritinib (TAK 165) (a potent inhibitor of HER2/ErbB2, 0.56); GNF-2 (a highly selective non-ATP competitive inhibitor of Bcr-Abl, 0.56); Ramelteon (a melatonin receptor agonist for human MT1 and MT2 receptors and chick forebrain melatonin receptors, 0.56); Cinacalcet HCl (a new class of compounds for the treatment of hyperparathyroidism, 0.55); Rotundine (a selective dopamine D1 receptor antagonist, 0.54); Rivaroxaban (a direct inhibitor of Factor Xa, 0.54); CGP 57380 (a potent MNK1 inhibitor, 0.54); KPT-276 (an orally bioavailable selective CRM1 inhibitor, 0.54); Ibrutinib (PCI-32765) (a potent and highly selective Brutons tyrosine kinase (Btk) inhibitor, 0.53); Tenovin-6 (a small molecule activator of p53 transcriptional activity, 0.53); JNK Inhibitor IX (a selective and potent JNK inhibitor, 0.53); HO-3867 (a selective STAT3 inhibitor, 0.52); PFI-1 (PF-6405761) (a highly selective bromodomain-containing protein inhibitor for BRD4, 0.52); Fulvestrant (an estrogen receptor antagonist, 0.52); BAPTA-AM (a selective, membrane-permeable calcium chelator, 0.52); NSC697923 (a cell-permeable and selective inhibitor of the Ub-conjugating enzyme (E2) complex Ubc13-Uev1A, 0.51); Dutasteride (a dual 5-α reductase inhibitor that inhibits conversion of testosterone to dihydrotestosterone, 0.51); Irinotecan HCl Trihydrate (an inhibitor of topoisomerase 1, 0.51); Ki16198 (a LPA antagonist and inhibits LPA1- and LPA3-induced inositol phosphate production, 0.51); Enzalutamide (MDV3100) (an androgen-receptor (AR) antagonist, 0.50); Selumetinib (AZD6244) (a potent, highly selective MEK1 inhibitor, 0.50); SKI II (a highly selective and non ATP-competitive sphingosine kinase inhibitor, 0.49); SB-3CT (an effective and selective gelatinase inhibitor, 0.49); TCS 359 (a potent FLT3 inhibitor, 0.45); AZD7762 (a potent and selective inhibitor of Chk1, 0.45); BI 2536 (a potent Plk1 inhibitor 0.45); VE-821 (a potent and selective ATP competitive inhibitor of ATR, 0.45); HA14-1 (a non-peptidic ligand of a Bcl-2 surface pocket, 0.45); Apigenin (a potent P450 inhibitor for CYP2C9, 0.44); IOX2 (potent inhibitor of HIF-1a prolyl hydroxylase-2, 0.44); Caffeic Acid Phenethyl Ester (a potent and specific inhibitor of NF-κB activation 0.44); ML323 (an inhibitor of USP1/UAF1 0.43); PHA-665752 (a potent, selective and ATP-competitive c-Met inhibitor, 0.43); OTX015 (a potent BET bromodomain inhibitor, 0.43); MK-8245 (an liver-targeting inhibitor of stearoyl-CoA desaturase, 0.42); Bupivacaine HCl (an inhibitor of intracellular portion of voltage-gated sodium channels, 0.42); Piceatannol (a natural stilbene, is a selective Syk inhibitor, 0.42); I-BET151 (GSK1210151A) (a novel selective BET inhibitor for BRD2, BRD3 and BRD4, 0.40); GSK J4 HCl (a selective inhibitor of the H3K27 histone demethylase JMJD3 and UTX 0.40); PD0325901 (a selective and non ATP-competitive MEK inhibitor, 0.39); Trichostatin A (TSA) (an HDAC inhibitor, 0.39); Costunolide (an inhibitor of FPTase, 0.37); SGI-1027 (a DNMT inhibitor, 0.37); Bortezomib (PS-341) (a potent 20S proteasome inhibitor, 0.37); AZD4547 (a novel selective FGFR inhibitor, 0.35); IPA-3 (a selective non-ATP competitive Pak1 inhibitor, 0.35); BML-190 (a selective cannabinoid CB2 receptor inverse agonist, 0.35); P22077 (an inhibitor of ubiquitin-specific protease USP7, 0.35); TWS119 (a GSK-3β inhibitor, 0.35); SB203580 (a p38 MAPK inhibitor, 0.35); Etodolac (a COX inhibitor, 0.35); LDN-212854 (a potent and selective BMP receptor inhibitor, 0.33); KU-55933 (a potent and specific ATM inhibitor, 0.33); Fluvastatin Sodium (an inhibitor of HMG-CoA reductase activity, 0.32); Crenolanib (CP-868596) (a potent and selective inhibitor of PDGFRα/β, 0.32); VS-5584 (SB2343) (a potent and selective dual PI3K/mTOR inhibitor for mTOR and PI3Kα/β/δ/γ, 0.32); SB705498 (a TRPV1 antagonist for hTRPV1, antagonizes capsaicin, acid, and heat activation of TRPV1, 0.32); AZ20 (a novel potent and selective inhibitor of ATR kinase, 0.32); OSU-03012 (AR-12) (a potent inhibitor of recombinant PDK-1, 0.31); Aloxistatin (an irreversible and membrane-permeable cysteine protease inhibitor with blood platelet aggregation inhibiting activity, 0.31); Trimebutine (an agonist of peripheral mu, kappa and delta opiate receptors, 0.30); YM155 (Sepantronium Bromide) (a potent survivin suppressant by inhibiting Survivin promoter activity, 0.30); Alvelestat (AZD9668) (an oral, highly selective inhibitor of neutrophil elastase, 0.27); PTC-209 HBr (a potent and selective BMI-1 inhibitor, 0.27); CP-673451 (a selective inhibitor of PDGFRα/β, 0.27); XL335 (a potent, selective FXR agonist, 0.26); MNS (3 (4-Methylenedioxy-β-nitrostyrene (MDBN) (a tyrosine kinase inhibitor, 0.26); Apatinib (an orally bioavailable, selective VEGFR2 inhibitor, 0.26); Go 6983 (a pan-PKC inhibitor against for PKCα, PKCβ, PKCγ and PKCδ, 0.26); LY411575 (a potent γ-secretase inhibitor, 0.26); Sirtinol (a specific SIRT1 and SIRT2 inhibitor, 0.26); HSP990 (NVP-HSP990) (a potent and selective HSP90 inhibitor for HSP90α/β, 0.26); Vandetanib (ZD6474) (a potent inhibitor of VEGFR2, 0.25); Iniparib (BSI-201) (a PARP1 inhibitor with demonstrated effectiveness in triple-negative breast cancer, 0.23); Sertraline HCl (a 5-HT antagonist, 0.22); GSK461364 (an inhibitor of Plk1, 0.21); PF-562271 (a potent, ATP-competitive, reversible inhibitor of FAK, 0.21); Ruxolitinib (INCB018424) (a potent, selective, JAK1/2 inhibitor 0.20); Toremifene Citrate (an oral selective estrogen receptor modulator, 0.19); AP26113 (a potent and selective ALK inhibitor, 0.19); Sal003 (a potent and cell-permeable eIF-2α phosphatase inhibitor, 0.18); PAC-1 (a potent procaspase-3 activator, 0.17); Embelin (an inhibitor of X-linked inhibitor of apoptosis, 0.17); E-64 (an irreversible and selective cysteine protease inhibitor, 0.17); Cryptotanshinone (a STAT3 inhibitor, 0.17); Apoptosis Activator 2 (an inducer of caspase-3 activation, PARP cleavage, and DNA fragmentation, 0.17); AVL-292 (a covalent, orally active, and highly selective BTK inhibitor, 0.16); PF-5274857 (a potent and selective Smoothened antagonist, 0.16); CG11746 (a potent and highly selective small-molecule inhibitor of the Btk, 0.16); (−)-Parthenolide (an inhibitor of the Nuclear Factor-κB pathway, 0.16); Pifithrin-μ (a specific p53 inhibitor, 0.16); Bazedoxifene HCl (a novel, non-steroidal, indole-based estrogen receptor modulator (SERM) binding to both ERα and ERβ, 0.15); CP-91149 (a selective glycogen phosphorylase inhibitor, 0.14); PP2 (a Src family kinase inhibitor, 0.14); OSI-420 (an EGFR inhibitor, 0.14); ZM 306416 (a VEGFR (Flt and KDR) inhibitor for VEGFR1, 0.14); Dalcetrapib (JTT-705 (RO4607381) (a rhCETP inhibitor, 0.13); Wnt-059 (C59) (a PORCN inhibitor, 0.13); AT101 (the R-(−) enantiomer of Gossypol acetic acid, binds with Bcl-2, Bcl-xL and Mcl-1, 0.13); (+)-JQ1 (a BET bromodomain inhibitor, 0.13); GW0742 (a potent and highly selective PPARβ/δ agonist, 0.13); PNU-120596 (a positive allosteric modulator of α7 nAChR, 0.12); WZ4003 (a highly specific NUAK kinase inhibitor, 0.12); NH125 (a selective eEF-2 kinase inhibitor, 0.11); Ozagrel (a selective thromboxane A2 synthetase inhibitor, 0.11); Daunorubicin HCl (an inhibitor of DNA synthesis, 0.11); Isotretinoin (a chemotherapy medication for the treatment of brain cancer, pancreatic cancer, 0.10); ICG-001 (an Wnt/β-catenin/TCF-mediated transcription antagonists, 0.10); Ospemifene (a non-hormonal selective estrogen receptor modulator, 0.10); AZ 3146 (a selective Mps1 inhibitor, 0.10); Stattic (an inhibitor of STAT3 activation, 0.10); LDK378 (an inhibitor of ALK, 0.08); PRT062607 (P505-15 (B1113057) HCl (a highly selective Syk inhibitor, 0.07); KU-60019 (an ATM inhibitor, 0.06); AZD3463 (an orally bioavailable ALK inhibitor, 0.05); and KPT-330 (an orally bioavailable selective CRM1 inhibitor, 0.05).

Exemplary ALK inhibitors include, without limitation: LDK378 (ceritinib or ZYKADIA®), crizotinib, alectinib, AP26113, ASP3026, and TSR-011. Additional ALK inhibitors include dalantercept, brigatinib, entrectinib, PF-06463922, CEP-37440, TAE684 (NVP-TAE684), Alectinib (CH5424802), GSK1838705A, AZD3463, TPX-0005, Lorlatinib (PF-6463922, LORBRENA®), ML347, Ensartinib (X-396), and X-396 (see Appendix A for structures). Patent publications WO 2008/073687 and US 20170281624 disclose ALK inhibitors and methods of making the ALK inhibitors, such as LDK378 (5-chloro-$N^2$-(2-isopropoxy-5-methyl-4-(piperidin-4-yl)phenyl)-$N^4$-[2-(propane-2-sulfonyl)-phenyl]-pyrimidine-2,4-diamine).

In one aspect, the ALK inhibitor is lorlatinib (e.g., (10R)-7-Amino-12-fluoro-2,10,16-trimethyl-15-oxo-10,15,16,17-tetrahydro-2H-4,8-methenopyrazolo[4,3-h][2,5,11]benzoxadiazacyclotetradecine-3-carbonitrile). In another, the ALK inhibitor is an ALK inhibitor described in U.S. Pat. No. 8,680,111, incorporated herein by reference for its disclosure of macrocyclic derivatives related to lorlatinib for treatment of cell proliferative disorders. See also, Unites States Patent Application Publication No. 2018/0235933 and International Patent Application Publication Nos. WO 2013/132376, WO 2014/207606, and WO 2017/175091, each of which is incorporated herein by reference for its disclosure of ALK inhibitors, and methods of making and using ALK inhibitors.

Pharmaceutically-acceptable salts or esters (e.g. prodrugs) of compounds described herein may find use in the methods provided herein. For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

Pharmaceutically acceptable acid and base addition salts as mentioned herein comprise therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g., hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely the salt forms can be converted by treatment with an appropriate base into the free base form.

Compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine and the like. The term "addition salt" as used hereinabove also comprises the solvates which the compounds described herein are able to form. Such solvates are for example hydrates, alcoholates and the like.

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and valyl.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form.

As used herein, unless indicated otherwise, for instance in a structure, all compounds and/or structures described herein comprise all possible stereoisomers, individually or mixtures thereof. The compound and/or structure may be an enantiopure preparation consisting essentially of an (−) or (+) enantiomer of the compound, or may be a mixture of enantiomers in either equal (racemic) or unequal proportions.

The compounds typically are administered in an amount and dosage regimen effective to decrease a type 1 IFN response in a patient, for example as is found in sepsis, or other inflammatory diseases or conditions. The compounds also are useful in reducing a STING response in a patient. For example, doses of LDK378 from 100 mg to 1000 mg, orally, daily, are expected to effectively decrease a Type I IFN response in a patient, for example to treat sepsis. The compounds may be administered in any manner that is effective to decrease a Type I IFN response, a STING response, or to treat, mitigate or prevent sepsis, or other inflammatory diseases or conditions. Examples of delivery routes include, without limitation: topical, for example, epicutaneous, inhalational, enema, ocular, otic and intranasal delivery; enteral, for example, orally, by gastric feeding tube and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral, intravenous, intramuscular and transdermal approaches being preferred in many instances.

An "effective amount" of the compound or composition described herein is an amount effective in a dosage regimen (amount of the compound and timing of delivery), to achieve a desired end-point, such as maintaining concentrations at a site of treatment within a range effective to achieve an outcome. Suitable outcomes include decrease a Type I IFN response, a STING response, or to treat, mitigate or prevent sepsis, or other inflammatory diseases or conditions.

A "therapeutically effective amount" refers to an amount of a drug product or active agent effective, at dosages and for periods of time necessary, to achieve the desired therapeutic result. An "amount effective" for treatment of a condition is an amount of an active agent or dosage form, such as a single dose or multiple doses, effective to achieve a determinable end-point. The "amount effective" is preferably safe—at least to the extent the benefits of treatment outweighs the detriments, and/or the detriments are acceptable to one of ordinary skill and/or to an appropriate regulatory agency, such as the U.S. Food and Drug Administration. A therapeutically effective amount of an active agent may vary according to factors such as the disease state, age, sex, and weight of the individual, and the ability of the active agent to elicit a desired response in the individual. A "prophylactically effective amount" refers to an amount effective, at dosages and for periods of time necessary, to achieve a desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc., be proportionally reduced or increased as indicated by the exigencies of the therapeutic situation. In some instances, it may be especially advantageous to formulate compositions, such as parenteral or inhaled compositions, in dosage unit form for ease of administration and uniformity of dosage. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Useful dosage forms include: intravenous, intramuscular, or intraperitoneal solutions, oral tablets or liquids, topical ointments or creams and transdermal devices (e.g., patches). In one aspect, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

Therapeutic/pharmaceutical compositions are prepared in accordance with acceptable pharmaceutical procedures, such as described in *Remington: The Science and Practice of Pharmacy,* 21st edition, ed. Paul Beringer et al., Lippincott, Williams & Wilkins, Baltimore, Md. Easton, Pa. (2005) (see, e.g., Chapters 37, 39, 41, 42 and 45 for examples of powder, liquid, parenteral, intravenous and oral solid formulations and methods of making such formulations).

Drug products, or pharmaceutical compositions comprising an active agent (e.g., drug), for example, an active agent that decreases ALK expression or activity, or ALK expression or activity may be prepared by any method known in the art of pharmacy, for example, by bringing into association the active ingredient with the carrier(s) or excipient(s). As used herein, a "pharmaceutically acceptable excipient", "carrier" or "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable excipients include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active agent. In certain aspects, the active compound may be prepared with a carrier that will protect the compound against rapid release, such as a controlled release formulation, including implants, transdermal patches, and microencapsulated delivery systems. Biodegradable, biocompatible polymers can be used in delivery systems, such as ethylene vinyl acetate, polyanhydrides, polyglycolic acid, collagen, polyorthoesters, and polylactic acid. Many methods for the preparation of such formulations are broadly-known to those skilled in the art.

Additionally, active agent-containing compositions may be in variety of forms. The preferred form depends on the intended mode of administration and therapeutic application, which will in turn dictate the types of carriers/excipients. Suitable forms include, but are not limited to, liquid, semi-solid and solid dosage forms.

Pharmaceutical formulations adapted for oral administration may be presented, for example and without limitation, as discrete units such as capsules or tablets; powders or granules; solutions or suspensions in aqueous or non-aqueous liquids; edible foams or whips; or oil-in-water liquid emulsions or water-in-oil liquid emulsions. In certain embodiments, the active agent may be contained in a formulation such that it is suitable for oral administration, for example, by combining the active agent with an inert diluent or an assimilable edible carrier. The active agent (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical formulations adapted for transdermal administration may be presented, for example and without limitation, as discrete patches intended to remain in intimate contact with the epidermis of the recipient for a prolonged period of time or electrodes for iontophoretic delivery.

Pharmaceutical formulations adapted for topical administration may be formulated, for example and without limitation, as ointments, creams, suspensions, lotions, powders, solutions, pastes, gels, sprays, aerosols or oils.

Pharmaceutical formulations adapted for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include, without limitation, fine particle dusts or mists which may be generated by means of various types of metered dose pressurized aerosols, nebulizers or insufflators. In the context of delivery of the active agents described herein by inhalation, inhalation drug products, such as metered-dose inhalers, as are broadly-known in the pharmaceutical arts, are used. Metered dose inhalers are configured to deliver a single dose of an active agent per actuation, though multiple actuations may be needed to effectively treat a given patient.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets.

Therapeutic compositions typically must be sterile and stable under the conditions of manufacture and storage. For example, sterile injectable solutions can be prepared by incorporating the active agent in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

As an example, the ALK inhibitor LDK378 may be administered at an oral dose of about 10-1000, e.g., 100 to 1000 mg, 150 mg to 900 mg, about 200 mg to 800 mg, about 300 mg to 700 mg, or about 400 mg to 600 mg, e.g., 150 mg, 300 mg, 450 mg, 600 mg or 750 mg. In aspects, LDK378 is administered with food. In other aspects, the dose is under fasting condition. The dosing schedule can vary from e.g., every other day to daily, twice or three times a day. In one aspect, LDK378 is administered daily. In one aspect, LDK378 is administered at an oral dose from about 150 mg to 750 mg daily, either with food or in a fasting condition. In one aspect, LDK378 is administered at an oral dose of about 750 mg daily, in a fasting condition. In one aspect, LDK378 is administered at an oral dose of about 750 mg daily, via capsule or tablet. In another aspect, LDK378 is administered at an oral dose of about 600 mg daily, via capsule or tablet. In one aspect, LDK378 is administered at an oral dose of about 450 mg daily, via capsule or tablet.

EXAMPLE

In the study below, we screened a library of 464 kinase inhibitors for STING-modulating capacities, and found that some inhibitors, e.g., those specific for anaplastic lymphoma kinase (ALK), displayed the strongest suppression of the STING-mediated type I interferon immune response in macrophages and monocytes. Evidence is provided to support a central role of ALK in the regulation of STING activation in monocytes and macrophages, which contribute to dysregulation of the innate immune response and pathogenesis of experimental and clinical sepsis. The second generation ALK inhibitor LDK378, an FDA-approved oral anticancer drug, exhibited promising anti-inflammatory activity in animal models of lethal sepsis, and the ALK pathway was upregulated in patients with sepsis. The data below indicate a paradigm for how host innate immunity is regulated through the ALK signaling pathway in innate immune cells and suggest ALK inhibitors could be potential therapeutic agents for lethal systemic inflammatory diseases.

The objective of this example was to identify potential drugs targeting the STING pathway for the treatment of sepsis. Through a kinase inhibitors library screen, we identified ALK inhibitors as the top inhibitors for STING activation in monocytes and macrophages. We next defined the molecular mechanism by which ALK promotes STING activation through EGFR and AKT. We also evaluated the efficacy of ALK-targeting strategies for the management of polymicrobial sepsis and lethal endotoxemia in mice.

Finally, we determined whether the ALK-STING pathway is similarly altered in the PBMCs of patients with sepsis. In all experiments, animals were randomized to different treatment groups without blinding. Sample size in experiments was specified in each figure legend. We did not exclude samples or animals. For every figure, statistical tests are justified as appropriate. All data meet the assumptions of the tests. No statistical methods were used to pre-determine sample sizes, but our sample sizes are similar to those generally employed in the field.

Materials and Methods

Animal models of endotoxemia and sepsis: C57BL/6J wild-type mice (#000664) and STING−/− mice (strain name: C57BL/6J-Tmem173$^{gt}$/J, #017537) were purchased from The Jackson Laboratory. Mice were housed with their littermates in groups of four animals per cage and kept on a regular 12 hr light and dark cycle (7:00-19:00 light period). Food and water were available ad libitum. Experiments were carried out under pathogen-free conditions and the health status of mouse lines was routinely checked by veterinary staff. Experiments were carried out with randomly chosen littermates of the same sex and matched age and body weight. Reagents are listed in Table 1. Unless indicated to the contrary, all nucleotide sequences are recited in a 5' to 3' direction, and all amino acid sequences are recited in an N-terminal to C-terminal direction.

Antibodies:

Rabbit monoclonal anti-STING (Cell Signaling Technology, Cat #13647S), Rabbit polyclonal anti-phospho-STING (Ser366) (Cell Signaling Technology, Cat #857355), Rabbit polyclonal anti-IRF-3 (Cell Signaling Technology, Cat #49625; RRID:AB_2272318), Rabbit monoclonal anti-phospho-TBK1/NAK (Ser172) (Cell Signaling Technology, Cat #54835; RRID:AB_10695239), Rabbit monoclonal anti-TBK1/NAK (Cell Signaling Technology, Cat #35045; RRID:AB_2255663), Rabbit monoclonal anti-phospho-IRF3 (Ser396) (Cell Signaling Technology, Cat #49475; RRID:AB_823547), Rabbit monoclonal anti-NF-κB p65 (Cell Signaling Technology, Cat #82425; RRID: AB_10859369), Rabbit monoclonal anti-phospho-NF-κB p65 (Ser536) (Cell Signaling Technology, Cat #30335; RRID:AB_331284), Rabbit polyclonal anti-EGF Receptor (Cell Signaling Technology, Cat #22325; RRID: AB_823483), Rabbit monoclonal anti-phospho-EGF Receptor (Tyr1068) (Cell Signaling Technology, Cat #37775; RRID:AB_2277657), Rabbit monoclonal anti-Akt (pan) (Cell Signaling Technology, Cat #4691S; RRID: AB_915783), Rabbit monoclonal cPhospho-Akt (Ser473) (Cell Signaling Technology, Cat #40605; RRID: AB_2315049), Mouse monoclonal anti-S6 Ribosomal Protein (Cell Signaling Technology, Cat #23175; RRID: AB_2238583), Mouse monoclonal anti-ALK (Santa Cruz Biotechnology, Cat #sc-398791), Rabbit polyclonal anti-phospho-ALK (Y1507) (Abcam, Cat #ab192809), Mouse monoclonal anti-beta-Actin (Sigma, Cat # A2228; RRID: AB_476697), and Goat polyclonal anti-TICAM-1/TRIF (Boster, Cat # A01872).

Chemicals, Peptides, and Recombinant Proteins:

Target-selective Inhibitory Library (Selleck Chemicals, Cat # L3500), ALK inhibitor (LDK378, ceritinib) (Selleck Chemicals, Cat # S7083), ALK inhibitor (Ap26113) (Selleck Chemicals, Cat # S7000), EGFR inhibitor (OSI-420) (Selleck Chemicals, Cat # S2205), AKT inhibitor (GDC-0068) (Selleck Chemicals, Cat # S2808), 3'3'-cGAMP (InvivoGen, Cat # tlrl-nacga33), 2'3'-cGAMP (InvivoGen, Cat # tlrl-nacga23), 2'2'-cGAMP (InvivoGen, Cat # tlrl-nacga22), c-di-AMP (InvivoGen, Cat # tlrl-nacda), c-di-GMP (InvivoGen, Cat # tlrl-nacdg), c-di-IMP (InvivoGen, Cat # tlrl-nacdi), and DMXAA (InvivoGen, Cat # tlrl-dmx Critical Commercial Assays:

Human IFN-beta ELISA kit (Fisher Scientific, Cat #414101), Mouse IFN-beta ELISA kit (BioLegend, Cat #439408), Proteome Profiler Mouse Cytokine Array (R&D, Cat # ARY028), Proteome Profiler Mouse phosphor-RTK Array (R&D, Cat # ARY014), CK single-slide test (IDEXX, Cat #98-11073-01), AMYL single-slide test (IDEXX, Cat #98-11068-01), BUN single-slide test (IDEXX, Cat #98-11070-01), and ALT single-slide test (IDEXX, Cat #98-11067-01).

Cell Lines:

Mouse: iBMDMs (Laboratory of Kate Fitzgerald), Mouse: RAW264.7 (ATCC, Cat #TIB-71), Mouse: J774A.1 (ATCC, Cat # TIB-67), Human: THP-1 (ATCC, Cat # TIB-202), and Human: PBMCs (LifeLine Cell Technology, Cat #1207).

Mice:

Mouse: C57BL/6J-Tmem173$^{gt}$/J (The Jackson Laboratory, Stock #: 017537), and Mouse: C57BL/6J (The Jackson Laboratory, Stock #: 000664).

Sequence-Based Reagents:

shRNA targeting sequencing: ALK for mouse #1; CCGGGCTGGAAGAATAGCAAAGAT-TCTCGAGAATCTTTGCTATTCTTCCAGC TTTTT (SEQ ID NO: 5)(Sigma, Clone ID: TRCN0000023724), shRNA targeting sequencing: ALK for mouse #2; CCGGCGGAG-GATATATAGGTGGCAACTCGAGTTGCCACC-TATATATCCTCC GTTTTT (SEQ ID NO: 6) (Sigma, Clone ID: TRCN0000023726), shRNA targeting sequencing: ALK for human #1; CCGGGTGATAAATACAAGGCCCA-GACTCGAGTCTGGGCCTTGTATTTATCA CTTTTT (SEQ ID NO: 3) (Sigma, Clone ID: TRCN0000000784), shRNA targeting sequencing: ALK for human #2; CCG-GAGAAGAAGAAATCCGTGTGAACTCGAGTT-CACACGGATTTCTTCTTCT TTTTT (SEQ ID NO: 4) (Sigma, Clone ID: TRCN0000000787), shRNA targeting sequencing: EGFR for mouse #1; CCGGGCTGGATGATA-GATGCTGATACTCGAGTATCAGCATCTATCATCCAG CTTTTTG (SEQ ID NO: 7) (Sigma, Clone ID: TRCN0000055218), shRNA targeting sequencing: EGFR for mouse #2; CCGGGCCTATCAAGTGGATGG CTTTCTCGAGAAAGCCATCCACTTGA-TAGGCTTTTTG (SEQ ID NO: 8) (Sigma, Clone ID: TRCN0000055221), shRNA targeting sequencing: EGFR for human #1; CCGGGCCTATCAAGTGGATGGCAT-TCTCGAGAATGCCATCCACTTGATAGG CTTTTTG (SEQ ID NO: 9) (Sigma, Clone ID: TRCN0000199532), shRNA targeting sequencing: EGFR for human #2; CCGGCCAAGCTCTCTTGAGGATCTTCTCGAGAA-GATCCTCAAGAGAGCTTG GTTTTTG (SEQ ID NO: 10) (Sigma, Clone ID: TRCN0000199174), shRNA targeting sequencing: negative control (Sigma, Clone ID: SHC016V), Primers: mouse-ifnb-Fwd: 5'-GCCTTTGC-CATCCAAGAGATGC-3' (SEQ ID NO: 11) and Rev: 5'-ACACTGTCTGCTGGTGGAGTTC-3' (SEQ ID NO: 12) (Sigma, N/A), Primers: human-ifnb-Fwd: 5'-AAACTCAT-GAGCAGTCTGCA-3' (SEQ ID NO: 13) and Rev: 5'-AG-GAGATCTTCAGTTTCGGAGG-3' (SEQ ID NO: 14) (Sigma, N/A), Primers: mouse-tnfa-Fwd: 5'-GGTGCC-TATG TCTCAGCCTCTT-3' (SEQ ID NO: 15) and Rev: 5'-GCCATAGAACTGATGAGAGGGAG-3' (SEQ ID NO: 16) (Sigma, N/A), Primers: mouse-117-Fwd: 5'-CAG-GAACTGATAGTAATTGCCCG-3' (SEQ ID NO: 17) and Rev: 5'-CTTCAACTTGCGAGCAGCACGA-3' (SEQ ID NO: 18) (Sigma, N/A), Primers: mouse-mcp-1-Fwd: 5'-GC- TACAAGAGGATCACCAGCAG-3' (SEQ ID NO: 19) and Rev: 5'-GTCTGGACCCATTCCTTCTTGG-3' (SEQ ID NO: 20) (Sigma, N/A), Primers: mouse-β-actin-Fwd: 5'-CTGTCCCTGTATGCCTCTG-3' (SEQ ID NO: 21) and Rev: 5'-ATGTCACGCACGATTTCC-3' (SEQ ID NO: 22) (Sigma, N/A), and Primers: human-β-actin-Fwd: 5'-AGCGAGCATCCCCCAAAGTT-3' (SEQ ID NO: 23) and Rev: 5'-AGGGCACGAAGGCTCATCATT-3' (SEQ ID NO: 24) (Sigma, N/A).

Software and Algorithms:

Heml 1.0.3.3-Heatmap Illustrator and Quick Spots Image Analysis Software, Western Vision Software.

CLP Model:

sepsis was induced in male or female C57BL/6J mice (eight- to 10-weeks old, 22 to 26 g) using a surgical procedure as previously described (68). Briefly, anesthesia was induced with ketamine (80-100 mg/kg/i.p.) and xylazine (10-12.5 mg/kg/i.p.). A small midline abdominal incision was made and the cecum was exteriorized and ligated with 4-0 silk immediately distal to the ileocecal valve without causing intestinal obstruction. The cecum was then punctured twice with a 17-27-gauge needle. The abdomen was closed in two layers and mice were injected subcutaneously with 1 ml Ringer's solution including analgesia (0.05 mg/kg buprenorphine). LDK378 (20 mg/kg) was dissolved in vehicle (10% DMSO, 20% cremophor:ethanol [3:1] and 70% phosphate buffered saline (PBS)) and repeatedly administered orally to mice at two, 24, 48, and 72 hours after CLP.

Endotoxemia Model:

LPS (*Escherichia coli* 0111:64, 10 mg/kg, #L4391, Sigma) was dissolved in PBS. Male or female C57BL/6J mice (eight- to 10-weeks old, 22 to 26 g weight) received a single oral dose of LDK378 (20 mg/kg) or vehicle, then an infusion of LPS (10 mg/kg, intraperitoneally) 60 minutes later. Mice were re-treated with LDK378 or vehicle six, 12, and 24 hours after LPS infusion.

Patient Samples:

PBMCs from patients with sepsis (n=16) and healthy controls (n=16) were collected from Daping Hospital and Xiangya Hospital. Collection of samples was approved by the Institutional Review Board. Sepsis was identified according to The Third International Consensus Definitions for Sepsis and Septic Shock (Sepsis-3).

Cell Culture:

Immortalized bone marrow-derived macrophages (iBMDMs, a kind gift from Dr. Kate Fitzgerald at University of Massachusetts Medical School), murine macrophage-like RAW264.7 (American Type Culture Collection [ATCC], #TIB-71), murine J774A.1 (ATCC, #TIB-67), and human monocytic THP-1 cell lines (ATCC, #TIB-202) were cultured in Dulbecco's Modified Eagle Medium supplemented with 10% fetal bovine serum (FBS) and 1× penicillin-streptomycin. Human PBMCs were purchased from Life-Line Cell Technology (#1207). Macrophages/monocytes were maintained in a 5% CO2 incubator at 37° C. All cells were mycoplasma-free and authenticated with Short Tandem Repeat DNA Profiling Analysis.

Mouse pPMs were isolated from C57BL/6J mice as previously described (69). In brief, eight-week-old female or male C57BL/6J mice were injected with 3.0% thioglycollate medium (2 mL/mouse) into the peritoneum. Three days after injection, mice were sacrificed and injected with 3 mL of 0.05% EDTA-PBS into the peritoneum to harvest peritoneal macrophages. Collected cells were centrifuged at 1000 rpm for 5 min at 4° C., and the cell pellet was washed with PBS and centrifuged again. The cell pellet was then suspended in Dulbecco's Modified Eagle Medium supplemented with 10% FBS and 1× Penicillin-Streptomycin and cultured in a culture dish.

Immunoblotting and Immunoprecipitation:

For immunoblotting, cells were lysed in Cell Lysis Buffer (#9803, Cell Signaling Technology) with protease inhibitor cocktail (Promega), phosphatase inhibitor cocktail (Sigma), and 1 mM $Na_3VO_4$ (70). Cleared lysates were resolved by SDS-PAGE (#3450124, Bio-Rad) and then transferred onto PVDF membranes (#1704273, Bio-Rad). The membranes were blocked with Tris-buffered saline Tween 20 (TBST) containing 5% skim milk for 1 h at room temperature and then incubated with the indicated primary antibodies (1:1000-1:5000) overnight at 4° C. After being washed with TBST, the membranes were incubated with an HRP-linked anti-mouse IgG secondary antibody (#7076, Cell Signaling Technology) or HRP-linked anti-rabbit IgG secondary antibody (#7074, Cell Signaling Technology) for 1 h at room temperature. The membranes were washed three times in TBST and then visualized and analyzed with a ChemiDoc Touch Imaging System (#1708370, Bio-Rad). The intensities of bands were analyzed with Image Lab software.

For immunoprecipitation, cells were lysed at 4° C. in ice-cold modified radioimmunoprecipitation lysis buffer (#9806, Cell Signaling Technology) and cell lysates were cleared by centrifugation (12,000 g, 10 min). Concentrations of proteins in the supernatant were determined by bicinchoninic acid assay. Prior to immunoprecipitation, samples containing equal amounts of proteins were pre-cleared with Protein A/G agarose/sepharose beads (#20423, Thermo Fisher Scientific Inc.) (4° C., 3 h) and subsequently incubated with various irrelevant IgG or anti-ALK (#ab190934, Abcam) or anti-EGFR antibodies (#2232S, Cell Signaling Technology) in the presence of Protein A/G agarose/sepharose beads overnight at 4° C. with gentle shaking. Following incubation, agarose/sepharose beads were washed extensively with PBS and proteins were eluted by boiling in 2× sodium dodecyl sulfate (SDS) sample buffer before SDS-PAGE electrophoresis.

The antibodies to p-STING (#85735; 1:1000), STING (#13647; 1:1000), p-TBK1/NAK (#S172; 1:1000) (#5483; 1:1000), TBK1/NAK (#3504; 1:1000), IRF3 (#4962; 1:1000), p-IRF3(S396; #4947S; 1:1000), p-p65 (S536; #3033P; 1:1000), p-EGFR (Y1068; #3777T; 1:1000), EGFR (#2232; 1:1000), p-AKT (S473; #4060 ; 1:1000), and S6 (#2317; 1:1000) were obtained from Cell Signaling Technology. The antibody to p-ALK (Y1057; #ab192809; 1:1000) was obtained from Abcam. The antibody to ALK (#sc-398791; 1:100) was obtained from Santa Cruz Biotechnology. The antibody to TRIF (#A01872; 1:500) was obtained from Boster.

Statistical Analysis:

Data are expressed as means±SD. Unpaired Student's t tests were used to compare the means of two groups. One-way Analysis of Variance (ANOVA) was used for comparison among the different groups. When ANOVA was significant, post hoc testing of differences between groups was performed using the Least Significant Difference (LSD) test. The Kaplan-Meier method was used to compare differences in mortality rates between groups. A P-value <0.05 was considered statistically significant.

ELISA:

Macrophages or monocytes were treated with 3'3'-cGAMP (10 μg/ml, Invitrogen) for 16 hours in the absence or presence of one compound (10 μM) from the Target-selective Inhibitory Library (#L3500, Selleck Chemicals). Commercially available enzyme-linked immunosorbent assay (ELISA) kits were used to measure the concentrations of mouse IFNβ (Thermo Fisher Scientific) or human IFNβ (Thermo Fisher Scientific) in culture medium according to the manufacturer's instructions.

RNA Interference:

All shRNA constructs were in the pLKO.1 backbone. Mouse ALK-shRNA (# TRCN0000023724 and # TRCN0000023726), human ALK-shRNA (#TRCN0000000784 and #TRCN0000000787), mouse EGFR-shRNA (#TRCN0000055218 and # TRCN0000055221), human EGFR-shRNA (#TRCN0000199532 and # TRCN0000199174), and control empty shRNA (#SHC016V) were purchased from Sigma. Cells (2×106 cells/well) were seeded in six-well plates and then transfected with 2500 ng shRNA by Lipofectamine 3000 (#L3000008, Invitrogen) per the manufacturer's instructions. Stable cell lines were generated using puromycin (Sigma).

Q-PCR:

Total RNA was extracted using QIAGEN RNeasy Plus Kit according to the manufacturer's instructions. First-strand cDNA was synthesized from 1 μg of RNA using the iScript cDNA Synthesis kit (#1708890, Bio-Rad). Briefly, 20 μl reactions were prepared by combining 4 μl iScript Select reaction mix, 2 μl gene-specific enhancer solution, 1 μl reverse transcriptase, 1 μl gene-specific assay pool (20×, 2 μM), and 12 μl RNA diluted in RNase-free water. Quantitative real-time PCR was carried out using synthesized cDNA, primers, and SsoFast EvaGreen Supermix (#172-5204, Bio-Rad). The expression of target genes was calculated using the ddCt method relative to the expression of a house-keeping gene, β-actin. Data shown are the relative quantity (RQ), with RQ of the control cells set to one.

Proteome Profiler Antibody Arrays Analysis:

The Proteome Profiler Mouse XL Cytokine Array Kit (#ARY028) and the Proteome Profiler Mouse Phospho-RTK Array Kit (#ARY014) are membrane-based sandwich immunoassays. Captured antibodies spotted in duplicate on nitrocellulose membranes bind to specific target proteins present in the sample (Step 1). Captured proteins are detected with biotinylated detection antibodies (Step 2) and then visualized using chemiluminescent detection reagents (Step 3). The signal produced is proportional to the amount of analyte bound. The intensities of bands were analyzed with Quick Spots Image Analysis Software (Western Vision Software, http://www.wvision.com/QuickSpots.html).

Biochemical Assay:

Biochemical measurements of tissue enzymes (CK, AMYL, BUN, and ALT) in serum were performed using the IDEXX Catalyst Dx Chemistry Analyzer according to the manufacturer's protocol.

Cell Cycle Analysis:

Cells were collected, trypsinized, and fixed in 70% ethanol overnight. Cells were centrifuged at 1,000 rpm for 5 min, washed once with pre-cooled PBS, and incubated with propidium iodide staining solution for at least 30 min at room temperature before analysis. Analysis of the percentage of total cells for each phase of the cell cycle (G0/G1, S, and G2/M) was performed using a Muse Cell Analyzer (EMD Millipore) in accordance with the manufacturer's guidelines.

Hematoxylin and Eosin (H&E) Tissue Staining:

Tissues were embedded in optimum cutting temperature cryomedium (Sakura Finetek, Zoeterwoude, the Netherlands) and cut into 4 μm sections. The deparaffinized sections were then stained using the standard H&E method. The stained slides were observed using an EVOS FL Auto Cell Imaging System (Invitrogen), five fields per section and three sections per sample.

Cell Viability Assay:

Cells were seeded into 96-well plates and incubated with the indicated treatments. Subsequently, 100 μl fresh medium was added to cells containing 10 μl Cell Counting Kit-8 (CCK-8) solutions (Dojindo Laboratories) and incubated for 1 h (37° C., 5% $CO_2$). Absorbance at 450 nm was measured using a microplate reader (Tecan).

Results

Bioactive Compound Screening Identifies STING Modulators:

To ensure a timely response to bacteria-derived CDN, an effective innate recognition system consisting of STING and other unknown transmembrane regulators has evolved in mammals (19). The 3'3'-cGAMP is a type of CDN and serves as a canonical STING ligand to induce the production of type I IFNs (IFNα and IFNβ). To identify other potential endogenous regulators of the STING signaling pathway in innate immune cells, we screened a library of 464 compounds that selectively target 174 signaling molecules in immortalized bone marrow-derived macrophages (iBMDMs) from B6 mice. Each compound was selected based on its ability to principally interact with a single target, leading to minimal off-target activity. The following provides the —fold increase in IFN-β release for the tested compounds: Lidocaine (9.58), Stavudine (d4T) (8.20), Thiazovivin (8.11), AM1241 (8.07), AS-252424 (6.84), VX-745 (6.18), Pyrimethamine (5.22), Oxcarbazepine (5.22), Safinamide Mesylate (5.18), LY2228820 (5.15), Raltegravir (MK-0518) (4.80), MLN2238 (4.76), (−)-MK 801 Maleate (4.76), MK-1775 (4.54), Erastin (4.52), AZD6482 (4.47), Pralatrexate (4.31), Golgicide A (4.19), 4EGI-1 (4.14), Zosuquidar (LY335979) 3HCl (4.10), CW069 (4.03), Torcetrapib (3.84), IWP-2 (3.84), Loratadine (3.65), AZD7545 (3.45), PF-04620110 (3.43), SP600125 (3.35), DMXAA (Vadimezan) (3.23), Imidapril HCl (3.20), C646 (3.17), Roxatidine Acetate HCl (3.16), Allopurinol (3.15), Naltrexone HCl (3.12), BTB06584 (3.11), AZD1981 (3.11), (S)-crizotinib (3.05), Labetalol HCl (2.96), GNF-5 (2.94), Tenofovir Disoproxil Fumarate (2.88), Ranitidine (2.87), Rizatriptan Benzoate (2.85), Lafutidine (2.85), Apixaban (2.83), JSH-23 (2.80), GSK429286A (2.79), CRT0044876 (2.75), TAK-700 (Orteronel) (2.72), Enalaprilat Dihydrate (2.71), Tadalafil (2.66), TG100-115 (2.65), TPCA-1 (2.63), SC144 (2.63), Captopril (2.62), 2-Methoxyestradiol (2-MeOE2) (2.62), Memantine HCl (2.60), GSK1292263 (2.58), Elvitegravir (GS-9137, JTK-303) (2.56), Rebamipide (2.54), Ferrostatin-1 (Fer-1) (2.54), ZCL278 (2.52), CGK 733 (2.50), LY2157299 (2.50), GW9662 (2.50), Maraviroc (2.50), Oligomycin A (2.49), Naftopidil (2.46), NSC 319726 (2.43), RKI-1447 (2.41), GNE-7915 (2.41), AG-14361 (2.41), U-104 (2.41), XMD8-92 (2.38), SRPIN340 (2.38), 4E1 RCat (2.36), Filgotinib (GLPG0634) (2.35), Voriconazole (2.35), MM-102 (2.32), Candesartan (2.31), PHA-793887 (2.28), Telmisartan (2.26), Tolfenamic Acid (2.19), DBeQ (2.18), IM-12 (2.17), Ro3280 (2.16), PF-3845 (2.14), MetoclopraMide HCl (2.14), Ginkgolide A (2.14), AGI-6780 (2.14), Ozagrel HCl (2.13), A-769662 (2.13), (R)-Nepicastat HCl (2.13), GDC-0941 (2.13), PF-4708671 (2.12), ML130 (Nodinitib-1) (2.12), Ispinesib (SB-715992) (2.12), Pomalidomide (2.12), Anacetrapib (MK-0859) (2.12), AZD2461 (2.12), PTC-209 (2.11), Mdivi-1 (2.10), BIBR 1532 (2.10), Tropicamide (2.09), LY2784544 (2.09), T0070907 (2.09), Cilomilast (2.08), URB597 (2.07), Propranolol HCl (2.07), Pramipexole (2.07), Linagliptin (2.07), FLI-06 (2.06), CK-636 (2.06), Tie2 kinase inhibitor (2.04), AZ191 (2.01), CGS 21680 HCl (2.00), VU 0364770 (2.00), Tyrphostin AG 879 (1.99), NLG919 (1.99), UNC669 (1.99), ML347 (1.95), CNX-2006 (1.93), Gliclazide (1.93), Brinzolamide (1.93), PD 151746 (1.92), Levosulpiride (1.91), H 89 2HCl (1.91), Istradefylline (1.90), SGC 0946 (1.90), NMS-873 (1.90), SB408124 (1.90), Tioxolone (1.88), Moclobemide (Ro 111163) (1.88), Carvedilol (1.87), ARQ 621 (1.87), BX-912 (1.86), Rolipram (1.85), Ilomastat (GM6001, Galardin) (1.81), Ganetespib (STA-9090) (1.80), Fluvoxamine maleate (1.80), Trelagliptin (1.80), Nilvadipine (1.79), GDC-0152 (1.79), Pimobendan (1.79), Bosutinib (SKI-606) (1.78), ABT-199 (GDC-0199) (1.78), Rasagiline Mesylate (1.77), Formoterol Hemifumarate (1.76), YO-01027 (1.74), Ataluren (PTC124) (1.74), Org 27569 (1.74), ADX-47273 (1.72), SN-38 (1.72), DCC-2036 (Rebastinib) (1.71), Ifenprodil Tartrate (1.71), BMS-378806 (1.70), Ticagrelor (1.70), EHop-016 (1.69), VX-765 (1.67), WZ811 (1.67), Dynasore (1.62), VU 0364439 (1.60), Necrostatin-1 (1.60), BMS-707035 (1.59), TMP269 (1.59), Canagliflozin (1.58), GSK2656157 (1.58), Pacritinib (SB1518) (1.58), Dapagliflozin (1.57), Suvorexant (MK-4305) (1.54), 17-AAG (Tanespimycin) (1.53), TAE226 (NVP-TAE226) (1.50), Zebularine (1.50), VU 0357121 (1.49), SANT-1 (1.49), PF-04217903 (1.49), Tofacitinib (CP-690550, Tasocitinib) (1.49), T0901317 (1.49), MK-2866 (GTx-024) (1.47), Naproxen (1.46), Amlodipine (1.46), CCT128930 (1.46), Tolazoline HCl (1.46), Atorvastatin Calcium (1.45), Ginkgolide B (1.44), LDC000067 (1.43), TCID (1.43), DMH1 (1.43), WZ4002 (1.42), Ki16425 (1.41), STF-118804 (1.41), GSK2606414 (1.40), Losartan Potassium (DuP 753) (1.35), LB42708 (1.35), GNE-0877 (1.32), Clemastine Fumarate (1.32), LDE225 (NVP-LDE225, Erismodegib) (1.31), MRS 2578 (1.31), CHIR-124 (1.30), SC-514 (1.30), NSC 23766 (1.30), ABT-263 (Navitoclax) (1.27), Ivacaftor (VX-770) (1.27), Lomeguatrib (1.27), GW4064 (1.26), (+)-Bicuculline (1.26), NSC 405020 (1.24), Cyproterone Acetate (1.24), Lovastatin (1.22), GW2580 (1.21), Losmapimod (GW856553X) (1.20), Batimastat (BB-94) (1.20), Tolvaptan (1.20), Gliquidone (1.20), Pancuronium dibromide (1.20), Bosentan Hydrate (1.20), Santacruzamate A (CAY10683) (1.18), Varespladib (LY315920) (1.18), 00000459 (1.18), AMG-517 (1.18), 6H05 (1.18), Zibotentan (ZD4054) (1.17), TAK-875 (1.17), Tranylcypromine (2-PCPA) HCl (1.17), Oxymetazoline HCl (1.16), Sitaxentan sodium (1.16), SB743921 (1.16), IKK-16 (IKK Inhibitor VII) (1.16), SB415286 (1.15), Birinapant (1.15), Irinotecan (1.13), SAR131675 (1.13), PYR-41 (1.13), PU-H71 (1.13), AGI-5198 (1.13), 4p8C (1.13), GSK690693 (1.12), Exemestane (1.11), SNS-314 Mesylate (1.10), GNE-9605 (1.10), 5-hydroxymethyl Tolterodine (PNU 200577, 5-HMT, 5-HM) (1.10), EUK 134 (1.10), Lenalidomide (CC-5013) (1.09), LY2603618 (1.08), Ouabain (1.08), VX-809 (Lumacaftor) (1.07), OG-L002 (1.06), HJC0350 (1.05), Tubacin (1.05), HC-030031 (1.05), GSK1904529A (1.05), Imatinib (STI571) (1.04), Vildagliptin (LAF-237) (1.04), Semagacestat (LY450139) (1.04), JNJ-1661010 (1.03), EPZ-6438 (1.03), Aniracetam (1.02), Acadesine (1.02), Enzastaurin (LY317615) (1.02), MK-2206 2HCl (1.02), Everolimus (RAD001) (1.01), SNS-032 (BMS-387032) (1.01), XAV-939 (1.00), NPS-2143 (0.99), Triamterene (0.99), RepSox (0.99), Anastrozole (0.98), SSR128129E (0.98), EX 527 (Selisistat) (0.98), Agomelatine (0.97), Rigosertib (ON-01910) (0.96), Esomeprazole Sodium (0.95), ML161 (0.95), ADL5859 HCl (0.95), Palbociclib (PD-0332991) HCl (0.94), PD184352 (CI-1040) (0.94), AUY922 (NVP-AUY922) (0.93), Quizartinib (AC220) (0.91), Atglistatin (0.91), VX-680 (Tozasertib, MK-0457) (0.91), Sorafenib (0.91), Odanacatib (MK-0822) (0.90), S3I-201 (0.88), PF-573228 (0.87), Dabrafenib (GSK2118436) (0.86), VE-822 (0.86), Etomidate (0.86), GDC-0068 (0.86), PD128907 HCl (0.86), IMD 0354 (0.86), Finasteride (0.85), AZD9291 (0.85), SMI-4a (0.84), CEP-18770 (Delanzomib) (0.82), Forskolin (0.81), Rimonabant (0.81), GW9508 (0.80), BI-D1870 (0.79), PR-619 (0.79), SB431542 (0.78), Tariquidar (0.77), Nilotinib (AMN-107) (0.77), KX2-391 (0.77), Fingolimod (FTY720) HCl (0.77), MLN8054 (0.77), SRT1720 (0.76), Trospium chloride (0.76), Entacapone (0.76), Aprepitant (0.76), Celecoxib (0.76), N6022 (0.75), SU11274 (0.75), Nebivolol (0.75), GW3965 HCl (0.74), Sodium 4-Aminosalicylate (0.74), CNX-774 (0.73), Temsirolimus (CCI-779, NSC 683864) (0.73), FG-4592 (0.73), NMS-P937 (NMS1286937) (0.73), Loxistatin Acid (E-64C) (0.70), Belinostat (PXD101) (0.70), Bisoprolol fumarate (0.70), U0126-EtOH (0.70), Felodipine (0.69), Doxazosin Mesylate (0.69), BTZ043 Racemate (0.69), ZM 447439 (0.69), Fostamatinib (R788) (0.69), Mirabegron (0.69), PFK15 (0.68), Methotrexate (0.68), OSI-906 (Linsitinib) (0.66), Veliparib (ABT-888) (0.66), Tandutinib (MLN518) (0.65), SGI-1776 free base (0.65), SB742457 (0.65), Refametinib (RDEA119, Bay 86-9766) (0.64), PluriSln #1 (NSC 14613) (0.62), Panobinostat (LBH589) (0.61), NVP-ADW742 (0.61), Letrozole (0.61), PI-1840 (0.60), Vemurafenib (PLX4032, RG7204) (0.59), ML133 HCl (0.59), KPT-185 (0.59), Sotrastaurin (0.59), Ridaforolimus (Deforolimus, MK-8669) (0.58), Empagliflozin (BI 10773) (0.57), Bergenin (0.57), Icotinib (0.57), Mubritinib (TAK 165) (0.56), GNF-2 (0.56), Ramelteon (0.56), Cinacalcet HCl (0.55), Rotundine (0.54), Rivaroxaban (0.54), CGP 57380 (0.54), KPT-276 (0.54), Ibrutinib (PCI-32765) (0.53), Tenovin-6 (0.53), JNK Inhibitor IX (0.53), HO-3867 (0.52), PFI-1 (PF-6405761) (0.52), Fulvestrant (0.52), BAPTA-AM (0.52), NSC697923 (0.51), Dutasteride (0.51), Irinotecan HCl Trihydrate (0.51), Ki16198 (0.51), Enzalutamide (MDV3100) (0.50), Selumetinib (AZD6244) (0.50), SKI II (0.49), SB-3CT (0.49), TCS 359 (0.45), AZD7762 (0.45), BI 2536 (0.45), VE-821 (0.45), HA14-1 (0.45), Apigenin (0.44), IOX2 (0.44), Caffeic Acid Phenethyl Ester (0.44), ML323 (0.43), PHA-665752 (0.43), OTX015 (0.43), MK-8245 (0.42), Bupivacaine HCl (0.42), Piceatannol (0.42), I-BET151 (GSK1210151A) (0.40), GSK J4 HCl (0.40), PD0325901 (0.39), Trichostatin A (TSA) (0.39), Costunolide (0.37), SGI-1027 (0.37), Bortezomib (PS-341) (0.37), AZD4547 (0.35), IPA-3 (0.35), BML-190 (0.35), P22077 (0.35), TWS119 (0.35), SB203580 (0.35), Etodolac (0.35), LDN-212854 (0.33), KU-55933 (ATM Kinase Inhibitor) (0.33), Fluvastatin Sodium (0.32), Crenolanib (CP-868596) (0.32), VS-5584 (SB2343) (0.32), SB705498 (0.32), AZ20 (0.32), OSU-03012 (AR-12) (0.31), Aloxistatin (0.31), Trimebutine (0.30), YM155 (Sepantronium Bromide) (0.30), Alvelestat (AZD9668) (0.27), PTC-209 HBr (0.27), CP-673451 (0.27), XL335 (0.26), MNS (3,4-Methylenedioxy-β-nitrostyrene, MDBN) (0.26), Apatinib (0.26), Go 6983 (0.26), LY411575 (0.26), Sirtinol (0.26), HSP990 (NVP-HSP990) (0.26), Vandetanib (ZD6474) (0.25), Iniparib (BSI-201) (0.23), Sertraline HCl (0.22), GSK461364 (0.21), PF-562271 (0.21), Ruxolitinib (INCB018424) (0.20), Toremifene Citrate (0.19), AP26113 (0.19), Sal003 (0.18), PAC-1 (0.17), Embelin (0.17), E-64 (0.17), Cryptotanshinone (0.17), Apoptosis Activator 2 (0.17), AVL-292 (0.16), PF-5274857 (0.16), CG11746 (0.16), (−)-Parthenolide (0.16), Pifithrin-μ (0.16), Bazedoxifene HCl (0.15), CP-91149 (0.14), PP2 (0.14), OSI-420 (0.14), ZM 306416

(0.14), Dalcetrapib (JTT-705, RO4607381) (0.13), Wnt-059 (C59) (0.13), AT101 (0.13), (+)-JQ1 (0.13), GW0742 (0.13), PNU-120596 (0.12), WZ4003 (0.12), NH125 (0.11), Ozagrel (0.11), Daunorubicin HCl (0.11), Isotretinoin (0.10), ICG-001 (0.10), Ospemifene (0.10), AZ 3146 (0.10), Stattic (0.10), LDK378 (0.08), PRT062607 (P505-15, BIIB057) HCl (0.07), KU-60019 (0.06), AZD3463 (0.05), and KPT-330 (0.05).

Figure 2B:
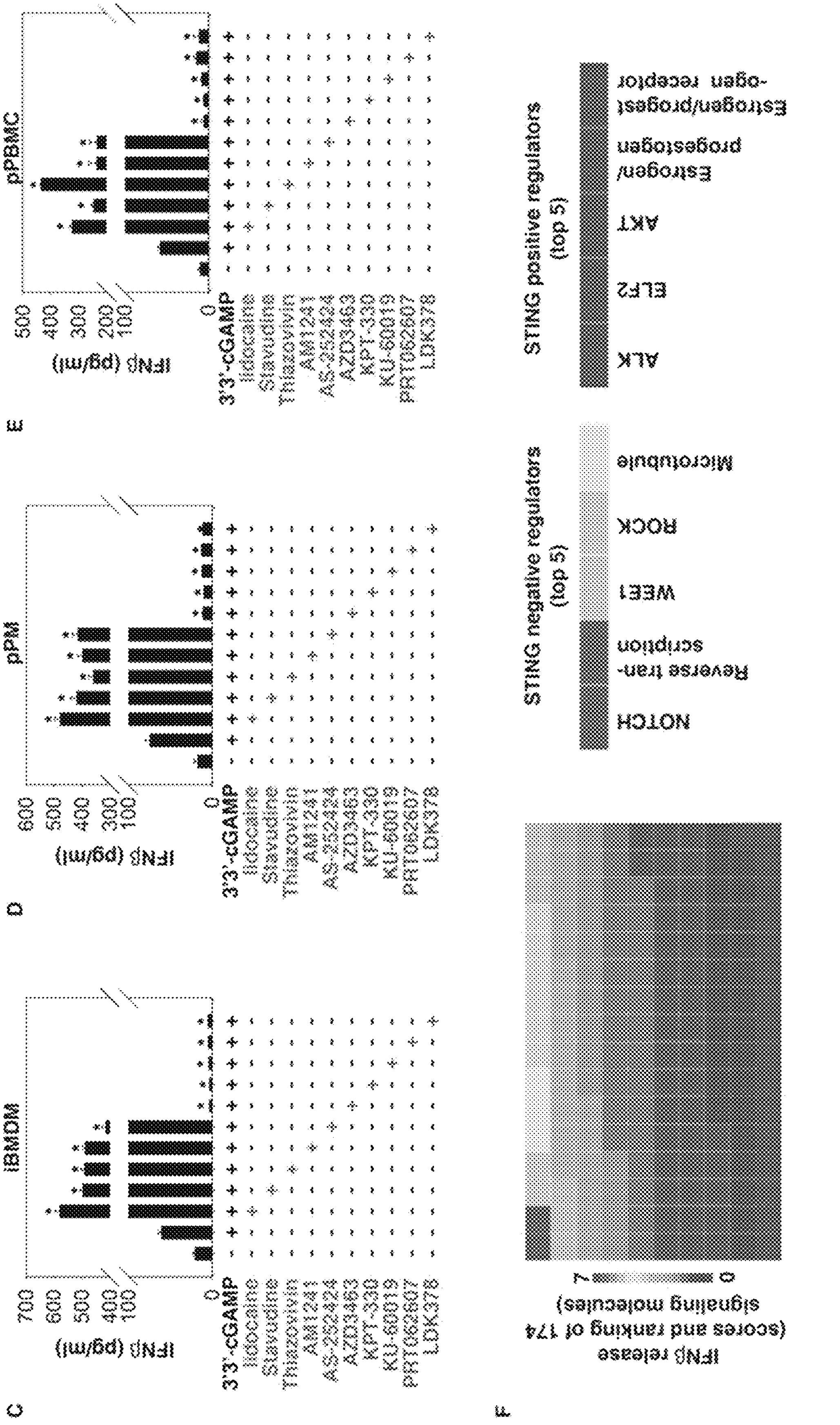

3'3'-cGAMP-induced IFN-β release in iBMDMs was changed by several target-selective inhibitors (FIG. 2A, panel A (FIG. 2A (A))). The top five compounds that promoted the 3'3'-cGAMP-induced IFN-β release included lidocaine (a selective inverse peripheral histamine H1-receptor agonist), stavudine (a nucleoside analog reverse transcriptase inhibitor [NARTI] active against HIV), thiazovivin (a novel Rho-associated coiled-coil containing protein kinase [ROCK] inhibitor), AM1241 (a selective cannabinoid CB2 receptor agonist), and AS-252424 (a novel and potent phosphatidylinositol-4,5-bisphosphate 3-kinase catalytic subunit gamma [PI3Kγ] inhibitor) (FIG. 2A (B)). In contrast, the top five compounds that blocked 3'3'-cGAMP-induced IFNβ release in iBMDMs included AZD3463 (a novel orally-bioavailable ALK inhibitor), KPT-330 (an orally-bioavailable selective exportin-1 inhibitor), KU-60019 (a potent and specific ataxia telangiectasia mutated [ATM] inhibitor), PRT062607 (a novel and highly selective spleen-associated tyrosine kinase [Syk] inhibitor), and LDK378 (an inhibitor against ALK) (FIG. 2A (B)). These top five bioactive compounds were further tested in primary peritoneal macrophages (pPMs) from B6 mice and human primary peripheral blood mononuclear cells (pPBMCs), which confirmed their inhibitory properties in mouse iBMDMs (FIG. 2B (C)), mouse pPMs (FIG. 2B (D)), and human pPBMCs (FIG. 2B (E)). Although STING plays divergent and stimulus-dependent roles in innate immunity, a recent study revealed that activation of STING by bacteria accelerated the inflammatory response, organ dysfunction, and death in a mouse model of septic shock. Thus, the STING pathway seems to be a viable target for pharmacologic intervention during bacterial sepsis. After further analysis of the 174 molecular targets, we found that ALK was the top-ranked signaling molecule that promoted 3'3'-cGAMP-induced STING activation, based on IFNβ release from iBMDMs (FIG. 2B (F)). Together, these findings suggest that ALK is a possible modulator of STING activation during bacterial infections.

Figure 3:
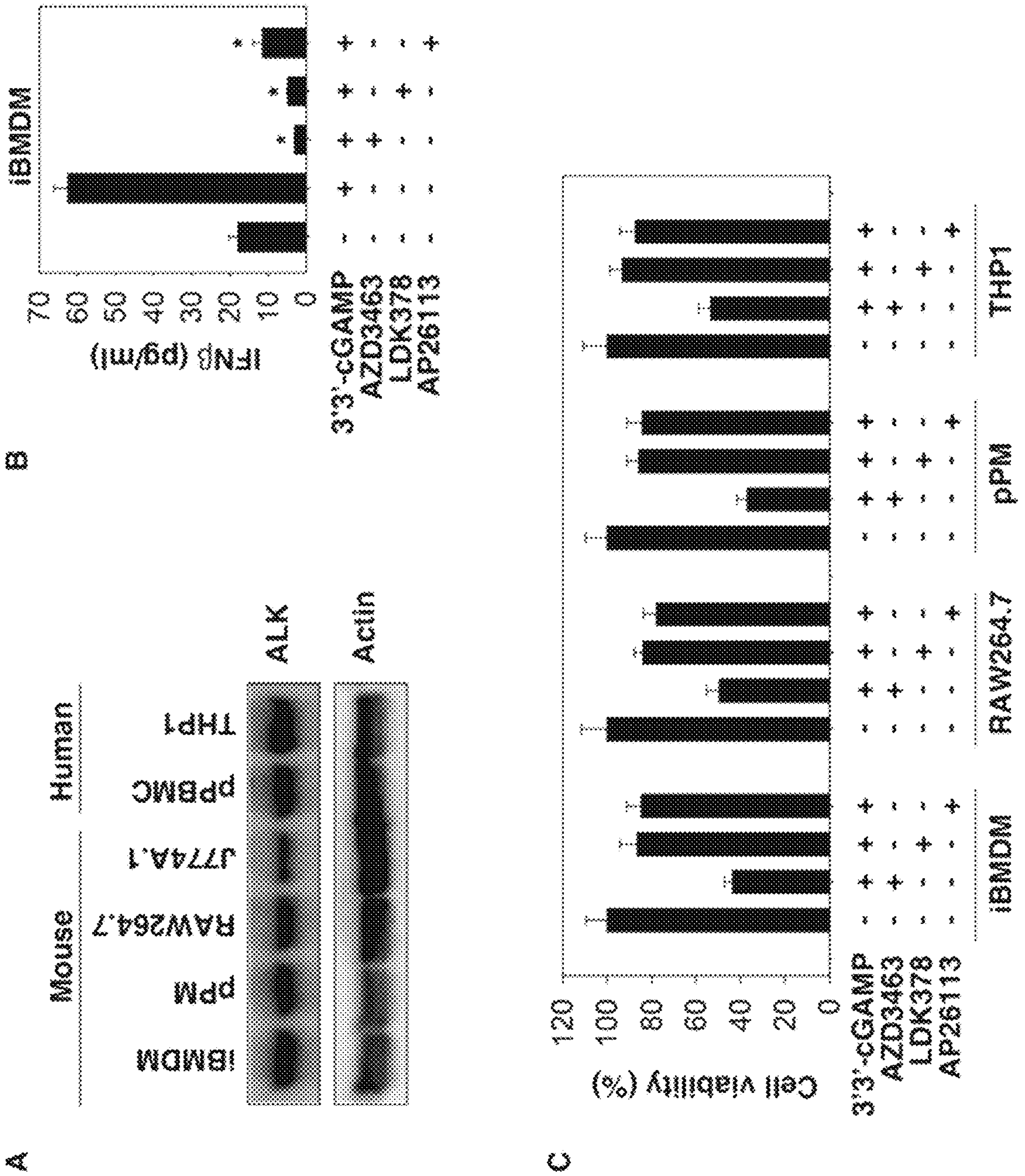
FIG. 3. ALK inhibitors block STING activation. (A) Western blot analysis of ALK expression in indicated macrophages or monocytes. (B) iBMDMs were treated with 3'3'-cGAMP (10 μg/ml) in the absence or presence of indicated ALK inhibitors (10 μM) for 16 hours. The release of IFNβ was assayed with ELISA (n=3, data expressed as means±SD, *P<0.05 versus 3'3'-cGAMP group, ANOVA LSD test). (C) Macrophages or monocytes were treated with 3'3'-cGAMP (10 μg/ml) in the absence or presence of indicated ALK inhibitors (10 μM) for 16 hours. Cell viability was assayed (n=3, data expressed as means±SD).
Figure 4A:
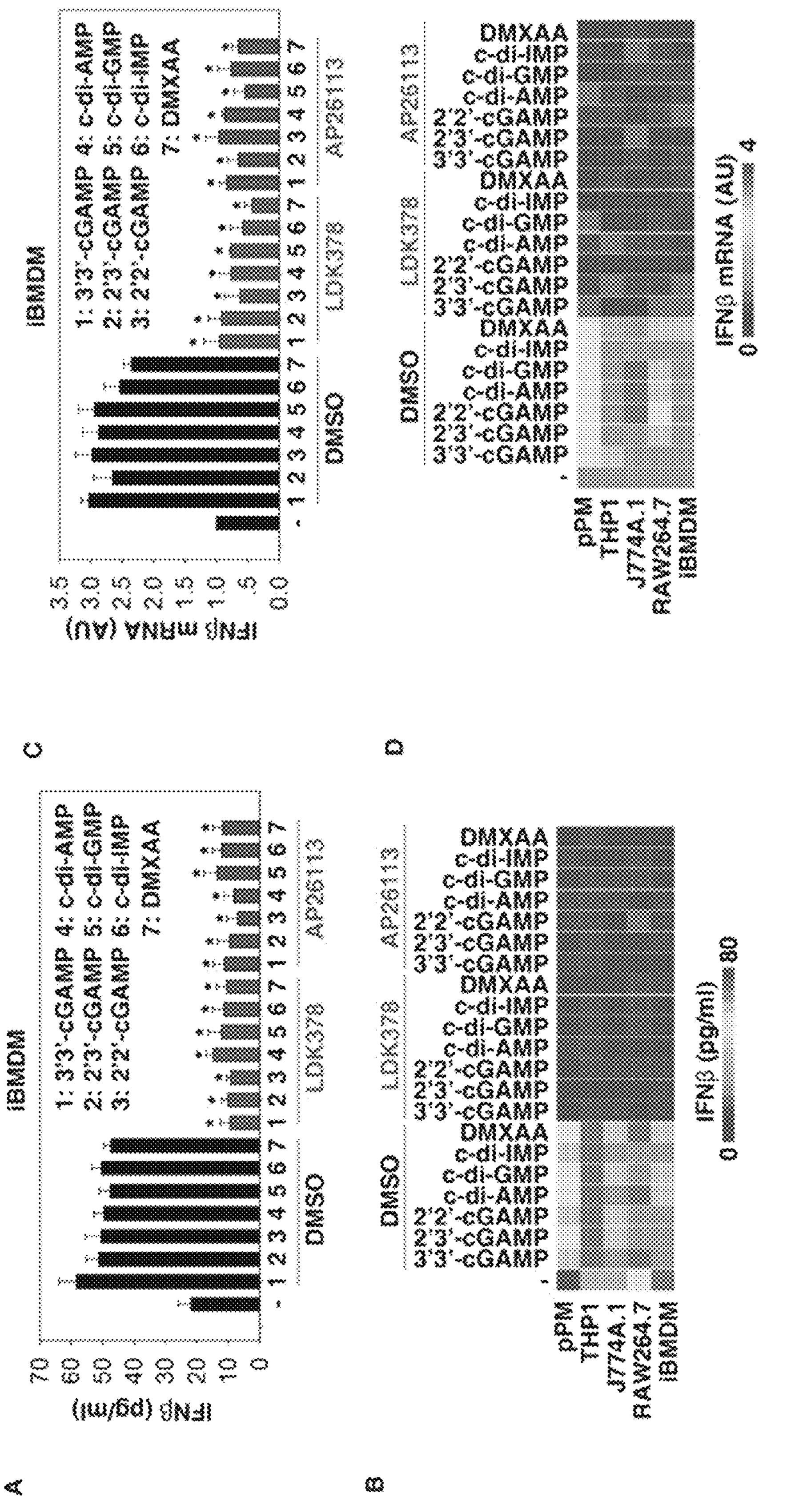
FIGS. 4A and 4B. Pharmacologic inhibition of ALK impairs STING activation. (A) iBMDMs were stimulated with indicated STING ligands (10 μg/ml) in the absence or presence of LDK378 (10 μM), AP26113 (10 μM), or control vehicle (DMSO) for 16 hours, and the release of IFNβ was assayed using ELISA (n=3, data expressed as means±SD, *P<0.05 versus DMSO group, ANOVA LSD test). (B) Heatmap of IFNβ release changes in macrophages or monocytes following STING ligand (10 μg/ml) stimulation in combination with LDK378 (10 μM), AP26113 (10 μM), or vehicle (DMSO) for 16 hours. (C) iBMDMs were stimulated with indicated STING ligands (10 μg/ml) in the absence or presence of LDK378 (10 μM), AP26113 (10 μM), or vehicle (DMSO) for 16 hours, and IFNβ mRNA was assayed with Q-PCR (n=3, data expressed as means±SD, *P<0.05 versus DMSO group, ANOVA LSD test). (D) Heatmap of IFNβ mRNA changes in macrophages or monocytes following STING ligand (10 μg/ml) stimulation in combination with LDK378 (10 μM), AP26113 (10 μM), or vehicle (DMSO) for 16 hours. (E, F) Western blot analysis of indicated protein expression in iBMDMs (E) or J744A.1 (F) cells after 3'3'-cGAMP (10 μg/ml) stimulation in combination with LDK378 (10 μM), AP26113 (10 μM), or vehicle (DMSO) for three to 16 hours. (G, H) Western blot analysis of indicated protein expression in iBMDMs (G) or J744A.1 (H) cells after c-di-AMP (10 μg/ml) or DMXAA (10 μg/ml) stimulation in combination with LDK378 (10 μM), AP26113 (10 μM), or vehicle (DMSO) for 16 hours.
Figure 5:
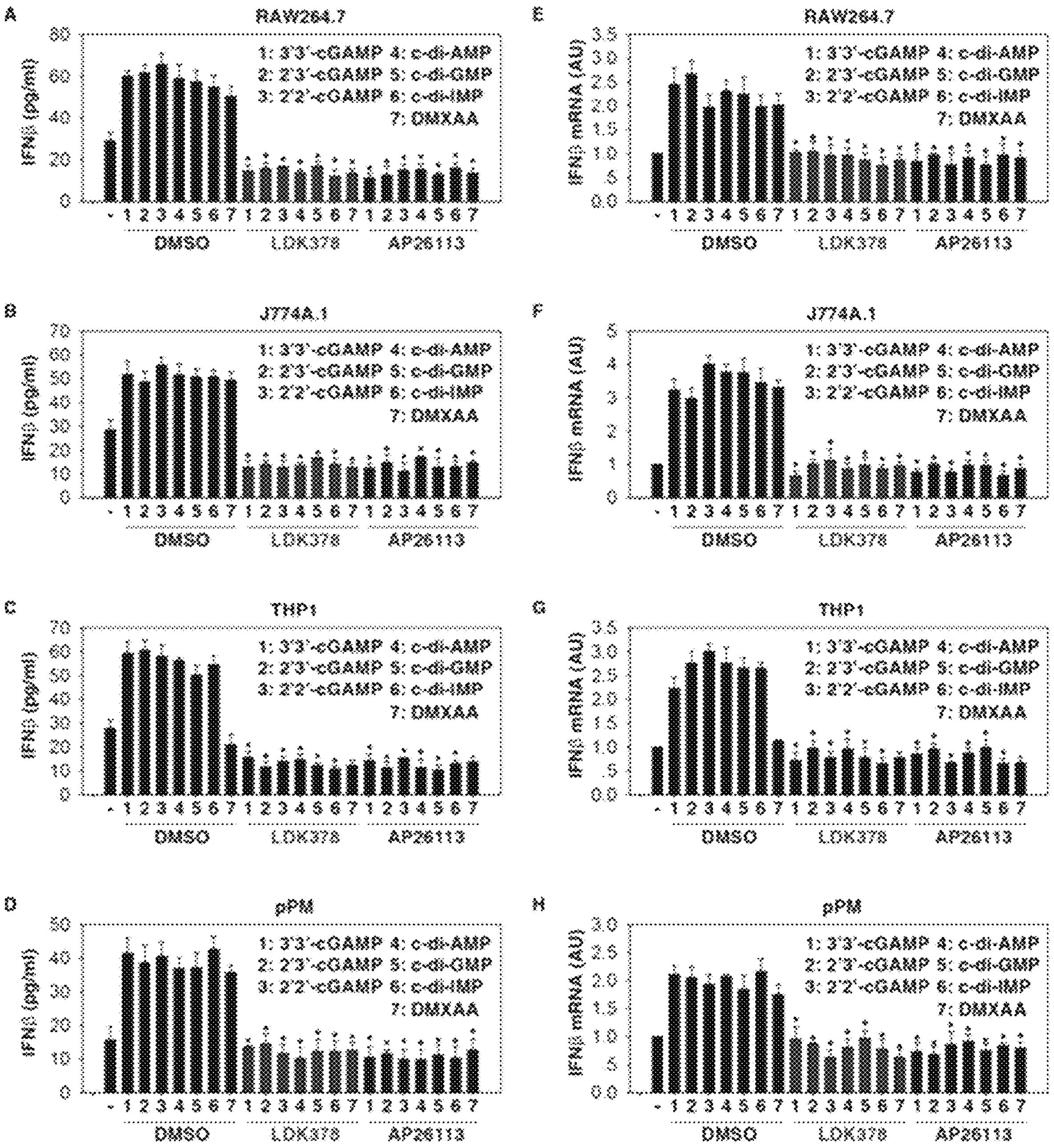
FIG. 5. Pharmacologic inhibition of ALK blocks STING ligand-induced IFNβ release and expression. Indicated macrophages or monocytes were treated with indicated STING ligands (10 μg/ml) in the absence or presence of LDK378 (10 μM), AP26113 (10 μM), or vehicle (DMSO) for 16 hours. The release of IFNβ (A-D) and IFNβ mRNA (E-H) were assayed (n=3, data expressed as means±SD, *P<0.05 versus DMSO group, ANOVA LSD test).

Pharmacologic inhibition of ALK blocks STING activation: As secretory cells, monocytes and macrophages are vital to the regulation of immune responses and the development of inflammation (23). However, little information is available concerning the expression and activity of ALK in innate immune cells. We observed that ALK was abundantly expressed in primary or immortalized monocytes and macrophages (iBMDMs, pPMs, pPBMCs; RAW264.7, J774A.1, and THP1 cells) from mice or humans (FIG. 3 (A)). Functionally, all three ALK inhibitors (AZD3463, LDK378, and AP26113) from a target-selective inhibitory library diminished 3'3'-cGAMP-induced IFNβ release in iBMDMs (FIG. 3 (B)). With respect to the tumor-killing activity of ALK inhibitors (24), we addressed whether AZD3463, LDK378, and AP26113 inhibit STING activation in macrophages through triggering cell death. AZD3463 exhibited cytotoxicity against iBMDMs, pPMs, and RAW264.7 and THP1 cells (FIG. 3 (C)). In contrast, LDK378 and AP26113 did not affect cell viability in these cells (FIG. 3 (C)), suggesting that the suppressive effect of LDK378 and AP26113 on STING activation in innate immune cells was not dependent on their cytotoxic capacities. In addition to 3'3'-cGAMP, a number of natural or enzymatically-synthesized STING ligands (2'3'-cGAMP, 2'2'-cGAMP, cyclic dimeric adenosine monophosphate [c-di-AMP], cyclic dimeric guanosine monophosphate [c-di-GMP], cyclic di-inosine monophosphate [c-di-IMP], and 5,6-dimethylxanthenone-4-acetic acid [DMXAA]) with different structures also induce type I IFNs. Both LDK378 and AP26113 inhibited IFNβ release induced by these different STING ligands in iBMDMs (FIGS. 4A (A) and (B)), RAW264.7 cells (FIG. 4A (B) and FIG. 5 (A)), J774A.1 cells (FIG. 4A (B) and FIG. 5 (B)), THP1 cells (FIG. 4A (B) and FIG. 5 (C)), or pPMs (FIG. 4A (B) and FIG. 5 (D)). Of note, only DMXAA (also known as vadimezan or ASA404) targets the STING pathway in a mouse-specific manner (FIG. 5 (C)). Consistent with their inhibition of IFNβ protein release, pharmacologic inhibition of ALK by LDK378 and AP26113 also resulted in the attenuation of STING ligand-induced IFNβ mRNA expression in iBMDMs (FIGS. 4A (C) and (D)), RAW264.7 cells (FIG. 4A (D) and FIG. 5 (E)), J774A.1 cells (FIG. 4A (D) and FIG. 5 (F)), THP1 cells (FIG. 4A (D) and FIG. 5 (G)), or pPMs (FIG. 4A (D) and FIG. 5(H)). Thus, ALK seems to play an important role in the regulation of STING pathway activation in response to a wide array of STING ligands.

Figure 4B:
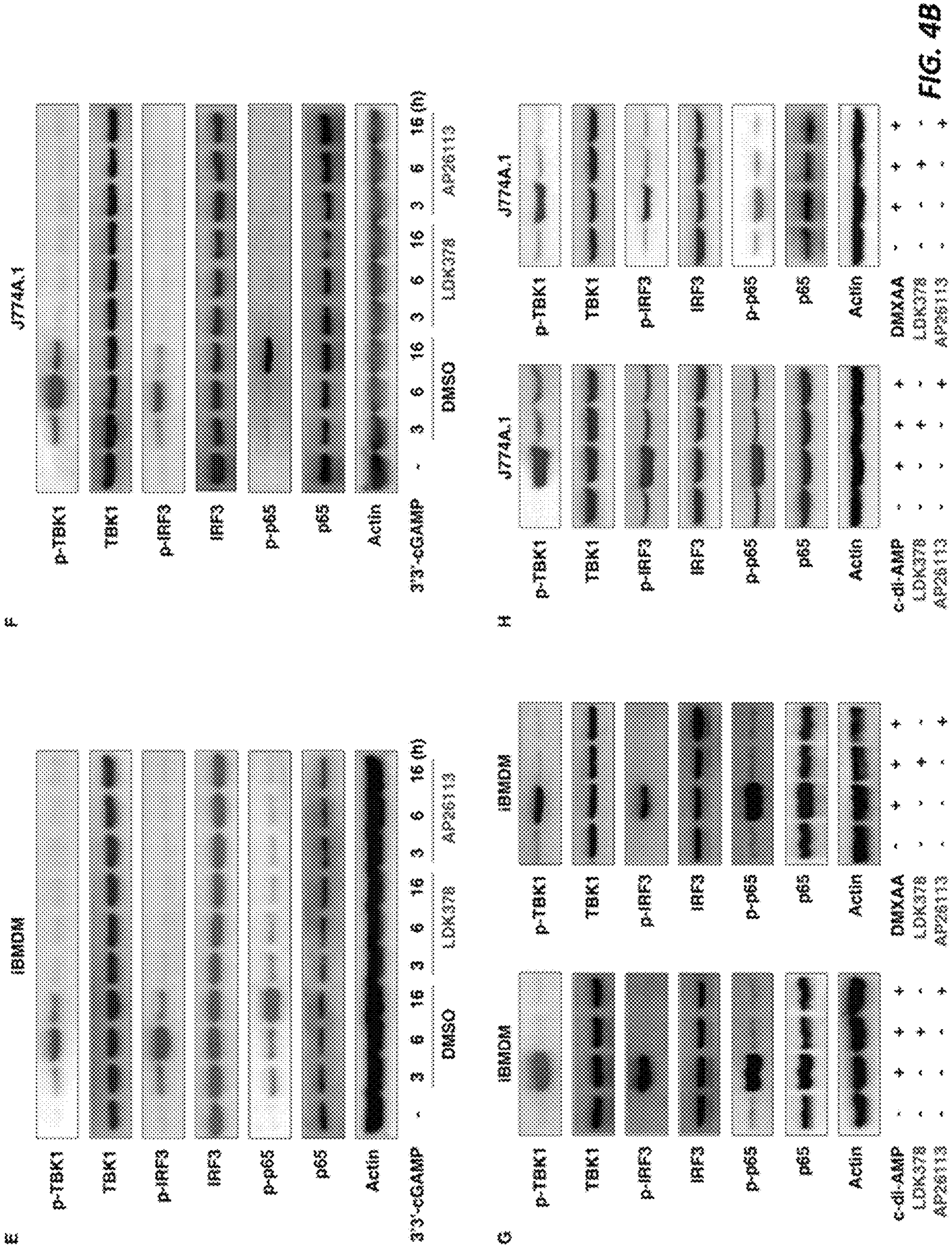
Figure 6:
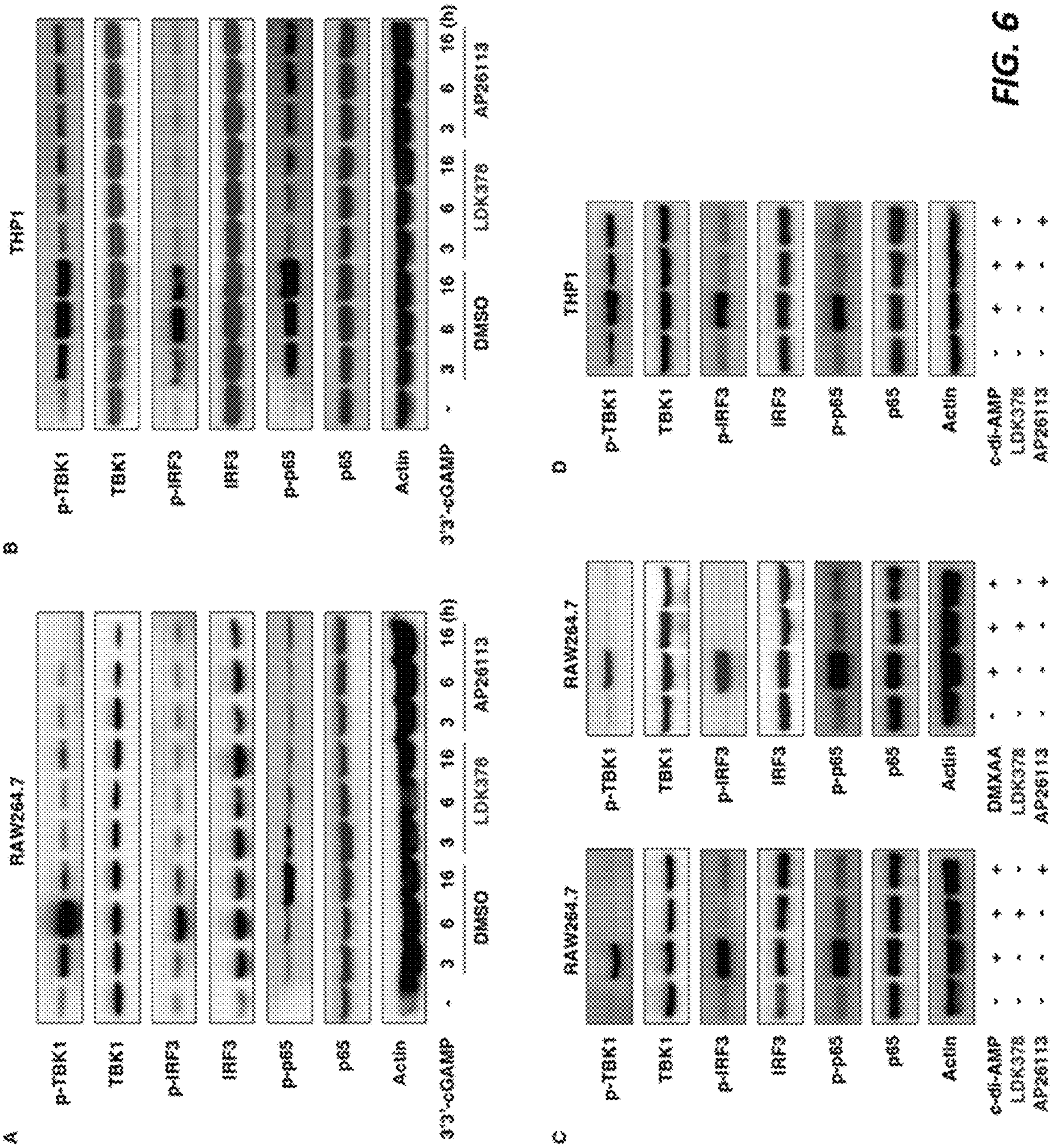
FIG. 6. Pharmacologic inhibition of ALK blocks STING activation. (A, B) Western blot analysis of indicated protein expression in RAW264.7 (A) or THP1 (B) cells following 3'3'-cGAMP (10 μg/ml) treatment with or without LDK378 (10 μM), AP26113 (10 μM), or vehicle (DMSO) for three to 16 hours. (C, D) Western blot analysis of indicated protein expression in RAW264.7 (C) or THP1 (D) cells following c-di-AMP (10 μg/ml) or DMXAA (10 μg/ml) treatment with or without LDK378 (10 μM), AP26113 (10 μM), or vehicle (DMSO) for 16 hours.

A common event in STING activation by different ligands is the phosphorylation of TBK1 (p-TBK1). We therefore examined the effect of ALK inhibition on the expression and phosphorylation of TBK1. Both LDK378 and AP26113 time-dependently reduced 3'3'-cGAMP-induced p-TBK1, but not total TBK1, in iBMDMs (FIG. 4B (E)), J774A.1 (FIG. 4B (F)), RAW264.7 (FIG. 6 (A)), and THP1 (FIG. 6 (B)) cells. Similar to 3'3'-cGAMP, LDK378 and AP26113 also inhibited c-di-AMP- or DMXAA-induced p-TBK1, but not total TBK1, in iBMDMs (FIG. 4B (G)), J774A.1 (FIG. 4B (H)), RAW264.7 (FIG. 6 (C)), and THP1 (FIG. 6 (D)) cells. Direct downstream targets of p-TBK1 include phosphorylation of IRF3 (p-IRF3) and NF-κB (p-p65). Both LDK378 and AP26113 also inhibited 3'3'-cGAMP-, c-di-AMP-, and DMXAA-induced p-IRF3 and p-p65 in iBMDMs (FIGS. 4B (E) and 4G), J774A.1 (FIGS. 4B (F) and (H)), RAW264.7 (FIGS. 6 (A) and 6 (C)), and THP1 cells (FIGS. 6 (B) and 6 (D)). These results strongly suggest that pharmacologic inhibition of ALK blocks STING pathway activation through interfering with TBK1-mediated signaling transduction in monocytes and macrophages.

Figure 7A:
FIGS. 7A-7I. Genetic silencing of ALK limits STING activation.
Figure 8A:
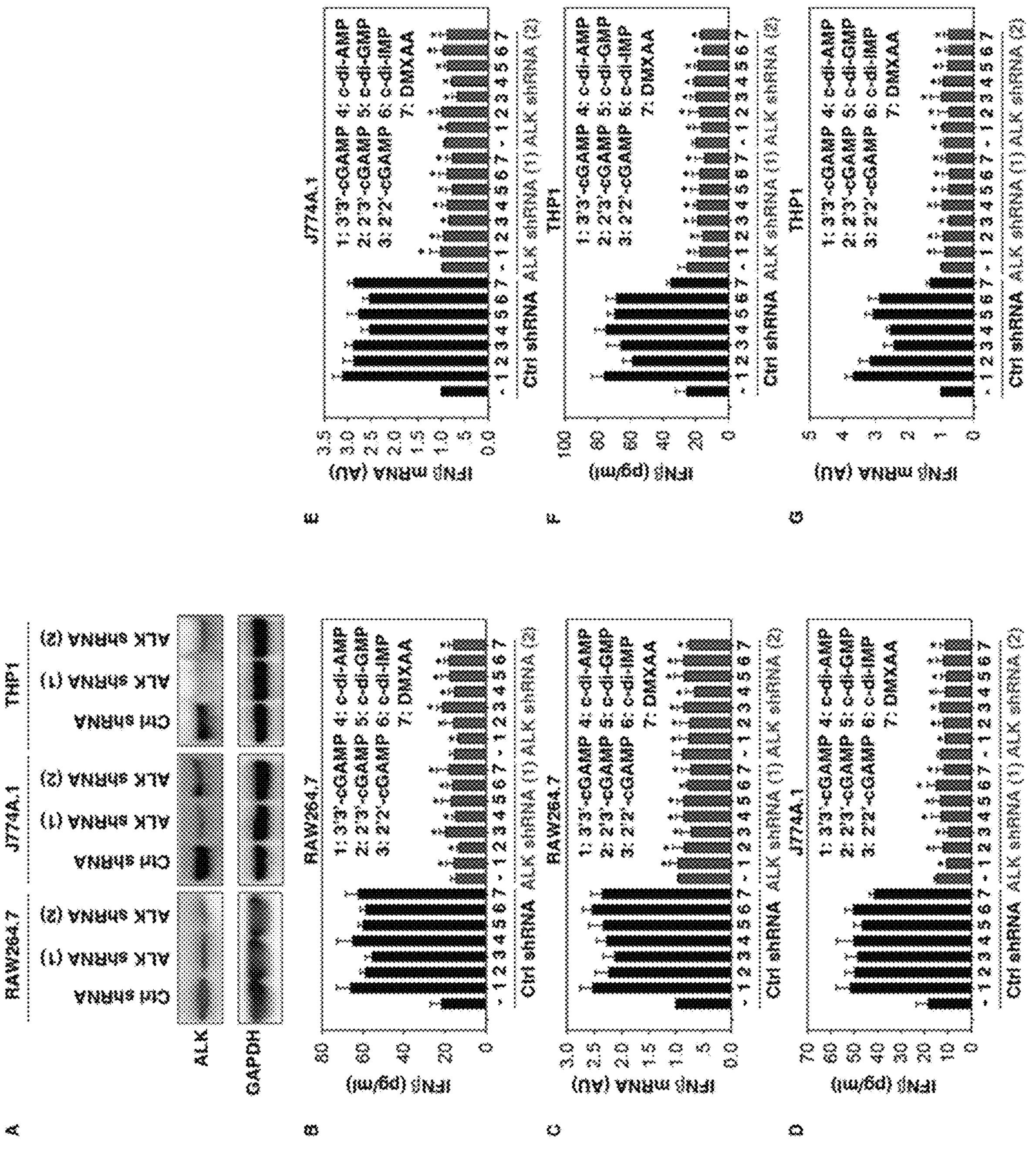
FIGS. 8A and 8B. Genetic inhibition of ALK limits STING activation. (A) Western blot analysis of ALK expression in ALK stable knockdown cells (RAW264.7, J744A.1, and THP1). (B-G). Indicated RAW264.7, J744A.1, and THP1 cells were treated with indicated STING ligands (10 μg/ml) for 16 hours. IFNβ release (B, D, F) and IFNβ mRNA (C, E, G) were assayed (n=3, data expressed as means±SD, *P<0.05 versus control shRNA group, ANOVA LSD test). (H-J) Western blot analysis of indicated protein expression in ALK-WT and ALK-knockdown RAW264.7 (H), J744A.1 (I), and THP1 (J) cells following treatment with 3'3'-cGAMP (10 μg/ml), c-di-AMP (10 μg/ml), or DMXAA (10 μg/ml) for 16 hours.

Genetic inhibition of ALK limits STING activation: Because pharmacological inhibitors often have undesirable off-target effects, we thus determined whether ALK gene knockdown has a similar impact on STING activation. We generated stable ALK knockdown macrophages using two different specific short hairpin RNA (shRNAs) and achieved 85%~95% ALK knockdown after antibiotic selection in iBMDMs (FIG. 7A), RAW264.7 (FIG. 8A), J774A.1 (FIG. 8A), and THP1 (FIG. 8A) cells, as confirmed using western blot analysis.

Figure 7B:
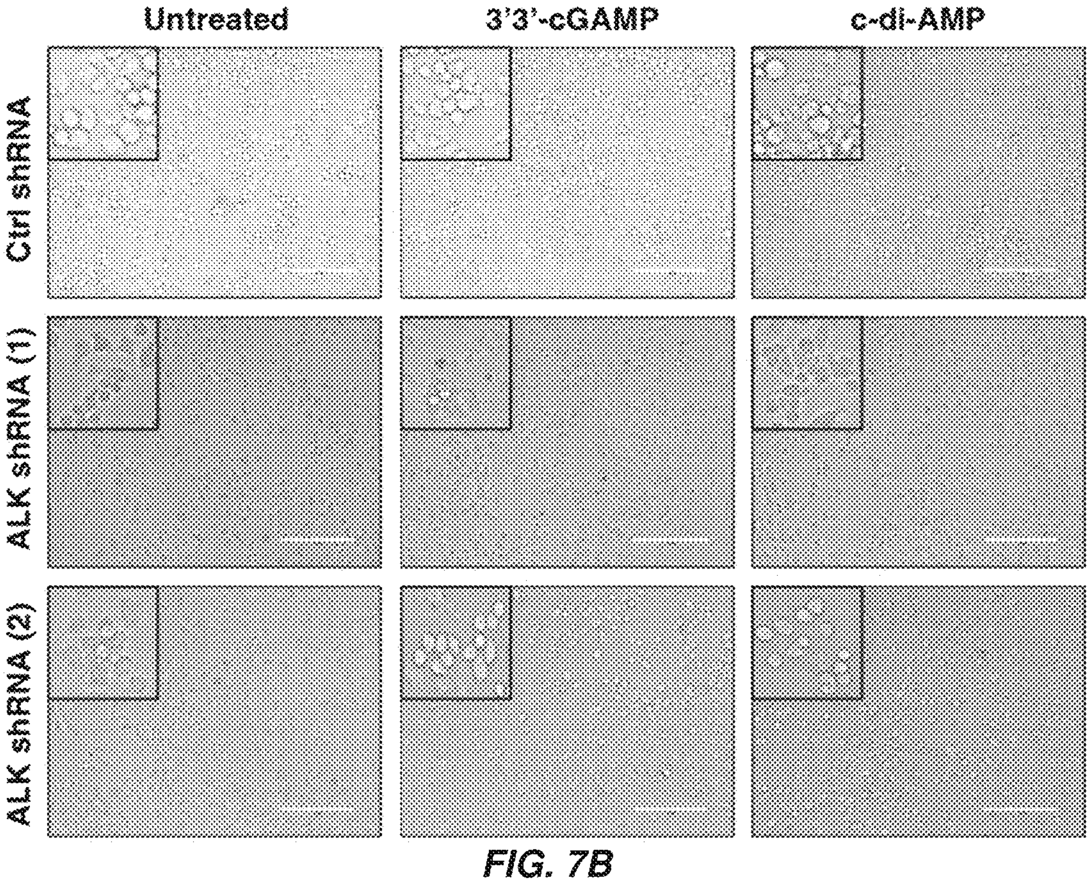
Figure 7C:
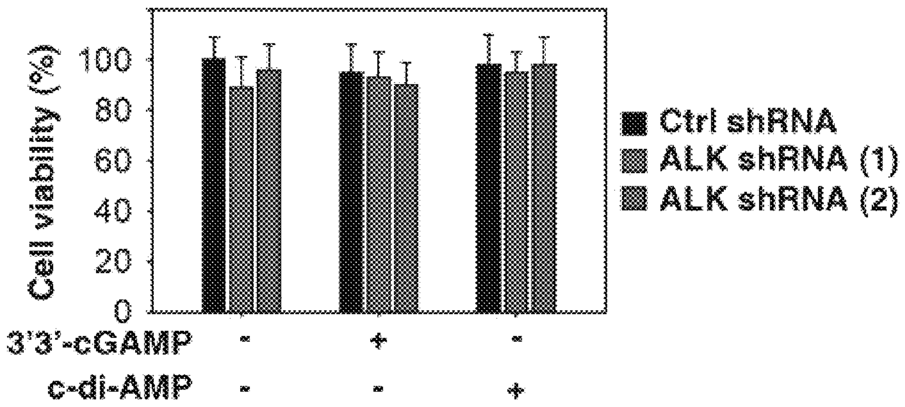
Figure 7D:
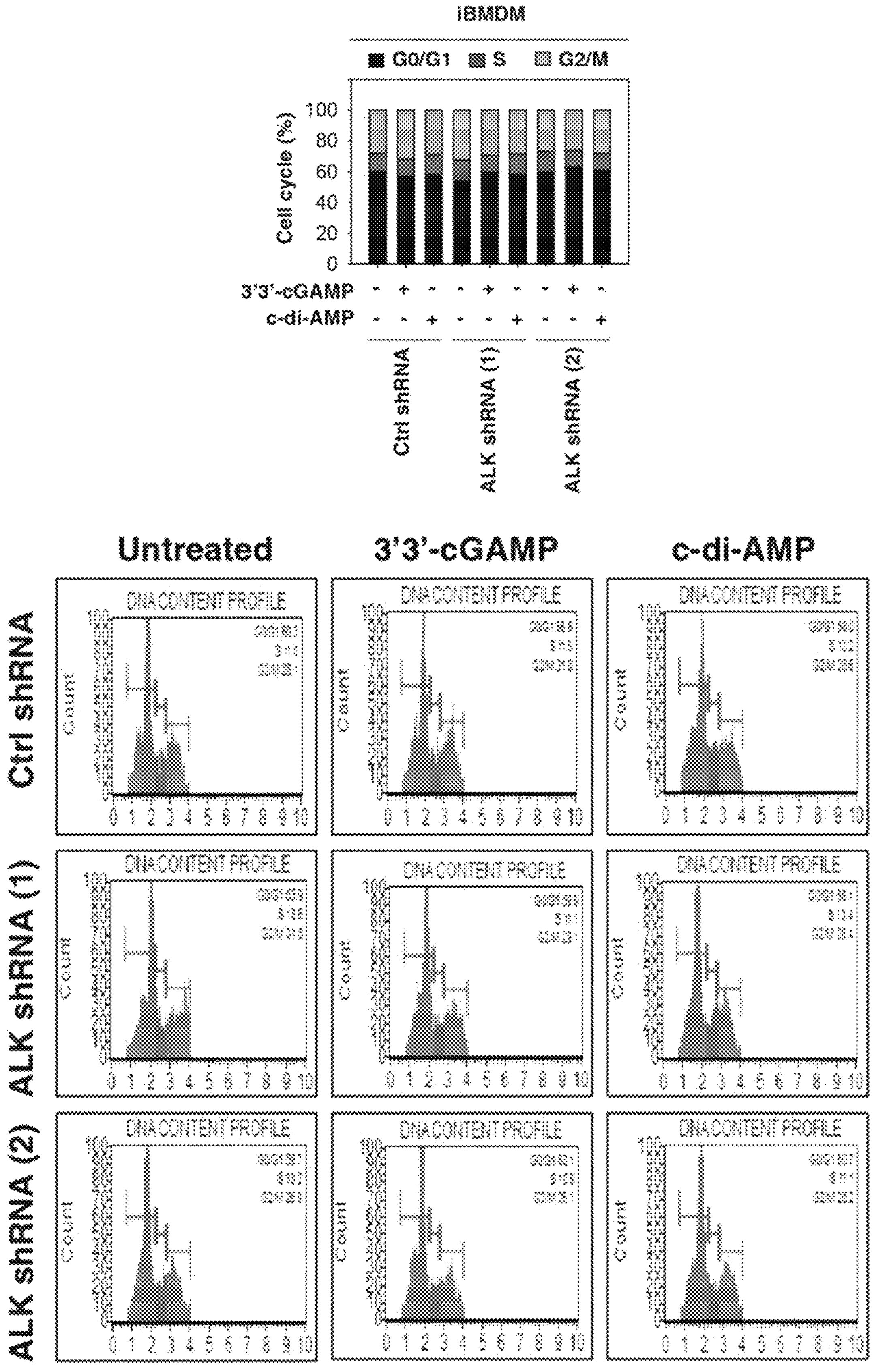
Figure 7E:
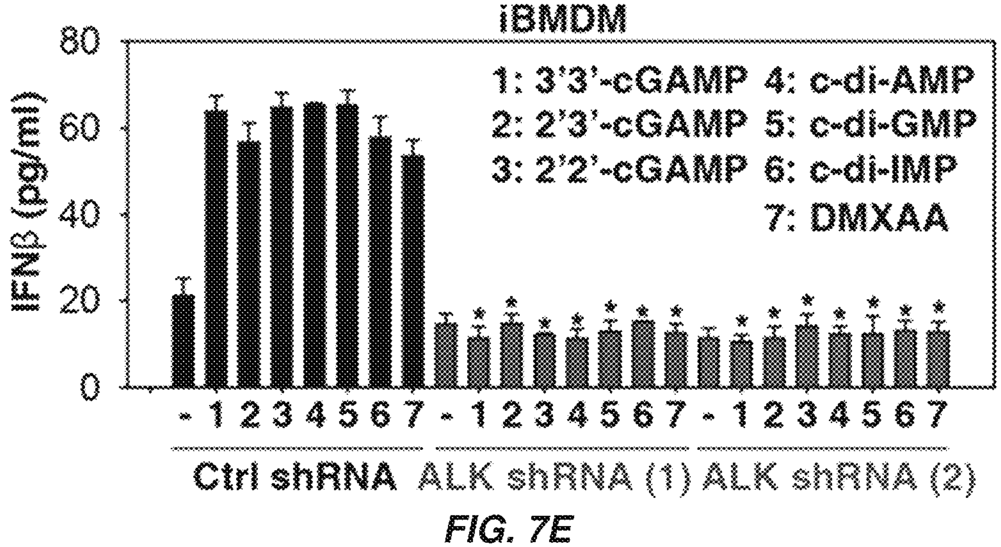
Figure 7F:
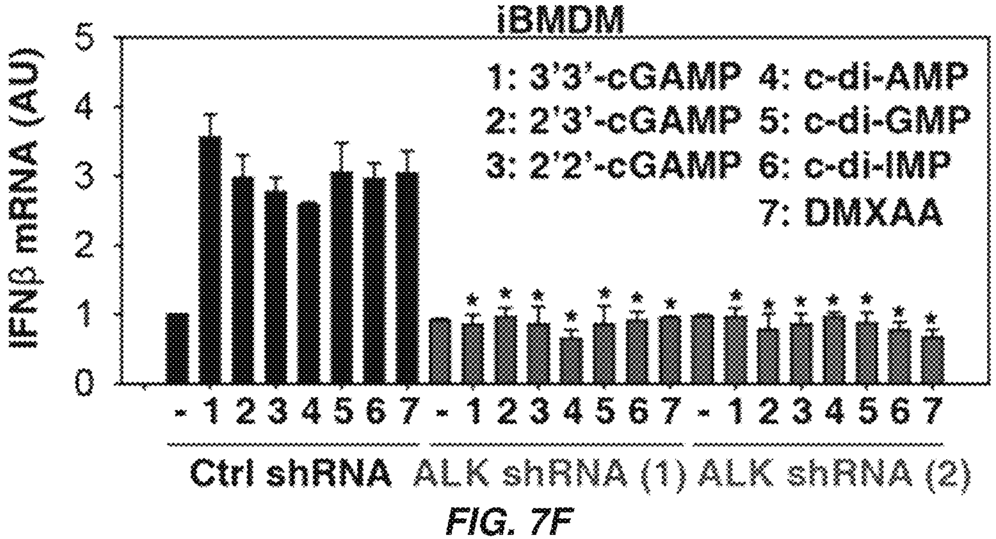
Figure 7G:
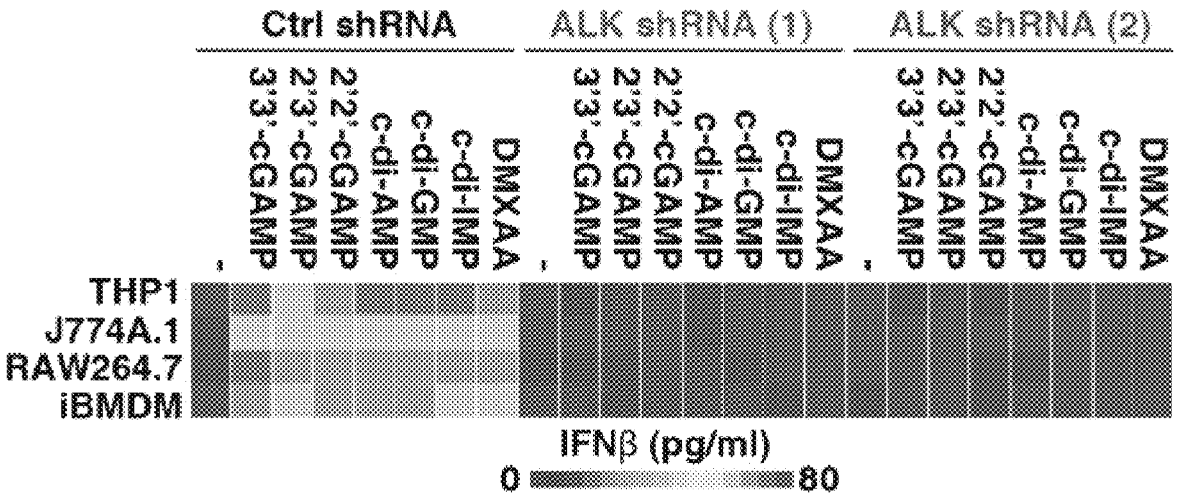
Figure 7H:
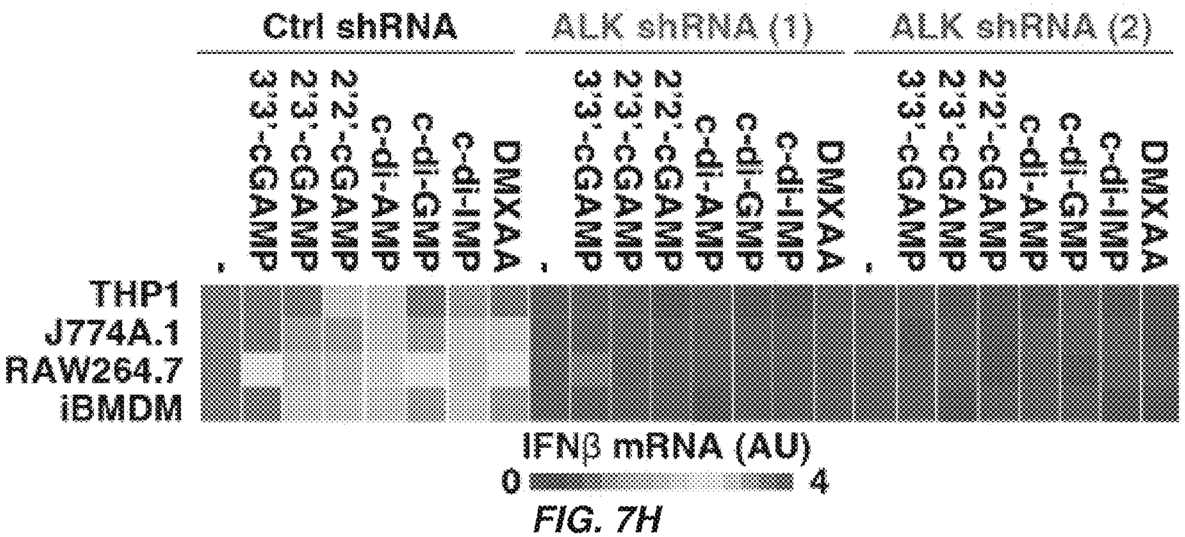
Figure 7I:
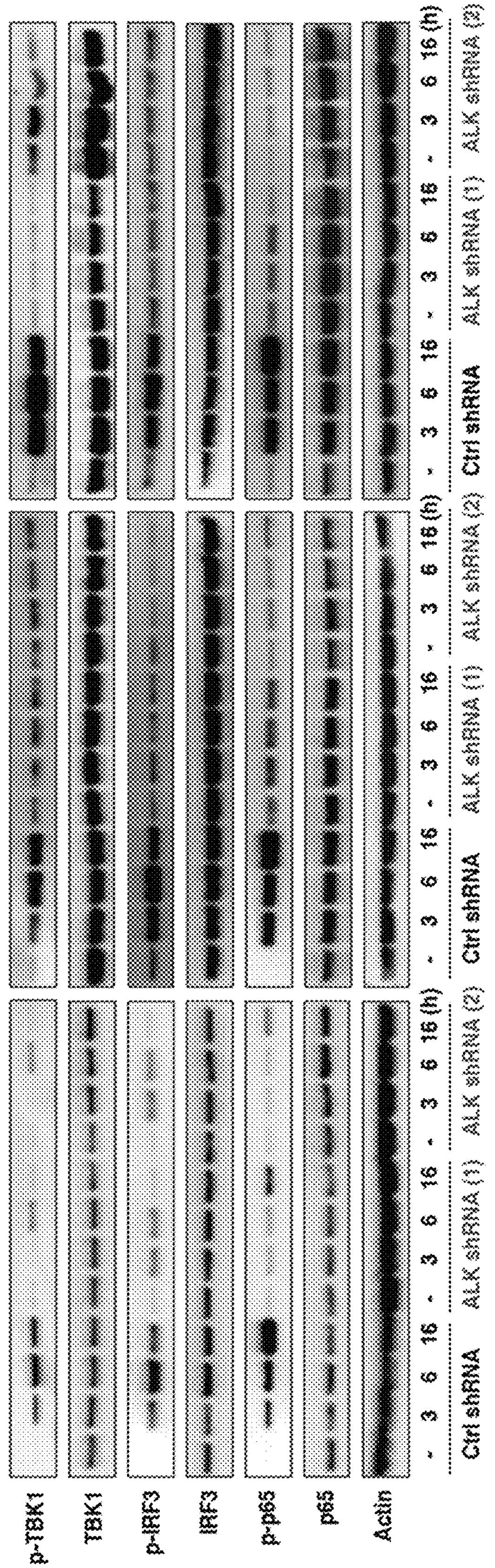
Figure 8B:
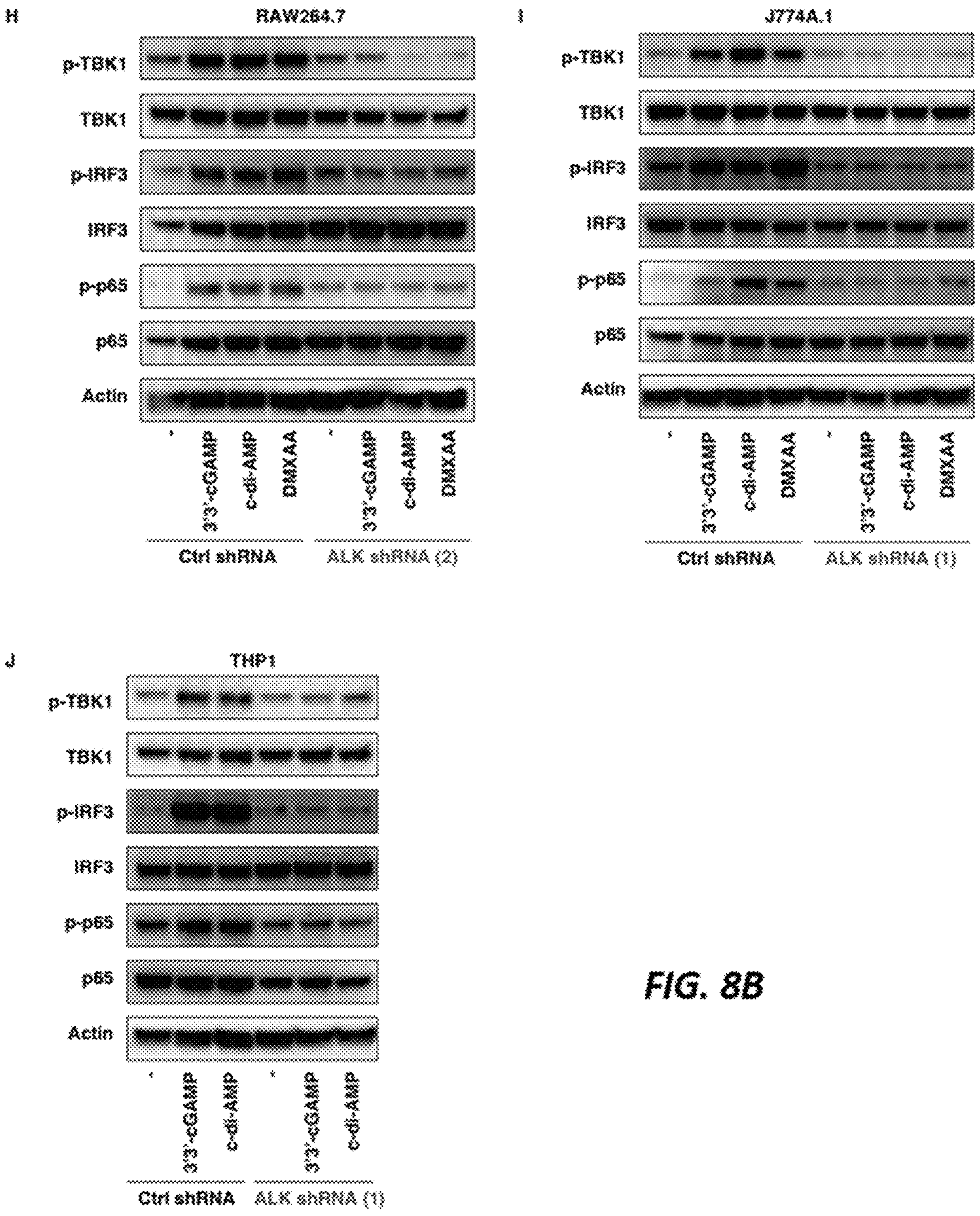

As aforementioned, different ALK inhibitors exhibit divergent impacts on macrophage cell viabilities. To assess this behavior, we carefully analyzed cell morphology, cell viability, and cell proliferation with or without STING ligand (3'3'-cGAMP and c-di-AMP) treatment in ALK knockdown iBMDMs. Like control shRNA cells, these ALK knockdown iBMDM cell lines were not associated with a change in cell morphology (FIG. 7B), cell viability (FIG. 7C), and cell cycle (FIG. 7D) after treatment with 3'3'-cGAMP and c-di-AMP, suggesting that ALK depletion may not lead to macrophage death upon STING activation. Similar to pharmacological ALK inhibition, genetic inhibition of ALK by shRNA also attenuated STING ligand (3'3'-cGAMP, 2'3'-cGAMP, 2'2'-cGAMP, c-di-AMP, c-di-GMP, c-di-IMP, and DMXAA)-induced IFNβ expression and release in iBMDMs (FIG. 7E-7H), RAW264.7 (FIG. 7G-7H and FIG. 8A (B, C)), J774A.1 (FIG. 7G-7H and FIG. 8A (D, E)), and THP1 (FIG. 7G-7H and FIG. 8A (F, G) cells, indicating that ALK expression is required for STING activation. To corroborate these findings, we further examined protein phosphorylation of key STING signaling molecules in ALK knockdown and control cells. Consistent with pharmacologic inhibition of ALK by LDK378 and AP26113, genetic suppression of ALK expression also reduced 3'3'-cGAMP-, c-di-AMP-, and DMXAA-induced p-TBK1, p-IRF3, and p-p65 in iBMDMs (FIG. 7I), RAW264.7 (FIG. 8B (H)), J774A.1 (FIG. 8B (I)), and THP1 (FIG. 8B (J)) cells. These data strongly support ALK as an important regulator of activation of the STING signaling pathway.

Figure 9A:
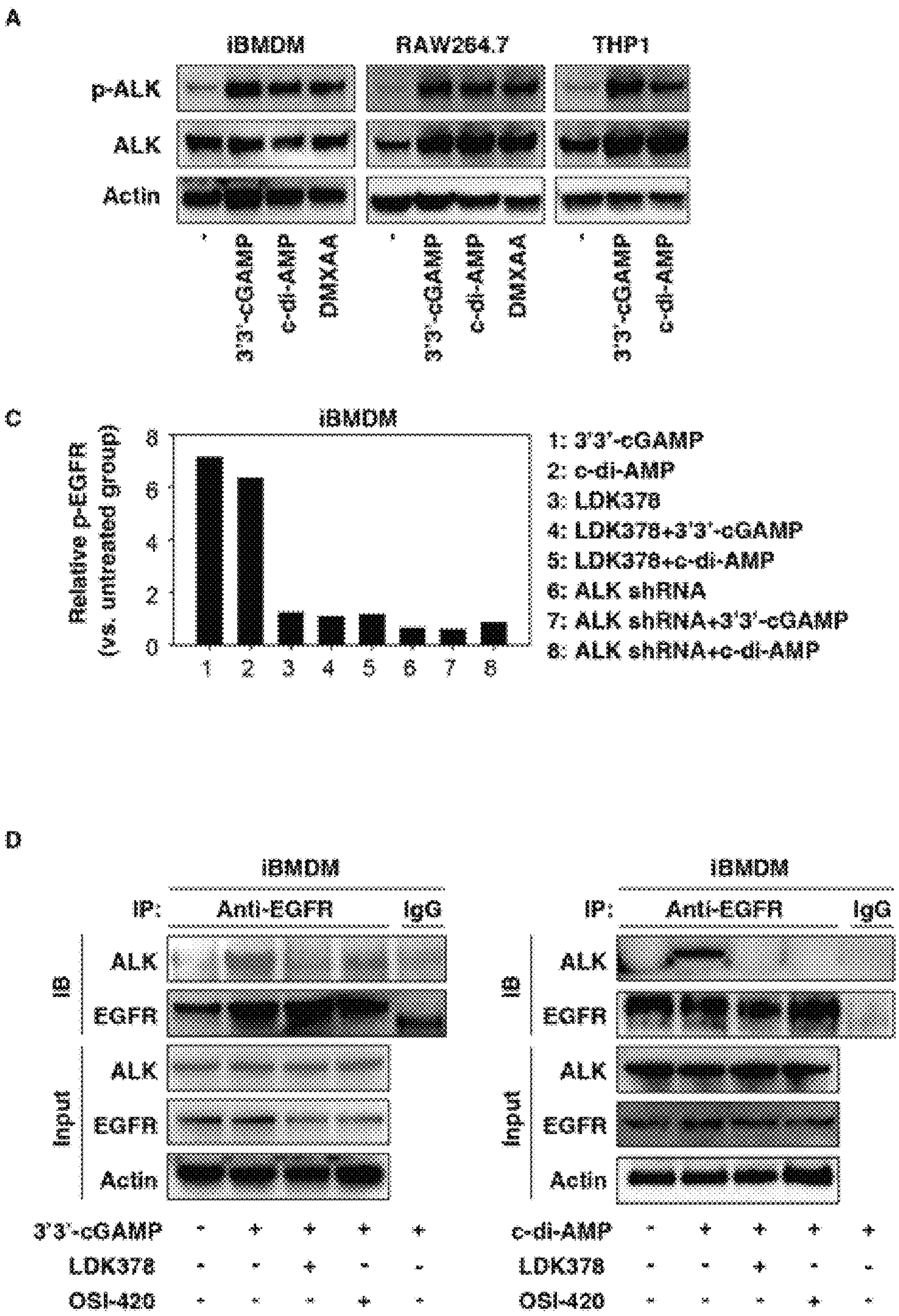

ALK-EGFR-AKT pathway promotes STING activation: It has been suggested that the phosphorylation of ALK (p-ALK) at Tyr1078 is required for its activation in tumor cells. To determine whether ALK is similarly phosphorylated by STING ligands in innate immune cells, we analyzed the expression of p-ALK and ALK in iBMDMs and RAW264.7 and THP1 cells after STING activation. Expression of p-ALK (but not total ALK) was enhanced in these cells by 3'3'-cGAMP, c-di-AMP, and DMXAA (FIG. 9A (A)), suggesting that ALK is possibly activated by a wide array of STING ligands.

Figure 10:
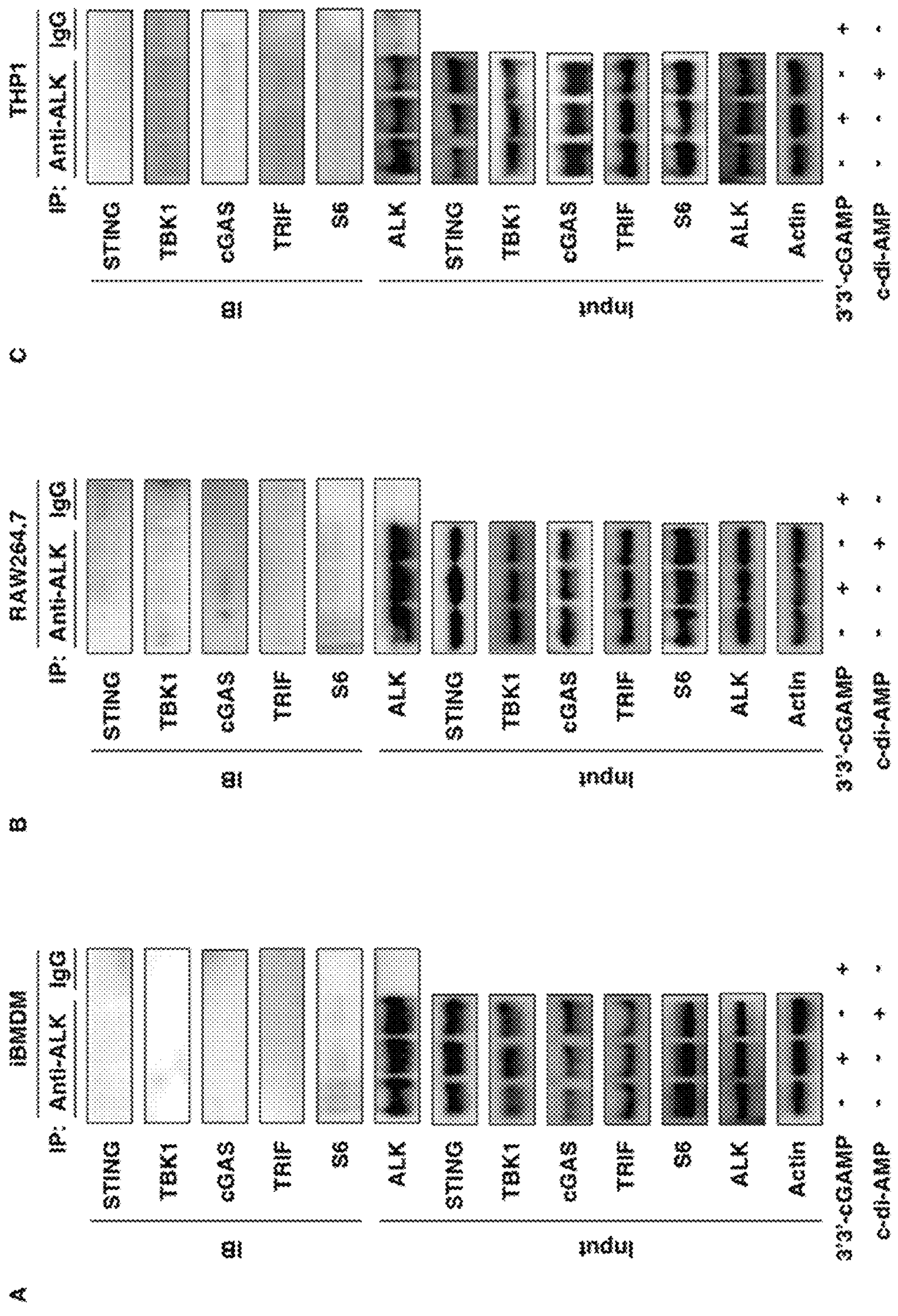
FIG. 10. ALK does not bind known STING regulators. IP analysis of the interaction between ALK and indicated proteins in iBMDMs (A) and RAW264.7 (B) and THP1 (C) cells following 3'3'-cGAMP (10 μg/ml) or c-di-AMP (10 μg/ml) treatment for 16 hours.

To elucidate the possible role of ALK in the regulation of the STING signaling pathway, we tested whether ALK promotes the phosphorylation of core components of the STING pathway (STING, TBK1, and cGAS) through protein-protein interaction using co-immunoprecipitation techniques. We did not observe a direct interaction between ALK and these cytosolic signaling molecules in iBMDMs (FIG. 10 (A)) and RAW264.7 (FIG. 10 (B)) and THP1 cells (FIG. 10 (C)) after treatment with 3'3'-cGAMP and c-di-AMP. Immunoprecipitation (IP) analysis also did not reveal evidence of ALK binding to other recently-identified cytosolic STING-interacting partners such as TIR-domain-containing adapter-inducing interferon-β (TRIF) or the ribosomal protein S6 kinase (FIG. 10 (A-C)). These findings suggest that ALK-mediated STING activation may not be dependent on direct binding to known cytosolic regulators of the STING pathway in macrophages and monocytes.

Figure 9B:
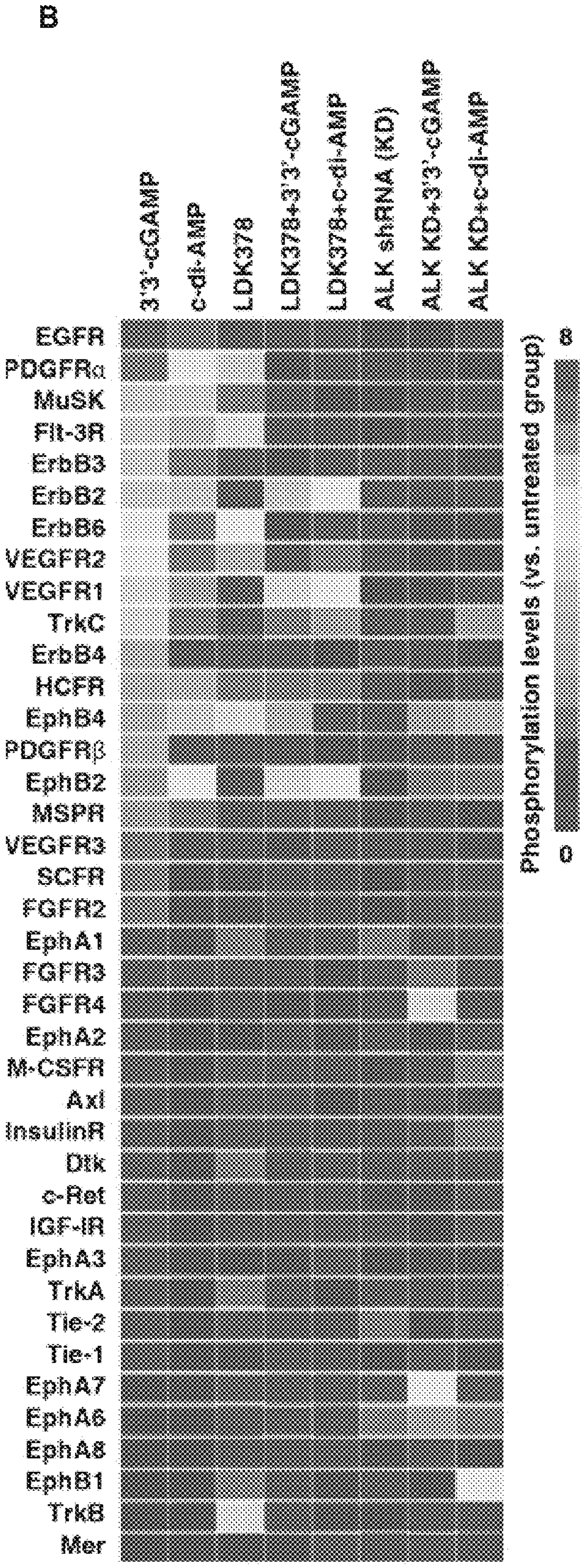
Figure 11:
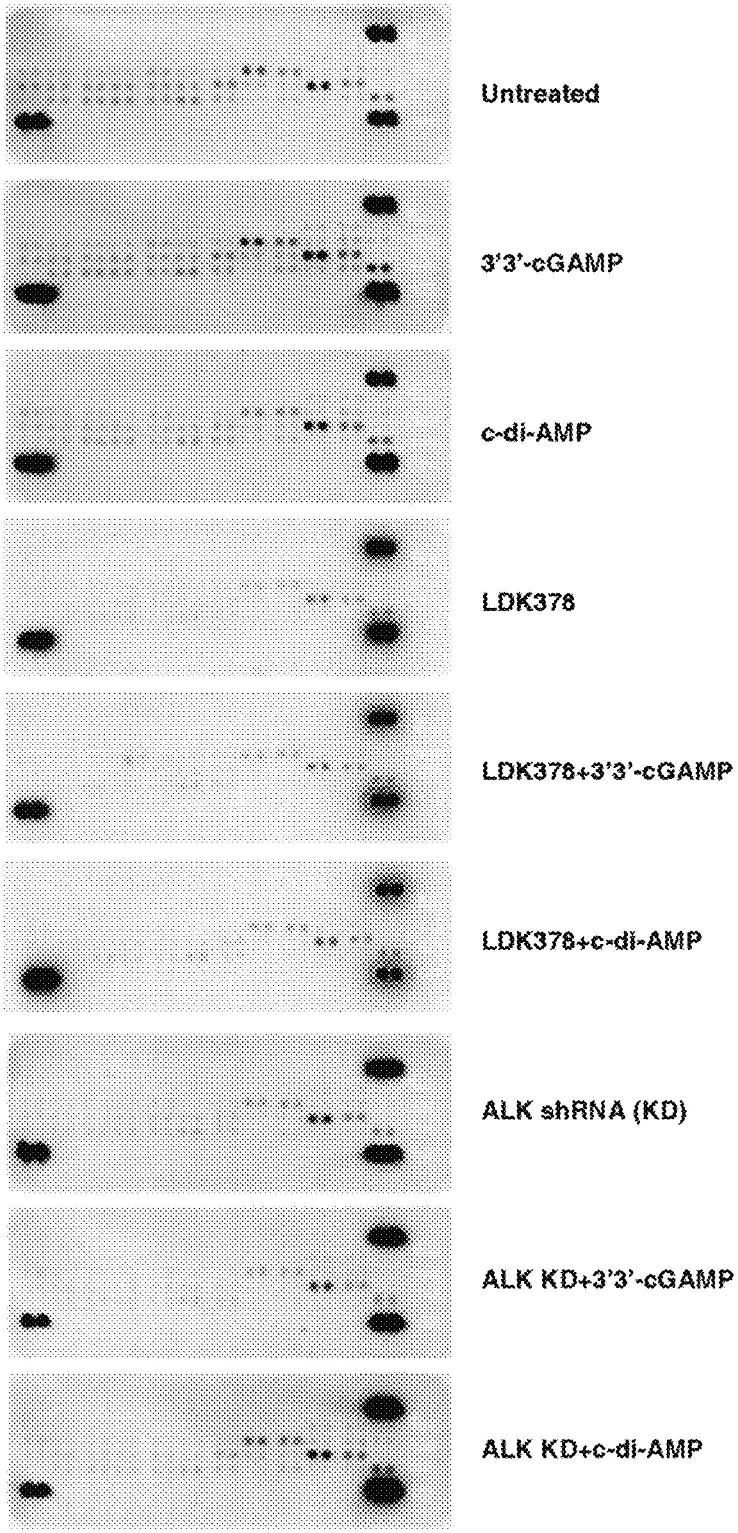
FIG. 11. Inhibition of ALK limits receptor tyrosine kinase phosphorylation in STING activation. Proteome Profiler Antibody Arrays analysis of receptor tyrosine kinase phosphorylation in iBMDMs following 3'3'-cGAMP (10 μg/ml) or c-di-AMP (10 μg/ml) treatment for 16 hours with or without pharmacologic (LDK378, 10 μM) or genetic inhibition of ALK.

It is still possible that ALK, a member of the receptor tyrosine kinases (RTKs), may interact with other RTKs in the cell surface to mediate signal transduction into the cytoplasm under STING activation. To test this possibility, we used a proteome profiler antibody array to survey the phosphorylation of 49 RTKs in iBMDMs after stimulation with 3'3'-cGAMP or c-di-AMP. The phosphorylation of certain RTKs was changed by exposure to 3'3'-cGAMP and c-di-AMP (FIG. 9B (B) and FIG. 11). Among them, the phosphorylation of epidermal growth factor receptor (EGFR) was upregulated by 3'3'-cGAMP and c-di-AMP (FIG. 9A (C) and FIG. 11), whereas LDK378 or knockdown of ALK impaired the STING ligand-induced upregulated phosphorylation of various RTKs, including EGFR, in iBMDMs (FIG. 9A (C) and FIG. 11). These data suggest that RTK phosphorylation might be widely implicated in the STING pathway.

Figure 9C:
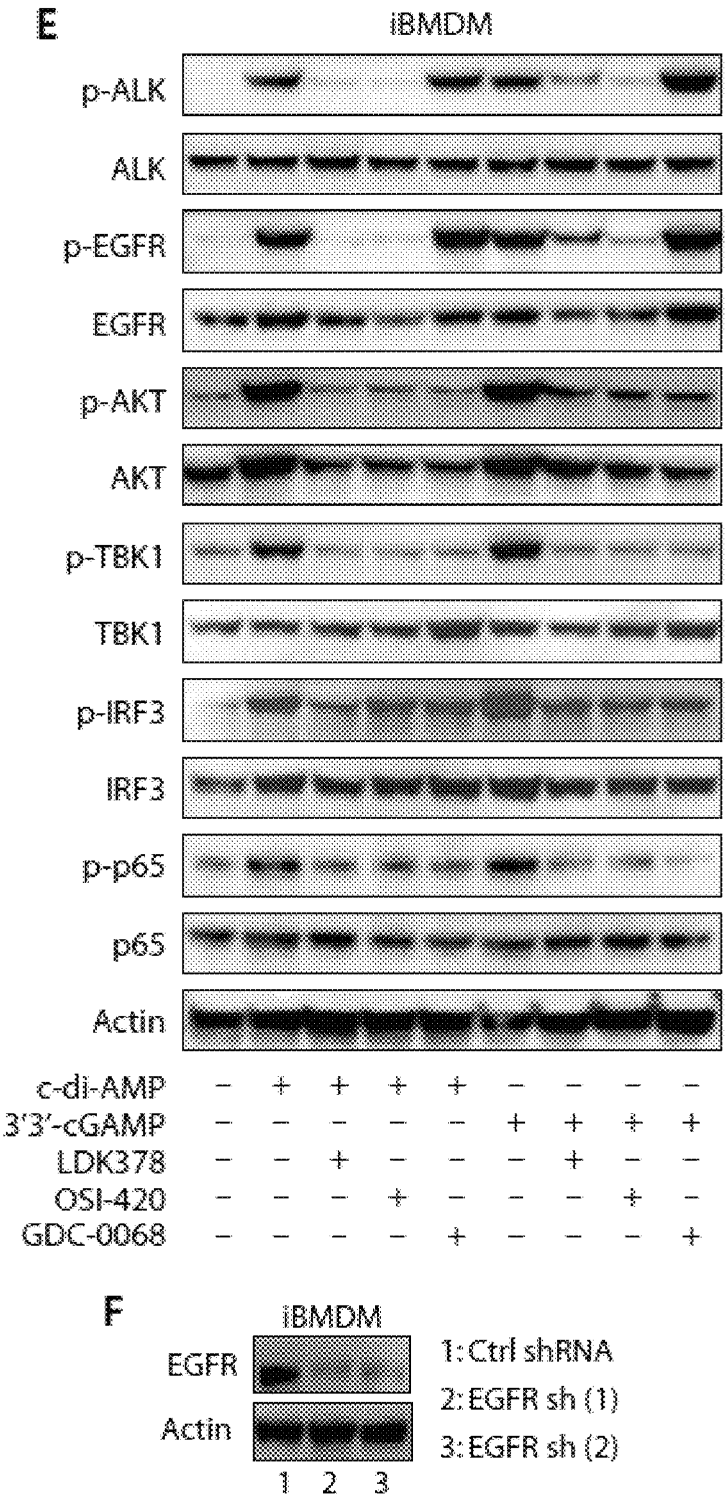
Figure 12:
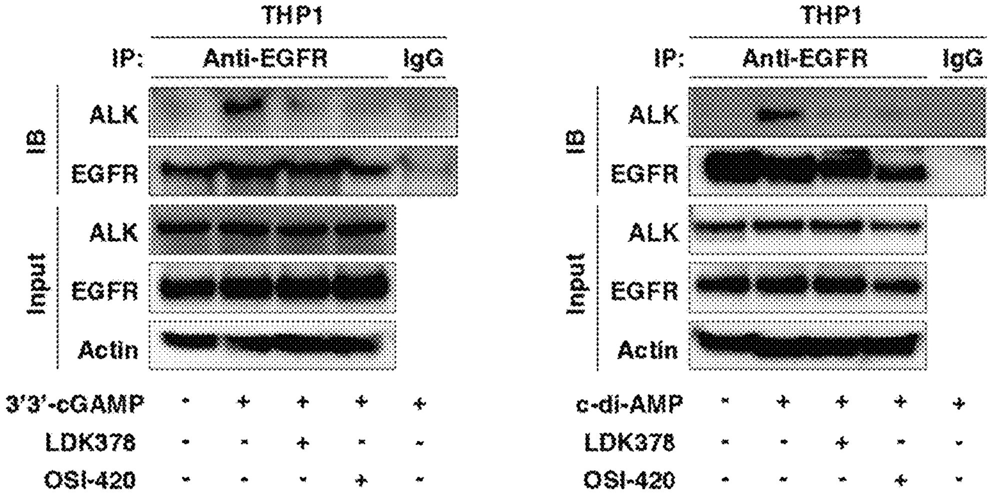
FIG. 12. ALK binds EGFR during STING activation. IP analysis of the interaction between ALK and EGFR in THP1 cells following 3'3'-cGAMP (10 μg/ml, left) or c-di-AMP (10 μg/ml, right) treatment for 16 hours with or without LDK378 (10 μM) or OSI-420 (10 μM).
Figure 13:
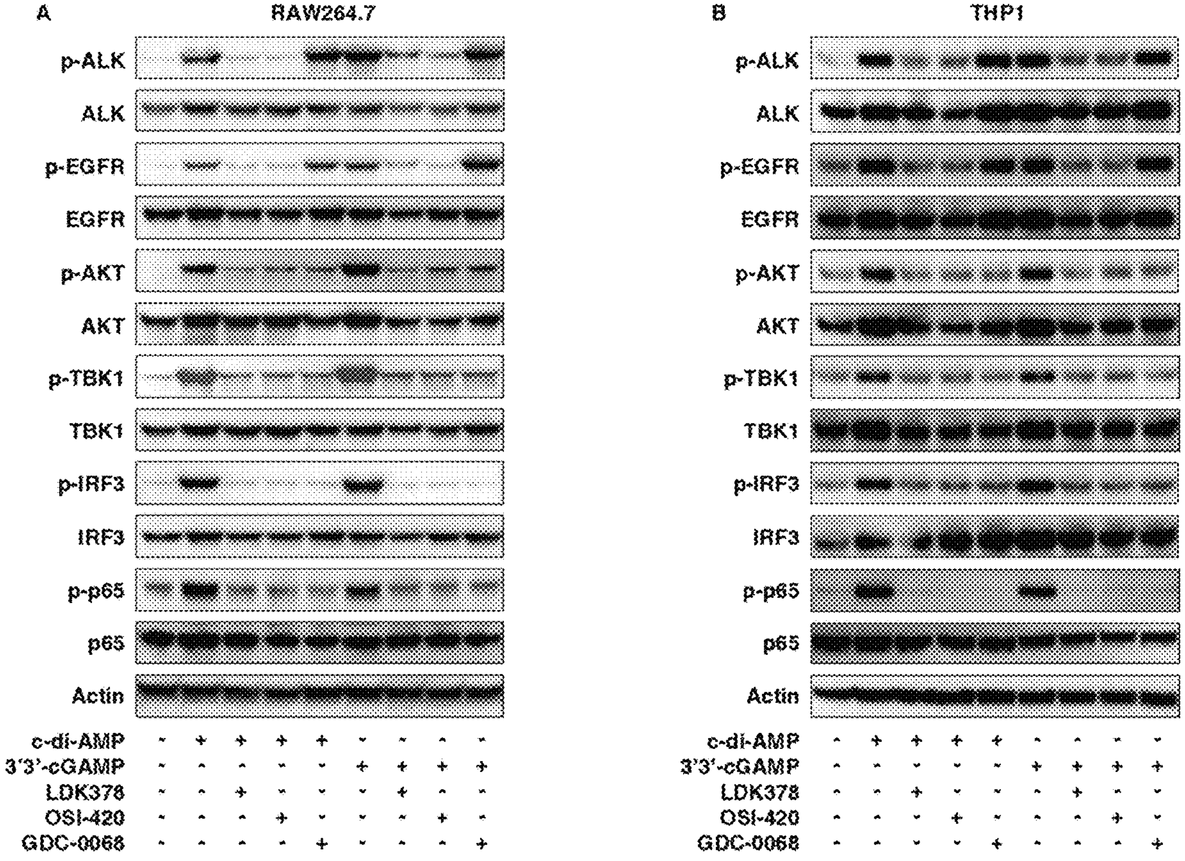
FIG. 13. ALK-EGFR-AKT pathway mediates STING activation. Western blot analysis of indicated protein expression in RAW264.7 (A) or THP1 (B) cells following treatment with 3'3'-cGAMP (10 μg/ml) or c-di-AMP (10 μg/ml) for 16 hours with or without LDK378 (10 μM), OSI-420 (10 μM), or GDC-0068 (10 μM).
Figure 14:
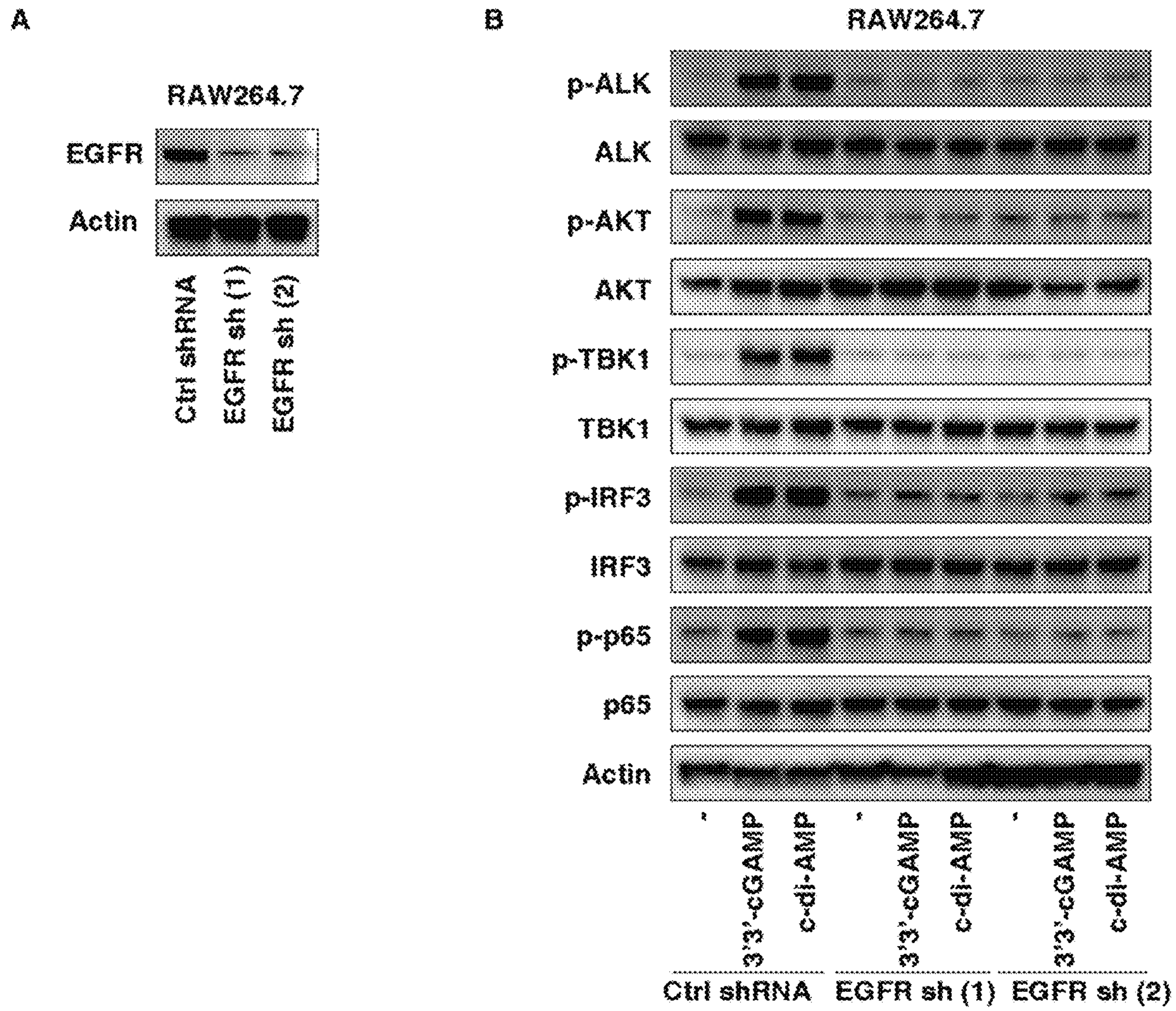
FIG. 14. Knockdown of EGFR inhibits STING activation. (A) Western blot analysis of EGFR expression in EGFR stable knockdown RAW264.7 cells. (B) Western blot analysis of indicated protein expression in EGFR-WT and EGFR-knockdown RAW264.7 cells following treatment with 3'3'-cGAMP (10 μg/ml) or c-di-AMP (10 μg/ml) for 16 hours.
Figure 15:
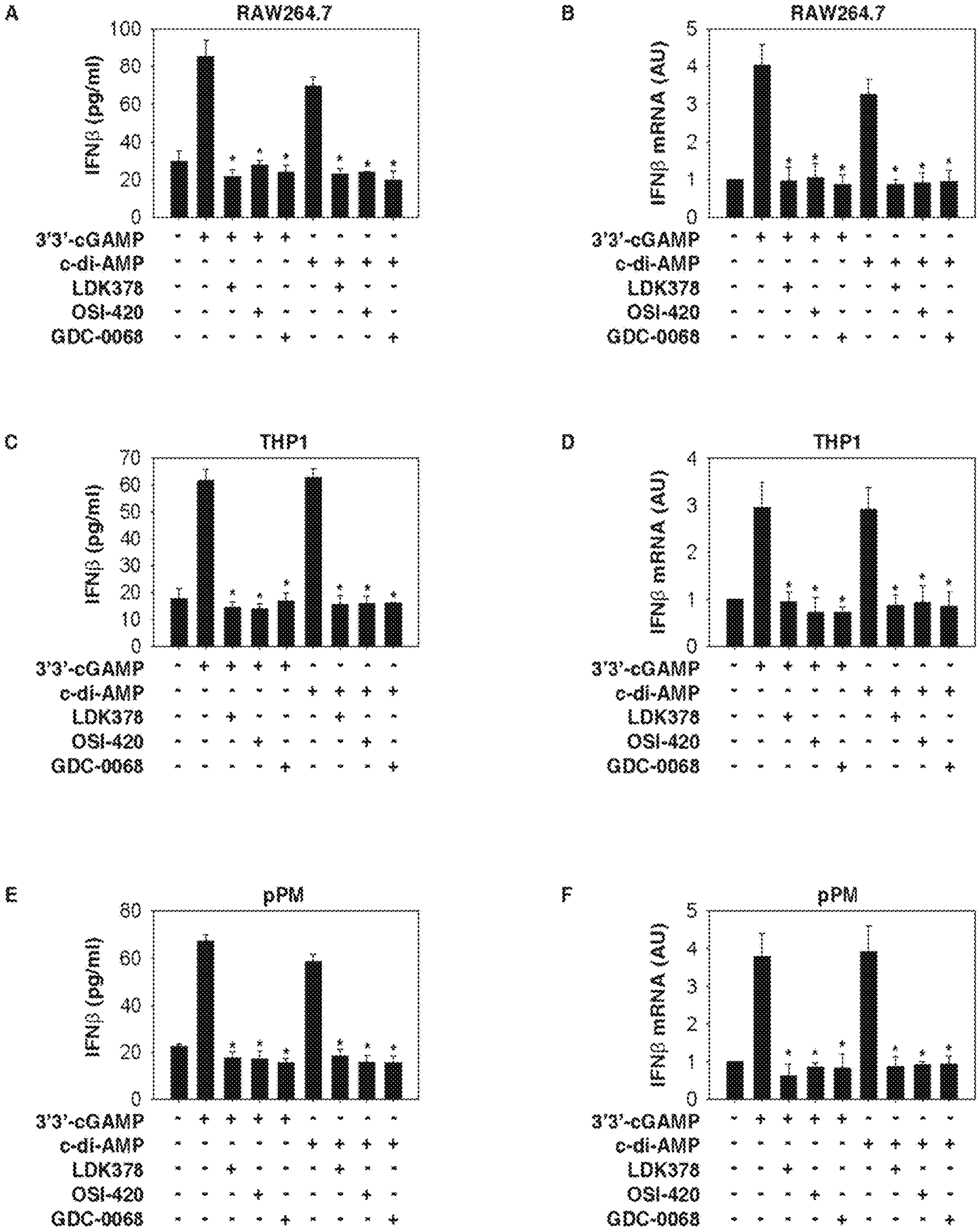
FIG. 15. The ALK-EGFR-AKT pathway mediates STING ligand-induced IFNβ release and expression. RAW264.7, THP1, and pPM cells were treated with 3'3'-cGAMP (10 μg/ml) or c-di-AMP (10 μg/ml) for 16 hours with or without LDK378 (10 μM), OSI-420, (10 μM), or GDC-0068 (10 μM). IFNβ release (A, C, E) and IFNβ mRNA (B, D, F) were assayed (n=3, data expressed as means±SD, $^*P<0.05$ versus 3'3'-cGAMP or c-di-AMP group, ANOVA LSD test).

Previous observation demonstrated that the interplay between ALK and EGFR coordinately regulates AKT phosphorylation to promote tumor growth. We therefore tested whether the ALK-EGFR-AKT pathway is also a critical driver of STING activation in innate immune cells. First, the interaction between ALK and EGFR was found to be increased in iBMDMs (FIG. 9A (D)) and THP1 (FIG. 12) cells after treatment with 3'3'-cGAMP or c-di-AMP, but was reduced by inhibitors specific for both ALK (LDK378) and EGFR (OSI-420) (FIG. 9A (D) and FIG. 12). Second, these ALK (LDK378) and EGFR (OSI-420) inhibitors also attenuated the 3'3'-cGAMP- or c-di-AMP-induced phosphorylation of ALK, EGFR, and AKT in iBMDMs (FIG. 9C (E)) and RAW264.7 (FIG. 13 (A)) and THP1 cells FIG. 13 (B)). In contrast, the pan AKT inhibitor GDC-0068 only blocked the phosphorylation of AKT, but not ALK or EGFR, in activated iBMDMs (FIG. 9C (E)) and RAW264.7 (FIG. 13 (A)) and THP1 cells (FIG. 13 (B)). Third, all inhibitors (LDK378, OSI-420, and GDC-0068) similarly diminished the STING ligand-induced phosphorylation of TBK1, IRF3, and p65 in iBMDMs (FIG. 9C (E)) and RAW264.7 (FIG. 13 (A)), and THP1 cells (FIG. 13 (B)). Fourth, the ability of EGFR and AKT to promote the phosphorylation of TBK1, IRF3, and p65 were similarly impaired by stable genetic knockdown of EGFR via two different shRNAs in iBMDMs (FIGS. 9C (F) and 9D (G)) and RAW264.7 cells (FIG. 14). Finally, pharmacologic inhibition of the ALK-EGFR-AKT pathway attenuated STING ligand (3'3'-cGAMP and c-di-AMP)-induced IFNβ release and mRNA expression in iBMDMs (FIG. 9D (H, I)), RAW264.7 (FIG. 15 (A, B)) and THP1 cells (FIG. 15 (C, D)), and pPMs (FIG. 15 (E, F)). Taken together, these data indicate that the interplay between ALK and EGFR contributes to the AKT-dependent STING activation in macrophages and monocytes.

ALK and STING regulates immune chemical release: The production and release of various immune chemicals such as cytokines, chemokines, and growth factors, as well as damage-associated molecular patterns, is generally considered a final effector during an immune response. Several clinical studies have suggested that immune chemical profiles, especially cytokines, are markers of disease severity, prognosis, and potential future therapeutic targets in patients with sepsis. Thus, to correlate symptoms with different phases of sepsis, it is important to survey the profile of multiple cytokines.

Like bacteria-derived CDN, lipopolysaccharide (LPS), the major component of the outer membrane of Gram-negative bacteria, is also a critical pathogen-associated molecular pattern (PAMP) involved in the pathogenesis of sepsis. Using a proteome profiler antibody array of 111 immune chemicals, we observed that stimulation with 3'3'-cGAMP, c-di-AMP, or LPS led to the release of different proteins from iBMDMs (FIG. 16A (A) and FIG. 17 (A)). For example, all three stimuli induced the release of TNFα, IL6, and serpin-E1/PAI-1 (FIG. 16B (B)), whereas only 3'3'-cGAMP and c-di-AMP markedly increased E-selectin release (FIG. 16B (B)). In contrast, both 3'3'-cGAMP and LPS upregulated the release of P-selectin and resistin (FIG. 16B (B)), and only c-di-AMP or LPS enhanced the release of GDF-15 and CXCL10 (FIG. 16B (B)). Collectively, these findings support the notion that different PAMPs might cause the release of different immune chemicals during innate immunity activation.

Figure 16A:
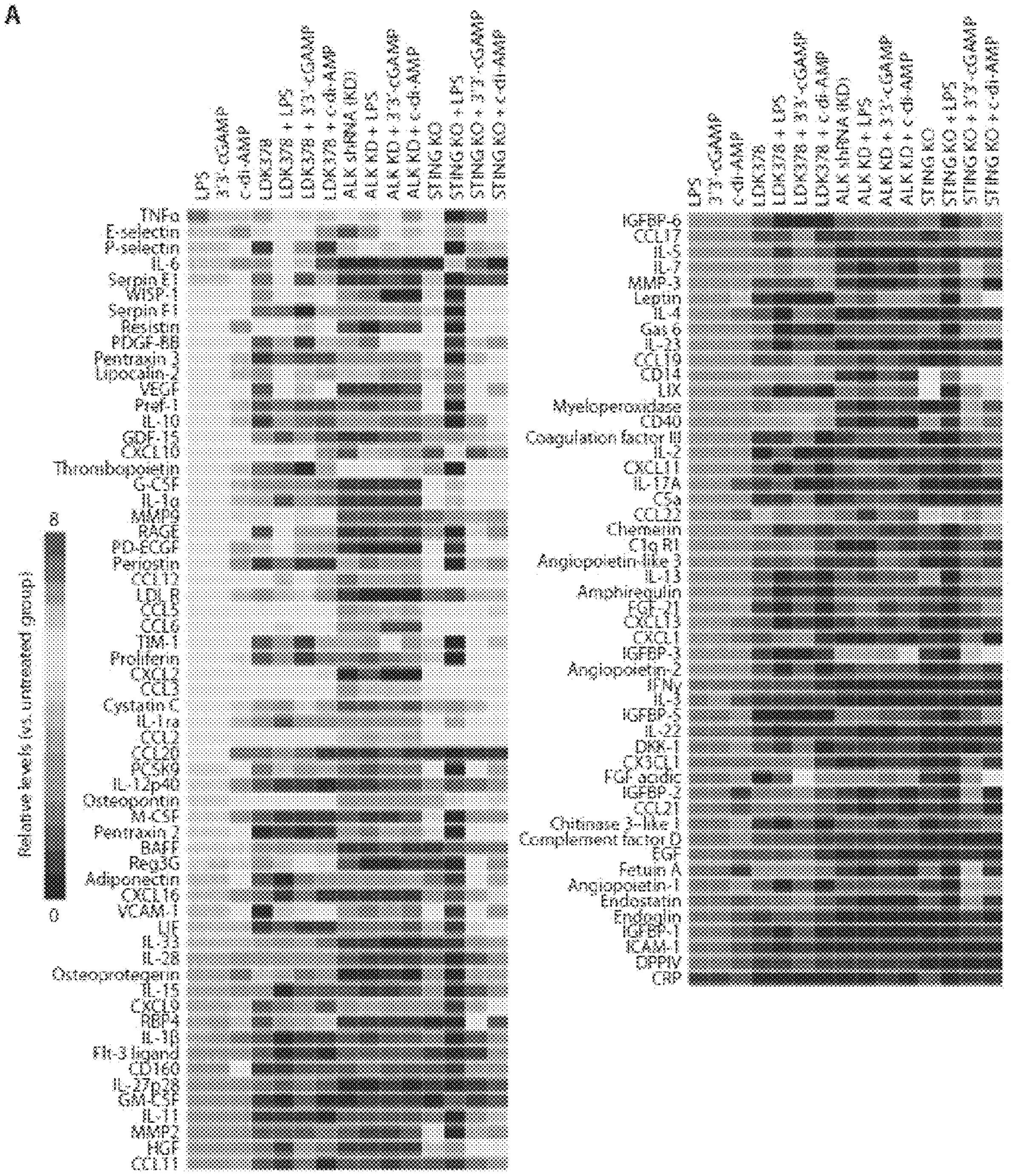
FIGS. 16A and 16B. ALK and STING have overlapping and distinct immune functions in immune chemical release. (A) Heatmap of immune chemical profile in wild-type (WT), ALK-knockdown (KD), or STING-knockout (KO) iBMDMs after stimulation with LPS (1 μg/ml), 3'3'-cGAMP (10 μg/ml), or c-di-AMP (10 μg/ml) for 16 hours with or without LDK378 (10 μM). (B) Changes in immune chemical release in WT iBMDMs after LPS, 3'3'-cGAMP, and c-di-AMP treatment. (C) Changes in immune chemical release between ALK-KD and STING-KO iBMDMs in response to 3'3'-cGAMP, c-di-AMP, or LPS.
Figure 16B:
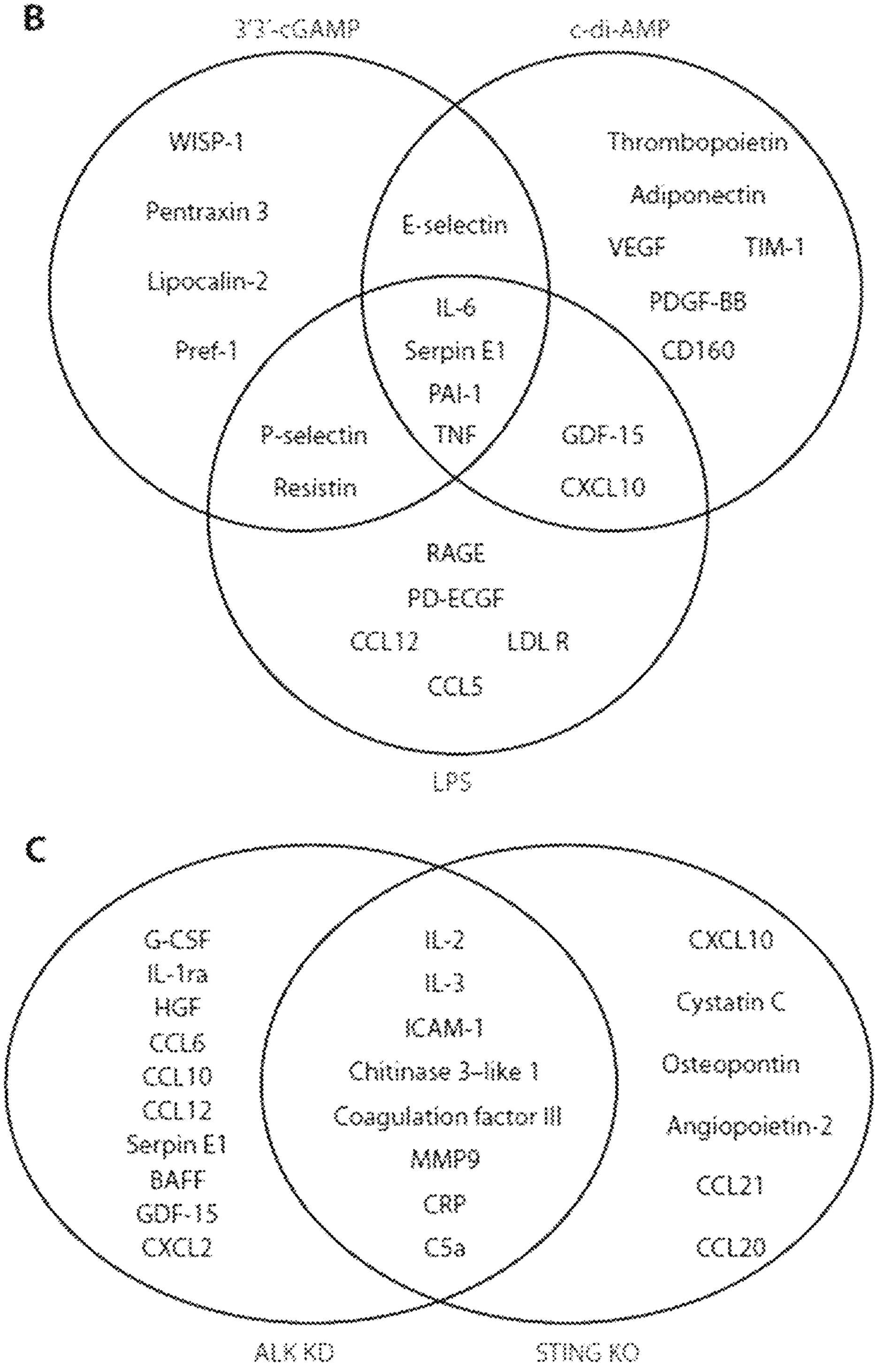
Figure 17:
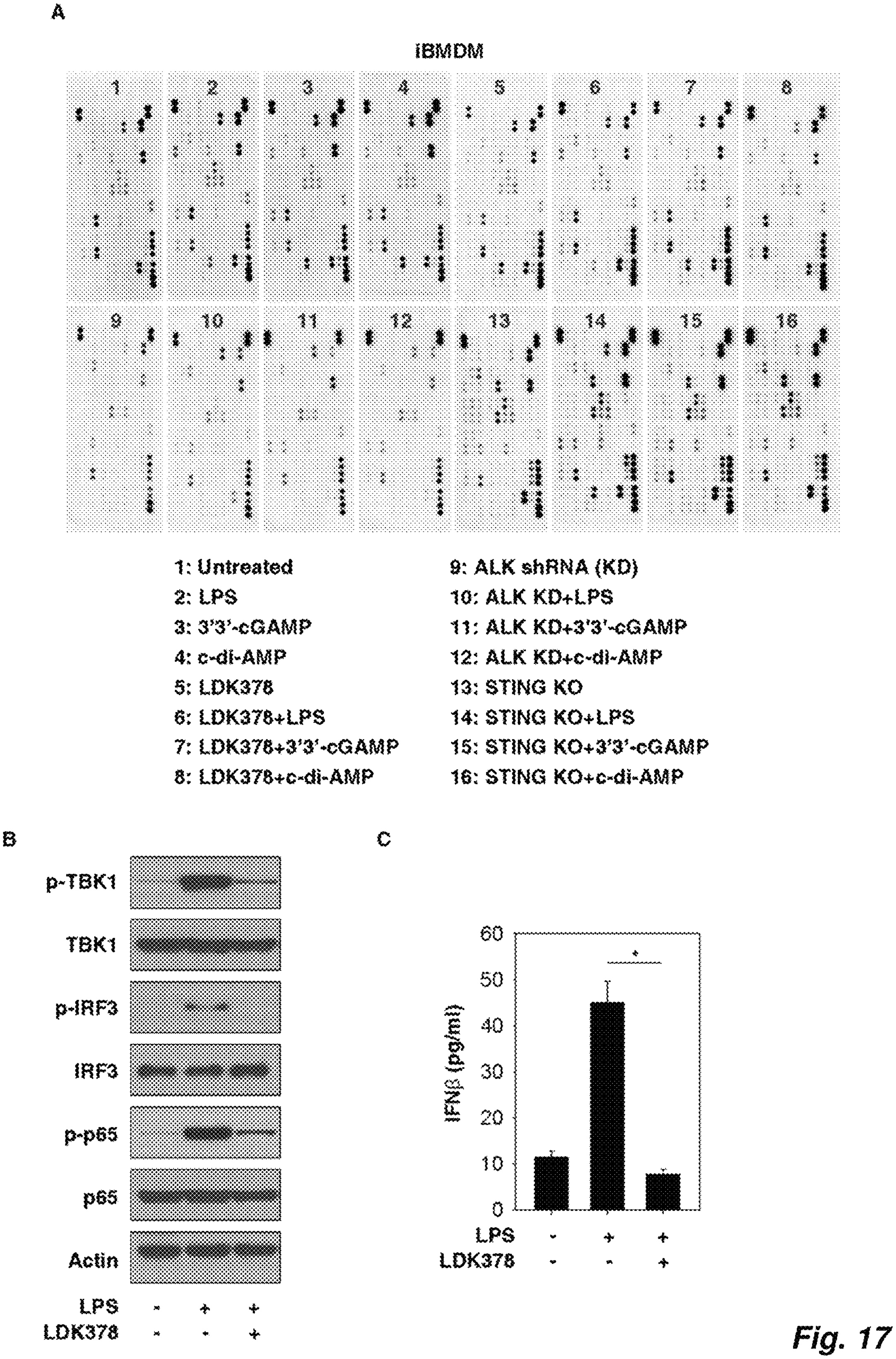
FIG. 17. ALK mediates LPS-induced macrophage activation. (A) Proteome Profiler Antibody Arrays analysis of immune chemical release in wild-type (WT), ALK-knockdown (KD), or STING-knockout (KO) iBMDMs following stimulation with LPS (1 μg/ml), 3'3'-cGAMP (10 μg/ml), or c-di-AMP (10 μg/ml) for 16 hours with or without LDK378 (10 μM). (B, C) iBMDMs were treated with LPS (1 μg/ml) in the absence or presence of LDK378 (10 μM) for three hours. Indicated protein expression (B) and IFNβ release (C) were assayed (n=3, data expressed as means±SD, $^*P<0.05$, t test).

Given that signal transduction elements interact through complex biochemically-related networks, we next sought to identify the overlapping and distinct immune effects of ALK and STING on immune chemical release in response to 3'3'-cGAMP, c-di-AMP, or LPS (FIGS. 16A (A) and 16B (B) and FIG. 17A). The knockdown of ALK and STING impaired the release of CRP, IL-2, IL-3, C5a, ICAM1, coagulation factor III, chitinase 3-like1, and MMP9 (FIG. 16B (C)). Of note, most of these ALT- and STING-related common immune chemicals play important roles in mediating sepsis-associated disseminated intravascular coagulation and thromboembolic disease. Additionally, the expression profiling assays also revealed that ALK and STING occupied distinct roles in the regulation of most chemokines released in activated iBMDMs (FIG. 16B (C)), suggesting that other unknown signaling molecules or feedback loops may also contribute to the regulation of different chemokines. LPS also has the ability to active TBK1 to coordinate the activation of the IRF3 and NF-κB pathway in immune cells (40, 41). LDK378 also inhibited the LPS-induced phosphorylation of TBK1, IRF3, and p65 (FIG. 17 (B)) as well as IFNβ release (FIG. 17 (C)) in iBMDMs. These findings indicate that ALK contributes to LPS-induced activation of the TBK1-IRF3-NF-κB pathway in macrophages.

Figure 18A:
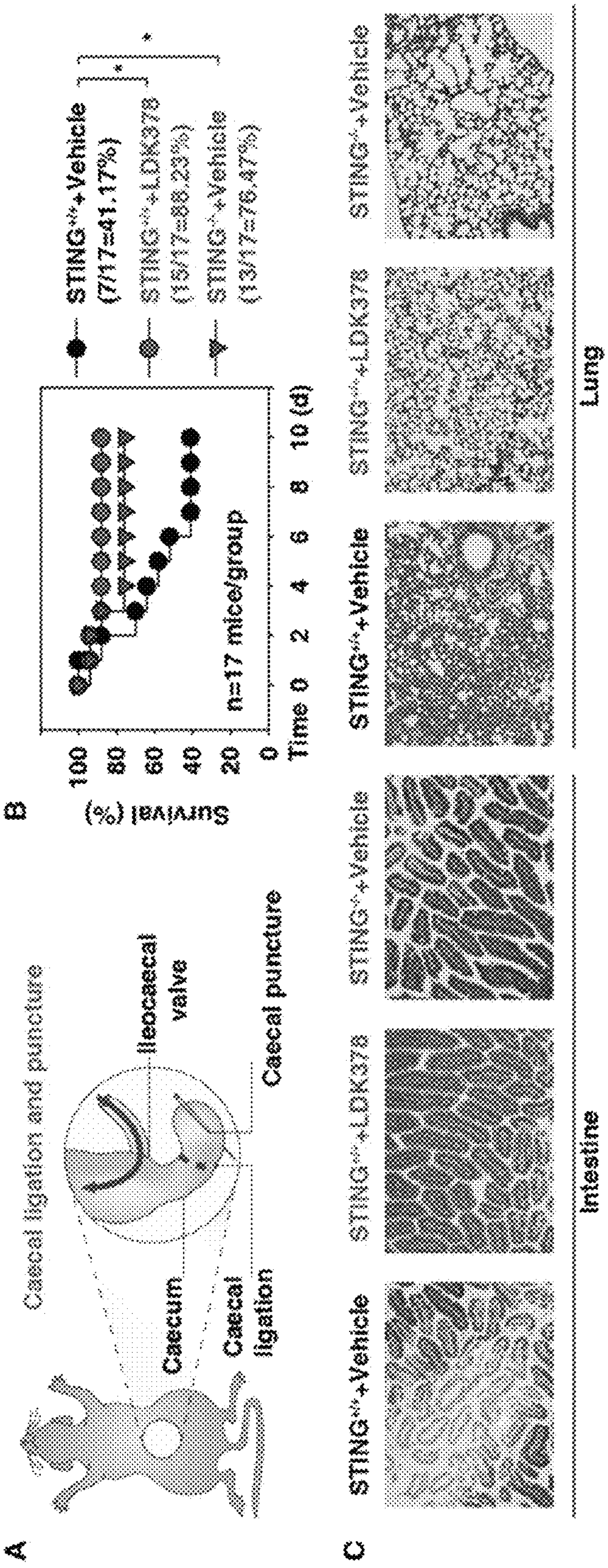
FIGS. 18A-18C. Inhibition of the ALK-STING pathway protects mice against CLP-induced polymicrobial sepsis. (A) Schematic depiction of the CLP model. (B) Administration of LDK378 or depletion of STING in mice prevented CLP (22-gauge needle)-induced animal death (n=17 mice/group; *, $P<0.05$, Kaplan-Meier survival analysis). (C-G) In parallel, tissue hematoxylin and eosin staining (day 3, bar=200 μM) (C), serum enzyme activity (day 2-7) (D), cytokine mRNA (day 3) (E), serum antibody array (day 3) (F) and heatmap of immune chemical profile (day 3) (G) were assayed (n=3 to five mice/group; *, $P<0.05$, each bar represents the mean of the data, ANOVA LSD test). The top five downregulated circulating immune chemical mediators in LDK378 and $STING^{-/-}$ groups compared with control group included IL-10, serpin E1, serpin F1, TIM-1, and CXCL2. High resolution images related to panels C, F, and G are shown in FIGS. 19 and 21.
Figure 18B:
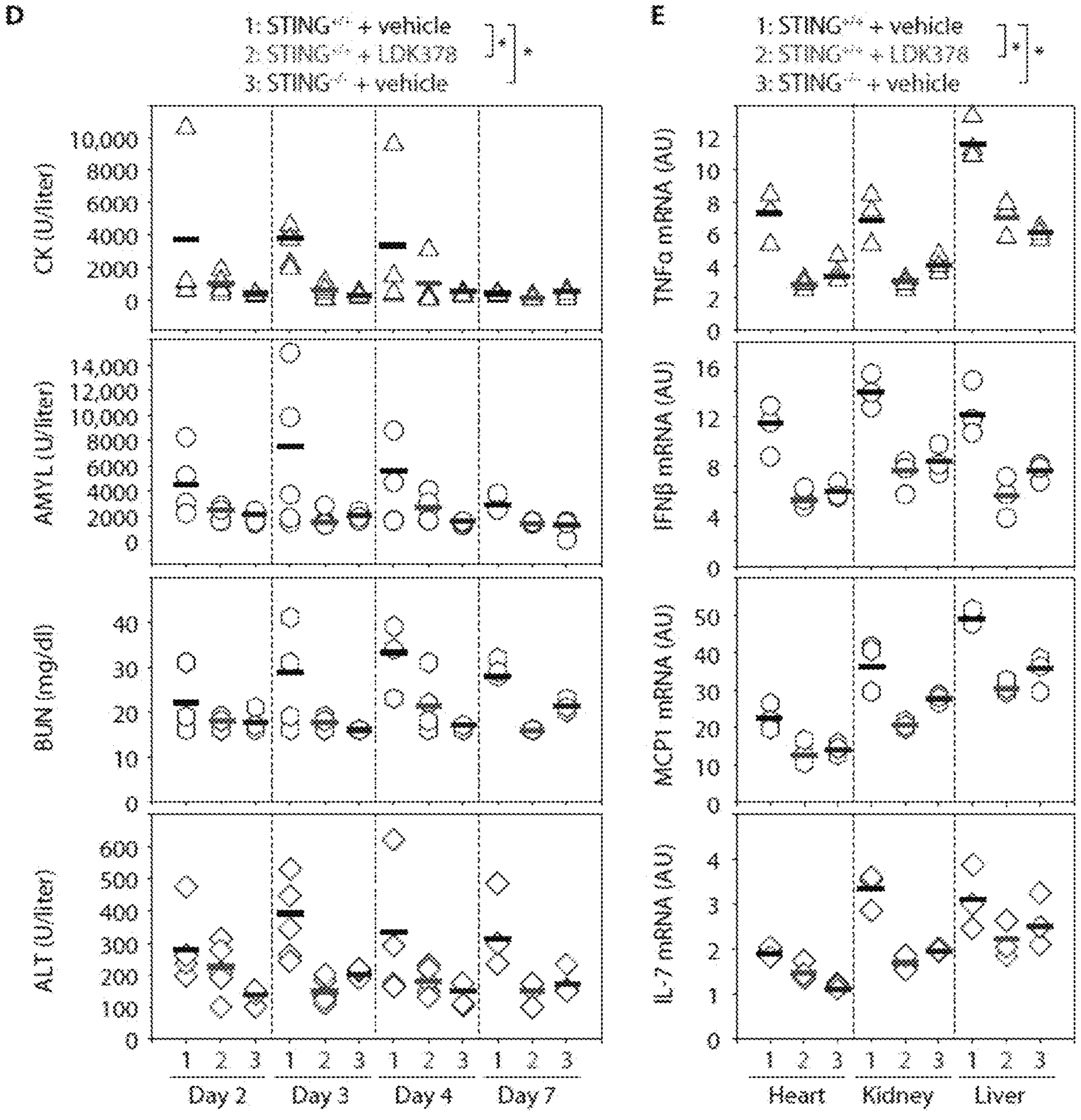
Figure 18C:
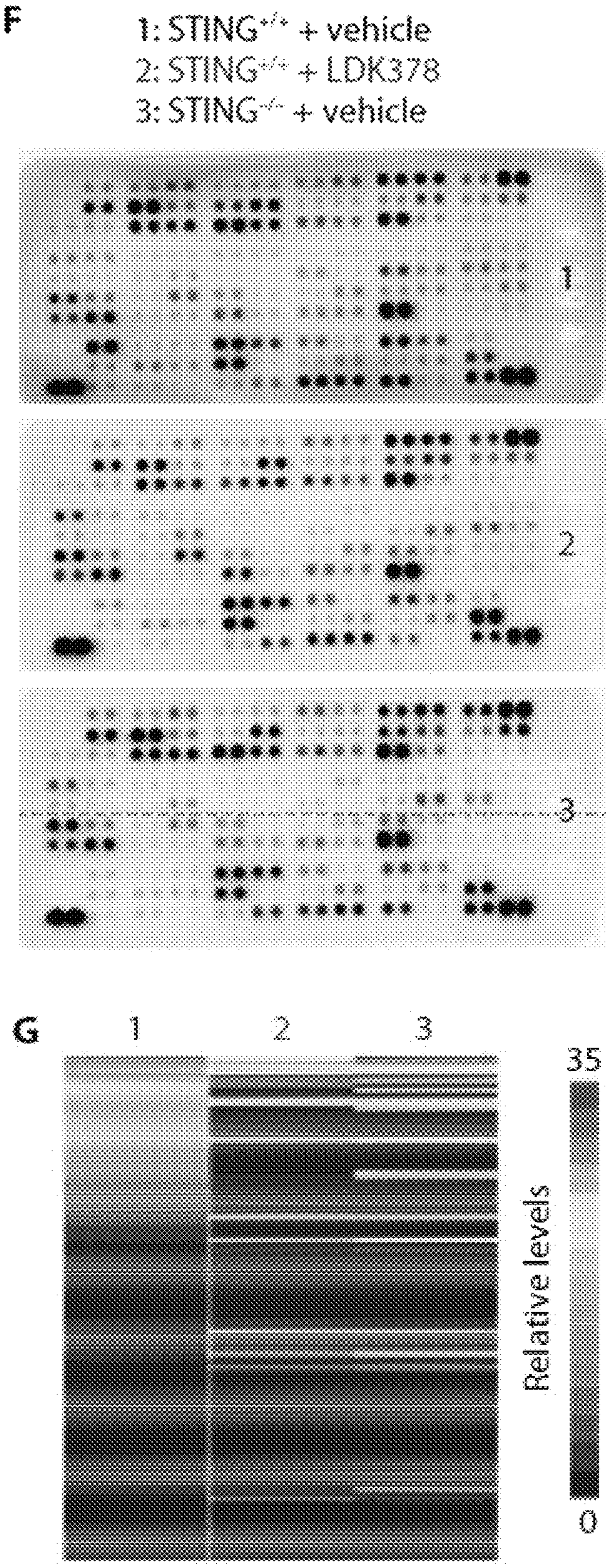
Figure 19:
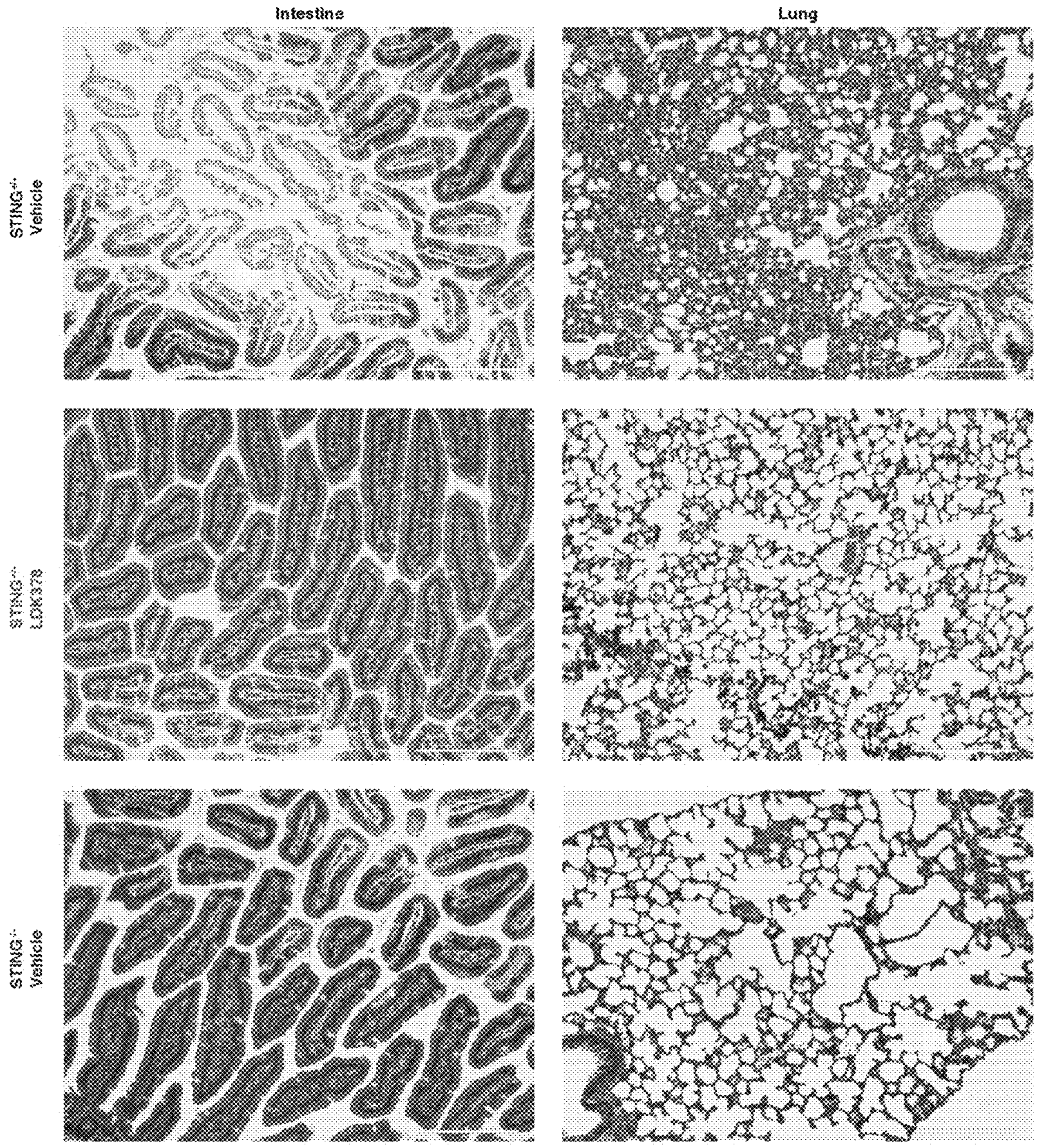
FIG. 19. Histological analysis of tissue injury in CLP-treated mice. Administration of LDK378 or depletion of STING in mice prevented CLP (22-gauge needle)-induced tissue injury at day 3 by H&E staining analysis (bar=200 μM). Related to FIG. 18C.
Figure 20A:
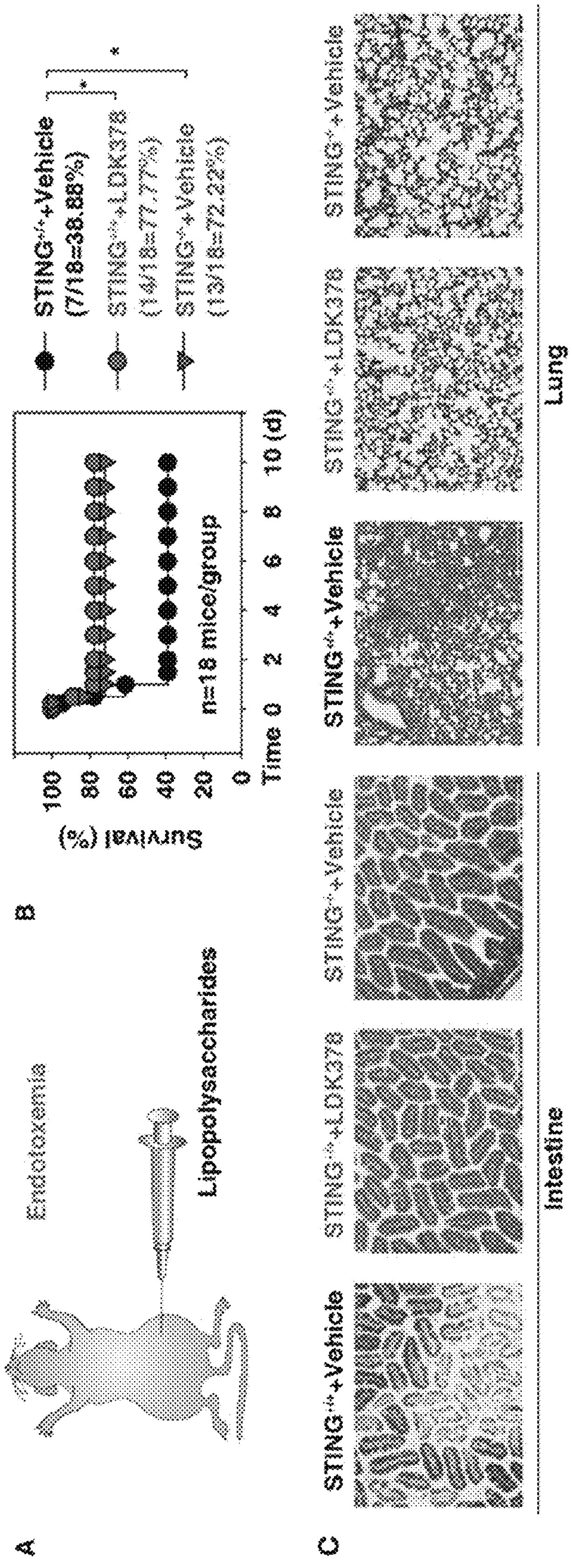
FIGS. 20A-20C. Inhibition of the ALK-STING pathway protects mice against LPS-induced endotoxemia. (A) Schematic depicting the endotoxemia model. (B) Administration of LDK378 or depletion of STING in mice prevented LPS (10 mg/kg)-induced animal death (n=18 mice/group; *, $P<0.05$, Kaplan-Meier survival analysis). (C-G) In parallel, tissue hematoxylin and eosin staining (24 hours, bar=200 μM) (C), serum enzyme activity (12-48 hours) (D), cytokine mRNA (24 hours) (E), serum antibody array (24 hours) (F) and heatmap of immune chemical profile (24 hours) (G) were assayed (n=3 to five mice/group; *, $P<0.05$, each bar represents the mean of the data, ANOVA LSD test). The top five downregulated circulating immune chemical mediators in LDK378 and $STING^{-/-}$ groups compared with control group included EGF, CD14, CXCL1, endoglin, and CCL22. High resolution images related to panels C, F, and G are shown in FIGS. 22 and 23.
Figure 20B:
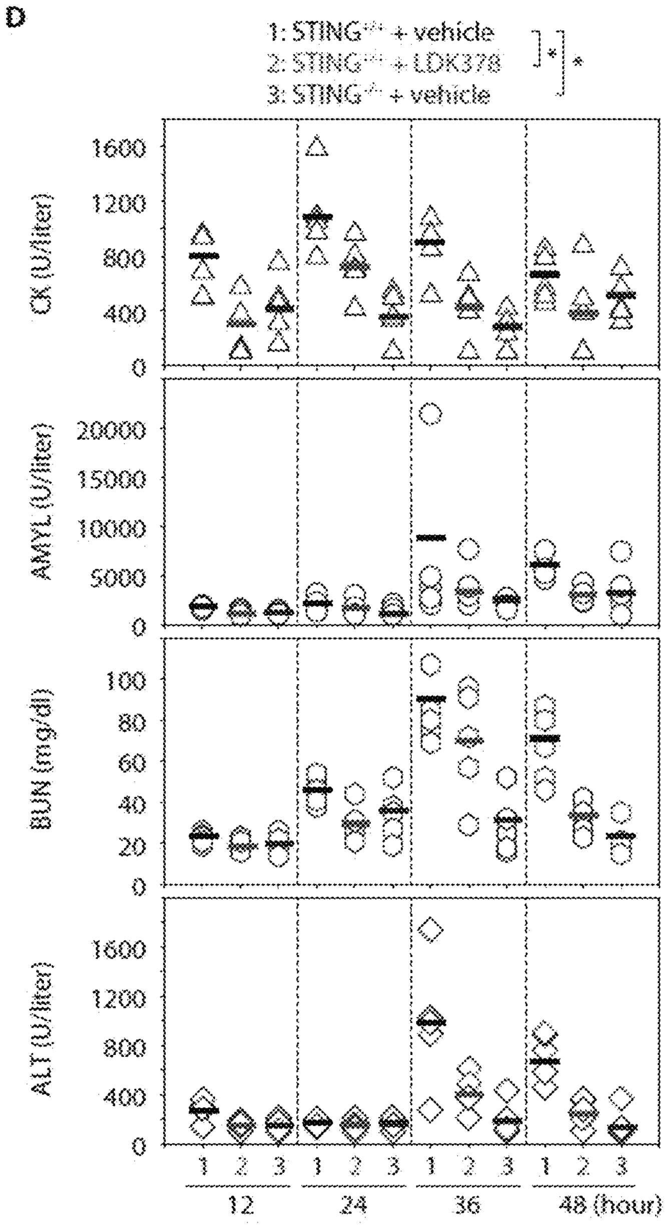
Figure 20C:
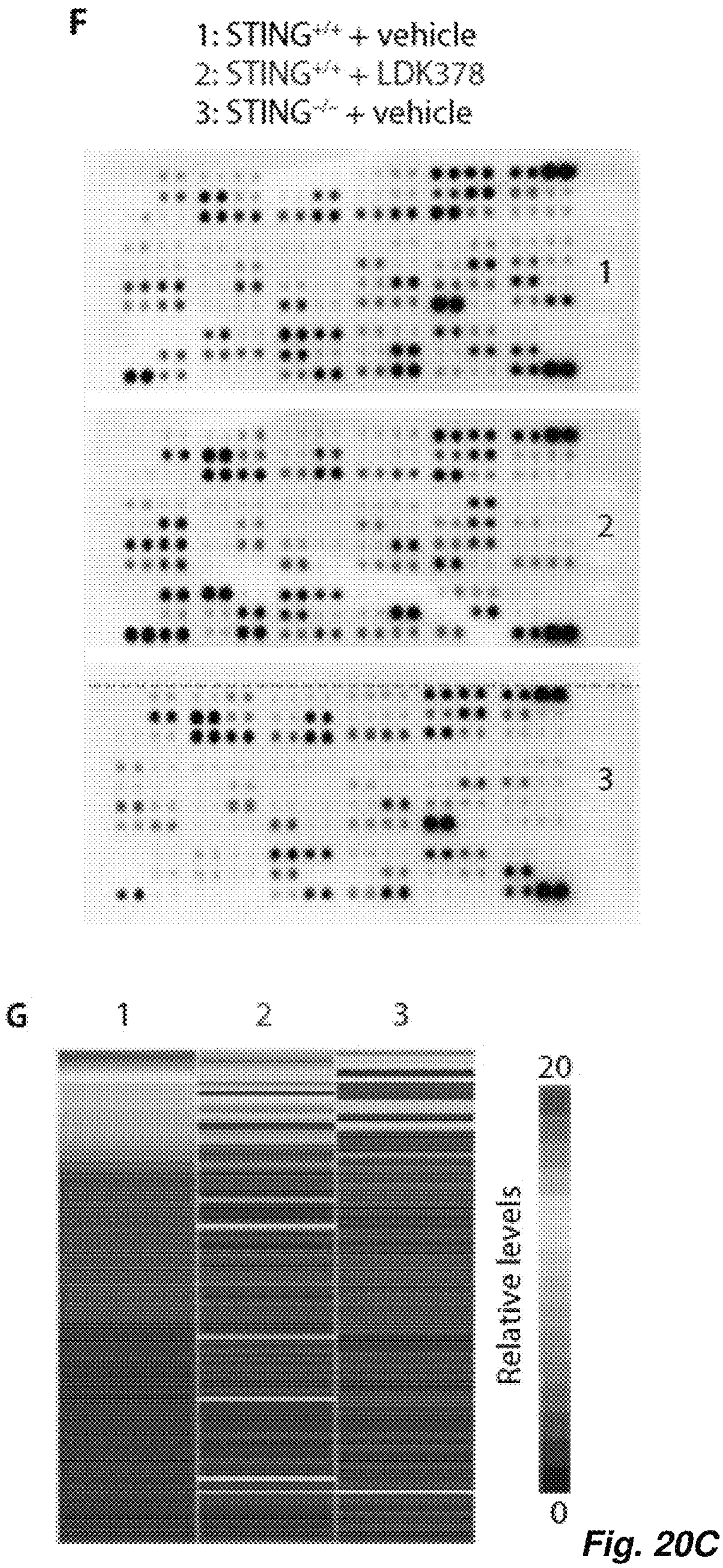
Figure 21:
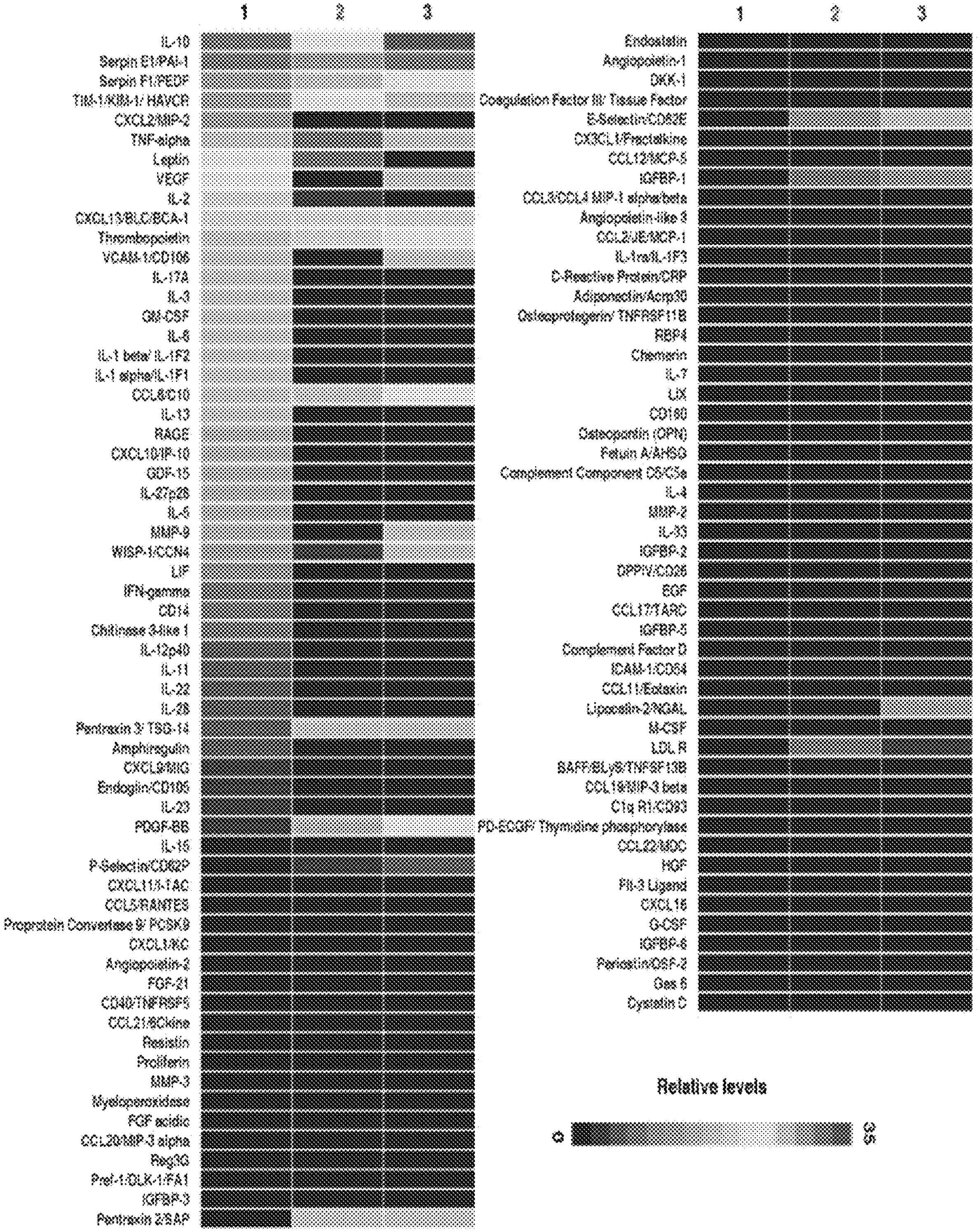
FIG. 21. Heat map of circulating immune chemicals profile in indicated mice. Proteome profiler antibody arrays analysis of serum immune chemicals concentrations in CLP (22-gauge needle)-treated indicated mice at day 3. Group 1: $STING^{+/+}$+Vehicle; Group 2: $STING^{+/+}$+LDK378; Group 3: $STING^{-/-}$+Vehicle. Related to FIGS. 18F and 18G.
Figure 22:
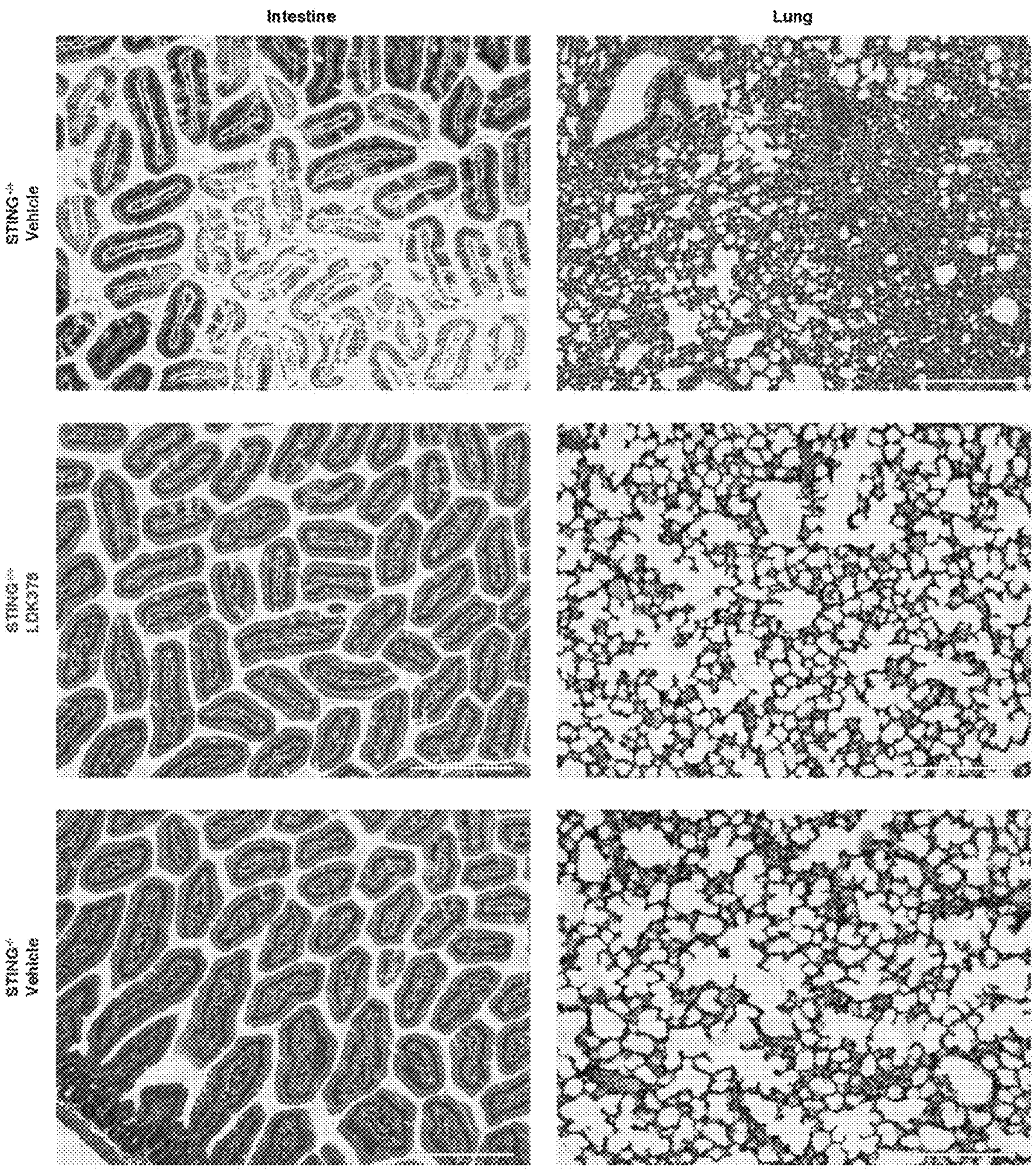
FIG. 22. Histological analysis of tissue injury in LPS-treated mice. Administration of LDK378 or depletion of STING in mice prevented LPS (10 mg/kg,)-induced tissue injury at 24 hours by H&E staining analysis (bar=200 μM). Related to FIG. 20C.
Figure 23:
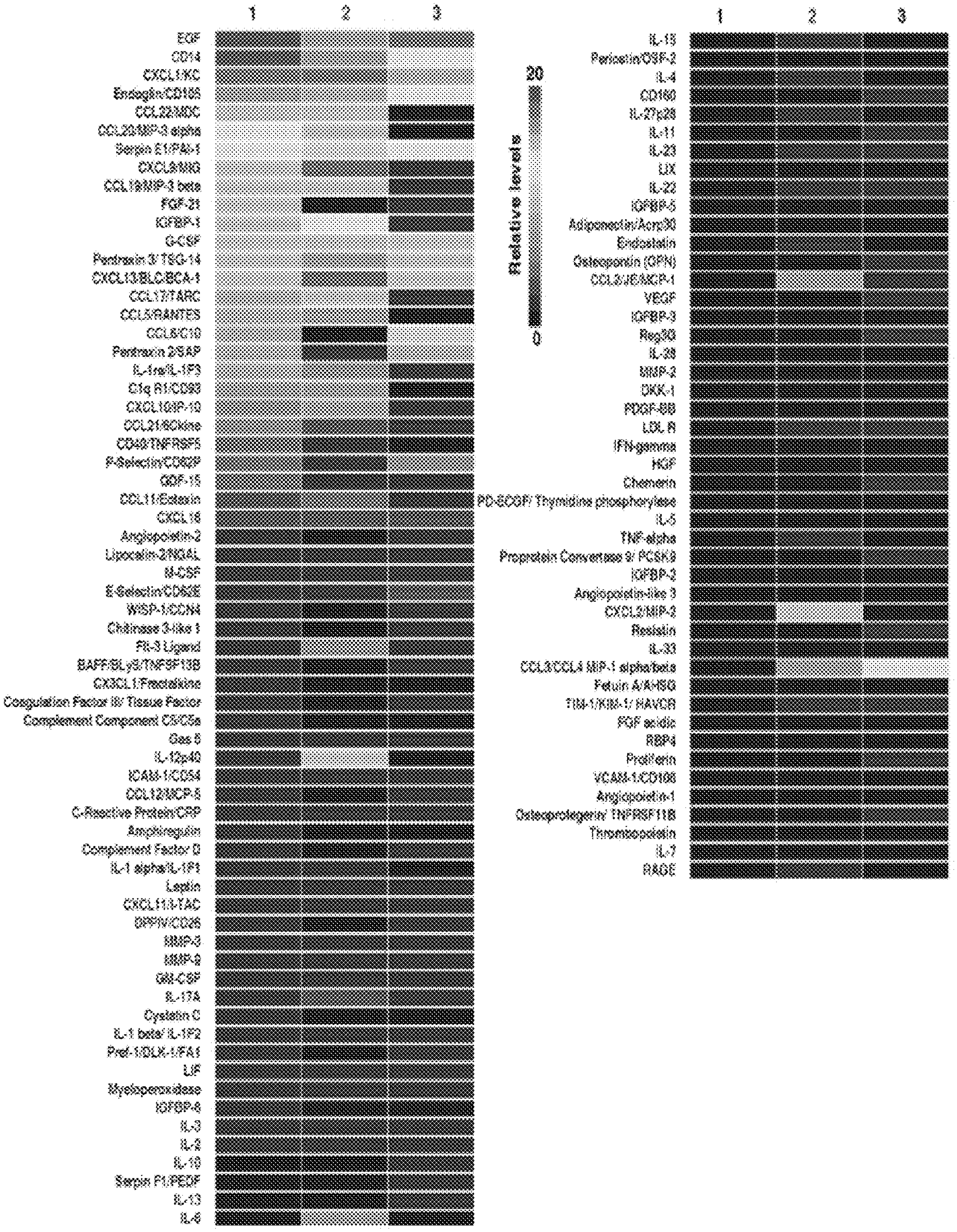
FIG. 23. Heat map of circulating immune chemicals profile in indicated mice. Proteome profiler antibody arrays analysis of serum immune chemicals concentrations in LPS (10 mg/kg)-treated indicated mice at 24 hours. Group 1: $STING^{+/+}$+Vehicle; Group 2: $STING^{+/+}$LDK378; Group 3: $STING^{-/-}$+Vehicle. Related to FIGS. 20F and 20G.

Inhibition of the ALK-STING pathway protects mice against septic death: One ultimate aim is to evaluate the therapeutic potential of ALK-STING pathway-targeting agents in sepsis and septic shock in vivo. Over the years, multiple animal models of sepsis have been developed, of which the cecal ligation and puncture (CLP) model is the most relevant to clinical sepsis. To determine the effect of the ALK inhibitor LDK378 on polymicrobial sepsis, B6 mice were subjected to CLP with 22-gauge syringe needles (FIG. 18A (A)). Repetitive administration of LDK378 (20 mg/kg, intraperitoneally (i.p.)) 2, 24, 48, and 72 hours after the onset of CLP conferred protection against lethality (FIG. 18A (B)), which was associated with reduced injury in the lung, small intestine, and other tissues (FIG. 18A (C) and FIG. 19). For instance, septic lungs showed alveolar septal wall thickening, increase in leukocyte infiltrates, and alveolar congestion and edema, whereas septic intestines exhibited signs of injury characterized by the loss of goblet cells and loss of villi (FIG. 18A (C)). These CLP-induced pathological changes were attenuated by LDK378 administration in septic mice (FIG. 18A (C)). Biochemical measurement of tissue enzymes also revealed protective effects of LDK378 against dysfunction of the heart (creatine kinase [CK]), pancreas (amylase [AMYL]), kidney (blood urea nitrogen [BUN]), and liver (alanine aminotransferase [ALT]) (FIG. 18B (D)). Moreover, LDK378 administration reduced CLP-induced TNFα, IFNβ, MCP1, and IL-7 mRNA expression (FIG. 18B (E)) and systemic release and accumulation in the serum (FIG. 18C (F, G) and FIG. 21). In an animal model of lethal endotoxemia (10 mg/kg LPS, i.p.) (FIG. 20A (A)), LDK378 promoted similar protection against endotoxemic lethality (FIG. 20A (B)), endotoxemia-induced tissue injury (FIG. 20A (C) and FIG. 22), organ dysfunction (FIG. 20B (D)), and proinflammatory cytokine expression (FIG. 20B (E)) and release (FIG. 20C (F, G) and FIG. 23). Thus, LDK378 protects mice against polymicrobial sepsis and lethal endotoxemia.

We next sought to test whether STING−/− mice are more resistant to polymicrobial sepsis and lethal endotoxemia. Like pharmacologic inhibition of ALK by LDK378, genetic STING depletion reduced animal death in both polymicrobial sepsis (FIG. 18A (B)) and lethal endotoxemia models (FIG. 20A (B)), which was associated with attenuated tissue injury such as tissue destruction, necrosis, and leukocyte infiltration (FIGS. 18A (C) and 20A (C)), organ dysfunction (FIGS. 18B (D)) and 20B (D)), and proinflammatory cytokine expression (FIGS. 18B (E) and 20B (E)) and release (FIGS. 18C (F, G) and 20C (F, G)). Collectively, these in vivo data agree with the in vitro data obtained in macrophages and monocytes and suggest that activation of the ALK-STING pathway mediates the pathophysiology of sepsis and septic shock.

Figure 24:
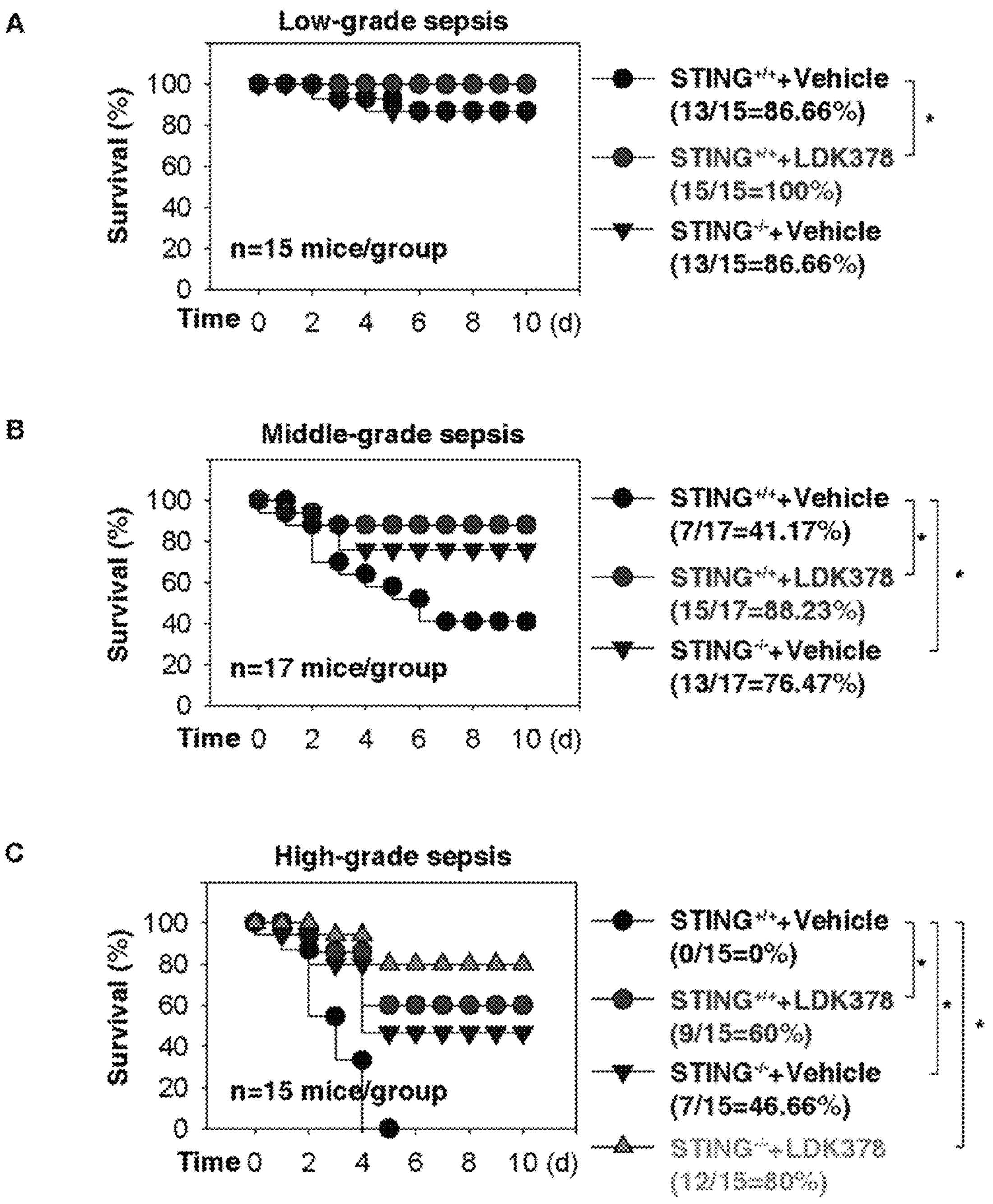
FIG. 24. Effects of targeting the ALK-STING pathway on CLP-induced septic death. Indicated B6 mice were subjected to CLP with syringe needles with gauges ranging from 27 (A, "low-grade sepsis"), 22 (B, "middle-grade sepsis"), to 17 (C, "high-grade sepsis") (n=15-17 mice/group; $P<0.05$, Kaplan-Meier survival analysis).

It is possible that the ALK-STING pathway may still be needed to instill effective innate immunity against pathogens in response to mild or sub-lethal infections. During severe or lethal infections, the dysregulated overactivation of the ALK-STING pathway may tilt the balance towards promoting overzealous inflammatory responses that may contribute to the pathogenesis of sepsis. To determine whether the ALK-STING pathway's contribution to mouse sepsis depends on severity of the disease model, B6 mice were subjected to CLP with syringe needles with gauges ranging from 17-27. Increasing the needle thickness decreased the percent survival from 86.66% (using a 27 G needle, "low-grade sepsis") to 41.17% (using a 22 G needle, "middle-grade sepsis") to 0% (using a 17 G needle, "high-grade sepsis"). Treatment with LDK378 prolonged animal survival in low-, middle-, and high-grade sepsis models (FIG. 24 (A-C)). In contrast, STING-deficient mice had prolonged survival only in high- and middle-grade sepsis models (FIG. 24 (B, C)), suggesting that the STING signaling pathway might still be needed for the host to instill an appropriate innate immunity against pathogens in response to mild and sub-lethal infections. Of note, LDK376 conferred further protection to STING-deficient mice in response to high-grade sepsis (FIG. 24 (C)), indicating that ALK and STING have both overlapping and distinct functions in septic death. Indeed, genetic or pharmacologic inhibition of ALK or STING also led to changes in the release of overlapping and distinct immune chemicals in response to CDN, LPS, or CLP in vitro or in vivo (FIGS. 16A, 16B, 18C (F), 18C (G), 20C (F), and 20C (G)).'

ALK-STING pathway is changed in human sepsis: Although the murine endotoxemia and CLP models mimic many features of human sepsis, the translation of findings and inferences from these animal sepsis models to human sepsis remains a challenge. Thus, we next determined whether the ALK-STING pathway is similarly altered in the PBMCs of patients with sepsis. Compared with a healthy control group, the mRNA expression of ALK, EGFR, STING, TBK1, and IRF3 in PBMCs was increased in the sepsis group (FIG. 25 (A, B)). Moreover, the expression of total and phosphorylated ALK, EGFR, STING, TBK1, and IRF3 proteins was also increased in the sepsis group (FIG. 25 (C)), indicating an overall activation of ALK-STING signaling pathways during human sepsis. These findings further support a potential pathogenic role of the ALK-STING pathway in human sepsis.

Discussion

Figure 26:
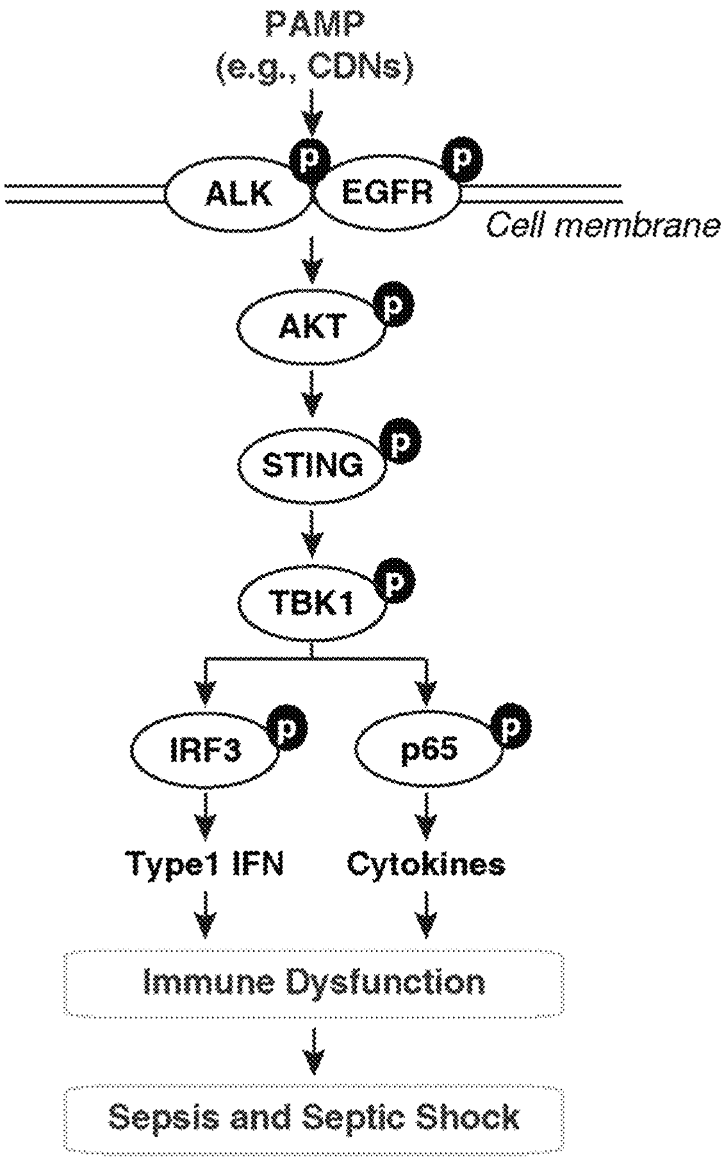
FIG. 26. Schematic depicting the pathologic role of ALK-dependent STING pathways in lethal sepsis.

The innate immune system constitutes the first line of defense against pathogen invasion. However, insufficient, excessive, or poorly-controlled activation of PRRs can cause an imbalance in the inflammation-immune network, leading to sepsis, septic shock, and ultimately death. The elucidation of this complex network can shed light on critical pathways and key molecules driving sepsis progression. We provide evidence to support ALK as a regulator of innate immune STING activation that contributes to the pathogenesis of microbial sepsis (FIG. 26). Genetic or pharmacological inhibition of the ALK-STING signaling pathway corrected excessive host response to infection and rendered mice more resistant to sepsis and septic shock, supporting the therapeutic potential of ALK inhibitors in the treatment of human sepsis.

ALK, a tyrosine kinase receptor belonging to the insulin receptor superfamily, was originally discovered as a fusion protein with nucleophosmin in anaplastic, large-cell non-Hodgkin's lymphoma in 1994. Various alterations in the ALK gene or protein have been implicated in human cancer tumorigenesis, especially in non-small-cell lung cancer (NSCLC). In cancer cells, ALK initiates several signal transduction pathways (JAK-STAT3, EGFR-AKT, and RAS-MAPK) involved in cell proliferation and transformation. In normal healthy tissues, the expression of ALK is relatively low, with the exception of the nervous system. Despite this, global knockout of ALK in mice does not cause serious behavioral phenotypes, which hinders our understanding of ALK's physiological role in mammals. Here, we demonstrated that ALK is abundantly expressed in innate immune cells (monocytes and macrophages), and instigates proinflammatory responses to PAMPs, including DNAs, during lethal infection. This may partly explain why ALK-positive cancer patients have an increased risk of developing infections.

Clinically, patients with sepsis frequently have elevated circulating DNA from invading pathogens or damaged host cells, which is often associated with poor outcomes. Although the underlying causes remain elusive, it has been suggested that the inability to efficiently eliminate DNA or abnormal DNA-sensing pathways contributes to dysregulated systemic inflammation in sepsis. Almost two decades ago, STING was suggested as a key adaptor protein for most DNA-sensing signaling pathways. This study establishes the involvement of another transmembrane tyrosine kinase, ALK, in the STING-dependent innate recognition of microbial DNA during sepsis. In septic patients, we found that the expression of ALK and STING is increased in circulating PBMCs. Thus, pharmacologically blocking the ALK-STING signaling pathway may therapeutically modulate the DNA-induced excessive inflammation response in sepsis.

Bacterial cyclic dinucleotides have long been shown to gain access to the inside of innate immune cells and directly bind cytosolic STING to initiate IRF3- and NF-κB-dependent immune responses. Host self-DNA passively released by injured cells can also enter and accumulate in the cytoplasm of innate immune cells to bind and activate STING. Here, we provide evidence for an alternative transmembrane receptor-dependent pathway, by which extracellular DNA activates STING through transmembrane ALK/EGFR-dependent mechanisms (FIG. 26). This finding supports the notion that cell-surface receptors can mediate extracellular DNA activity in inflammation and immune response. We propose that various types of STING ligands trigger ALK/EGFR interaction and activation (phosphorylation), leading to subsequent AKT phosphorylation and consequent activation of the cytosolic STING pathway. We did not observe direct interaction between ALK and STING or its downstream signaling components (TBK1, cGAS, TRIF, and FIG. 11), suggesting that ALK is likely not a direct adaptor for cytosolic STING. Phosphorylation of STING has been considered an essential and conserved mechanism of innate immune activation to both viral and bacterial infections, which now appears to depend on ALK activation.

During the last few decades, numerous phase III clinical trials of single-target therapies have failed to show efficacy in the clinical management of human sepsis. For complex systemic inflammatory syndromes, it is difficult to translate successful animal studies into clinical applications, partly because of the pitfalls in the selection of non-feasible therapeutic targets or non-realistic clinical outcome measures such as survival rates. However, the investigation of pathogenic cytokines in animal models of diseases has led to the development of successful cytokine-targeting therapeutic strategies for autoimmune diseases such as rheumatoid arthritis, such as the chimeric anti-TNF monoclonal antibody infliximab, and a soluble TNF receptor-Fc fusion protein (sTNF-R-Fc), etanercept. Here we demonstrated that LDK378, an ALK inhibitor also known as ceritinib, FDA-approved for the treatment of metastatic ALK-positive NSCLC, conferred significant protection against both lethal endotoxemia and sepsis in mice. Because LDK378 also inhibited LPS-induced phosphorylation of TBK1, IRF3, and p65 of NF-κB, and conferred further protection against both low- and high-grade sepsis, it is possible that LDK378 confers protection against lethal sepsis potentially via inhibiting both TRIF and STING pathways. With its well-defined pharmacokinetics, safety profile, and tolerability in cancer patients, it is possible and important to explore its therapeutic potential for the treatment of human sepsis.

Having described this invention above, it will be understood to those of ordinary skill in the art that the same can be performed within a wide and equivalent range of conditions, formulations and other parameters without affecting the scope of the invention or any embodiment thereof. Any document incorporated herein by reference is only done so to the extent of its technical disclosure and to the extent it is consistent with the present document and the disclosure provided herein.

The invention claimed is:

1. A method of treating systemic inflammatory response syndrome (SIRS) in a patient, comprising:

administering to the patient an amount of an anaplastic lymphoma kinase (ALK) inhibitor or an inhibitor of ALK expression effective to reduce stimulator of interferon gene (STING) activity in the patient and to thereby reduce inflammation in the patient, wherein the ALK inhibitor or the inhibitor of ALK expression is selected from the group consisting of LDK378 crizotinib, alectinib, AP26113, ASP3026, TSR-011, Toremifene Citrate, Sa1003, PAC-1, Embelin, E-64, Cryptotanshinone, Apoptosis Activator 2, AVL-292, PF-5274857; CGI1746, (-)-Parthenolide, Pifithrin μ, Bazedoxifene HCl, CP-91149, PP2, OSI-420, ZM 306416, Dalcetrapib (JTT-705 (R04607381), Wnt-059 (C59), AT101, GW0742, PNU-120596, WZ4003, NH125, Ozagrel, Daunorubicin HCl, Isotretinoin, ICG-001, Ospemifene, AZ 3146, Stattic, PRT062607 HCl, KU-60019, AZD3463, KPT-330, and a pharmaceutically acceptable salt of any of the preceding.

2. The method of claim 1, wherein the ALK inhibitor is LDK378, or a pharmaceutically acceptable salt thereof.

3. The method of claim 1, wherein the ALK inhibitor is AP26113, or a pharmaceutically acceptable salt thereof.

4. The method of claim 1, wherein SIRS is associated with an infectious disease.

5. The method of claim 1, wherein the systemic inflammatory response syndrome is sepsis, gram positive sepsis, gram negative sepsis, culture negative sepsis, fungal sepsis, neutropenic fever, or urosepsis sepsis.

6. The method of claim 1, wherein SIRS is associated with a viral disease.

7. The method of claim 6, wherein the viral disease is lung inflammation associated with influenza.

8. The method of claim 1, comprising administering to the patient and amount of an RNAi agent or an antisense agent effective to reduce a type I interferon response in a patient.

9. The method of claim 8, wherein the RNAi agent is a shRNA, such as

```
                                             (SEQ ID NO: 3)
CCGGGTGATAAATACAAGGCCCAGACTCGAGTCTGGGCCTTGTATTTATC

ACTTTTT,
or

                                             (SEQ ID NO: 4)
CCGGAGAAGAAGAAATCCG TGTGAACTCGAGTTCACACGGATTTCTTCT

TCTTTTTT.
```

10. A method of treating systemic inflammatory response syndrome (SIRS) in a patient, comprising:

administering to the patient an amount of LDK378, or a pharmaceutically acceptable salt thereof, effective to reduce stimulator of interferon gene (STING) activity in the patient and to thereby treat SIRS in the patient.

* * * * *

UNITED STATES PATENT AND TRADEMARK OFFICE

CERTIFICATE OF CORRECTION

PATENT NO. : 11,179,412 B2
APPLICATION NO. : 16/209206
DATED : November 23, 2021
INVENTOR(S) : Daolin Tang et al.

It is certified that error appears in the above-identified patent and that said Letters Patent is hereby corrected as shown below:

On the Title Page

Column 2, item (56), Other Publications, Line 24, delete “nuleic” and insert -- nucleic --

In the Claims

Column 62, Line 63, Claim 1, delete “Sa1003,” and insert -- Sal003, --

Column 62, Line 66, Claim 1, delete “Pifithrin μ,” and insert -- Pifithrin-μ, --

Column 62, Line 67, Claim 1, delete “(JTT-705 (RO4607381)” and insert
-- (JTT-705, RO4607381) --

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 24

<210> SEQ ID NO 1
<211> LENGTH: 6240
<212> TYPE: DNA
<213> ORGANISM: Homo sapiens

<400> SEQUENCE: 1

agatgcgatc cagcggctct gggggcggca gcggtggtag cagctggtac ctcccgccgc      60

ctctgttcgg agggtcgcgg ggcaccgagg tgctttccgg ccgccctctg gtcggccacc     120

caaagccgcg ggcgctgatg atgggtgagg agggggcggc aagatttcgg gcgcccctgc     180

cctgaacgcc ctcagctgct gccgccgggg ccgctccagt gcctgcgaac tctgaggagc     240

cgaggcgccg gtgagagcaa ggacgctgca aacttgcgca gcgcgggggc tgggattcac     300

gcccagaagt tcagcaggca gacagtccga agccttcccg cagcggagag atagcttgag     360
```

-continued

```
ggtgcgcaag acggcagcct ccgccctcgg ttcccgccca gaccgggcag aagagcttgg    420
aggagccaaa aggaacgcaa aaggcggcca ggacagcgtg cagcagctgg gagccgccgt    480
tctcagcctt aaaagttgca gagattggag gctgccccga gaggggacag accccagctc    540
cgactgcggg gggcaggaga ggacggtacc caactgccac ctcccttcaa ccatagtagt    600
tcctctgtac cgagcgcagc gagctacaga cgggggcgcg gcactcggcg cggagagcgg    660
gaggctcaag gtcccagcca gtgagcccag tgtgcttgag tgtctctgga ctcgcccctg    720
agcttccagg tctgtttcat ttagactcct gctcgcctcc gtgcagttgg gggaaagcaa    780
gagacttgcg cgcacgcaca gtcctctgga gatcaggtgg aaggagccgc tgggtaccaa    840
ggactgttca gagcctcttc ccatctcggg gagagcgaag ggtgaggctg ggcccggaga    900
gcagtgtaaa cggcctcctc cggcgggatg ggagccatcg ggctcctgtg gctcctgccg    960
ctgctgcttt ccacggcagc tgtgggctcc gggatgggga ccggccagcg cgcgggctcc   1020
ccagctgcgg ggccgccgct gcagccccgg gagccactca gctactcgcg cctgcagagg   1080
aagagtctgg cagttgactt cgtggtgccc tcgctcttcc gtgtctacgc ccgggaccta   1140
ctgctgccac catcctcctc ggagctgaag gctggcaggc ccgaggcccg cggctcgcta   1200
gctctggact gcgccccgct gctcaggttg ctggggccgg cgccgggggt ctcctggacc   1260
gccggttcac cagccccggc agaggcccgg acgctgtcca gggtgctgaa gggcggctcc   1320
gtgcgcaagc tccggcgtgc caagcagttg gtgctggagc tgggcgagga ggcgatcttg   1380
gagggttgcg tcgggccccc cggggaggcg gctgtggggc tgctccagtt caatctcagc   1440
gagctgttca gttggtggat tcgccaaggc gaagggcgac tgaggatccg cctgatgccc   1500
gagaagaagg cgtcggaagt gggcagagag ggaaggctgt ccgcggcaat tcgcgcctcc   1560
cagccccgcc ttctcttcca gatcttcggg actggtcata gctccttgga atcaccaaca   1620
aacatgcctt ctccttctcc tgattatttt acatggaatc tcacctggat aatgaaagac   1680
tccttccctt tcctgtctca tcgcagccga tatggtctgg agtgcagctt tgacttcccc   1740
tgtgagctgg agtattcccc tccactgcat gacctcagga accagagctg gtcctggcgc   1800
cgcatcccct ccgaggaggc ctcccagatg gacttgctgg atgggcctgg ggcagagcgt   1860
tctaaggaga tgcccagagg ctcctttctc cttctcaaca cctcagctga ctccaagcac   1920
accatcctga gtccgtggat gaggagcagc agtgagcact gcacactggc cgtctcggtg   1980
cacaggcacc tgcagccctc tggaaggtac attgcccagc tgctgcccca caacgaggct   2040
gcaagagaga tcctcctgat gcccactcca gggaagcatg gttggacagt gctccaggga   2100
agaatcgggc gtccagacaa cccatttcga gtggccctgg aatacatctc cagtggaaac   2160
cgcagcttgt ctgcagtgga cttctttgcc ctgaagaact gcagtgaagg aacatcccca   2220
ggctccaaga tggccctgca gagctccttc acttgttgga atgggacagt cctccagctt   2280
gggcaggcct gtgacttcca ccaggactgt gcccagggag aagatgagag ccagatgtgc   2340
cggaaactgc ctgtgggttt ttactgcaac tttgaagatg gcttctgtgg ctggacccaa   2400
ggcacactgt caccccacac tcctcaatgg caggtcagga ccctaaagga tgcccggttc   2460
caggaccacc aagaccatgc tctattgctc agtaccactg atgtccccgc ttctgaaagt   2520
gctacagtga ccagtgctac gtttcctgca ccgatcaaga gctctccatg tgagctccga   2580
atgtcctggc tcattcgtgg agtcttgagg ggaaacgtgt ccttggtgct agtggagaac   2640
aaaaccggga aggagcaagg caggatggtc tggcatgtcg ccgcctatga aggcttgagc   2700
ctgtggcagt ggatggtgtt gcctctcctc gatgtgtctg acaggttctg gctgcagatg   2760
```

```
gtcgcatggt ggggacaagg atccagagcc atcgtggctt ttgacaatat ctccatcagc   2820
ctggactgct acctcaccat tagcggagag gacaagatcc tgcagaatac agcacccaaa   2880
tcaagaaacc tgtttgagag aaacccaaac aaggagctga aacccgggga aaattcacca   2940
agacagaccc ccatctttga ccctacagtt cattggctgt tcaccacatg tggggccagc   3000
gggccccatg gccccaccca ggcacagtgc aacaacgcct accagaactc caacctgagc   3060
gtggaggtgg ggagcgaggg ccccctgaaa ggcatccaga tctggaaggt gccagccacc   3120
gacacctaca gcatctcggg ctacggagct gctggcggga aaggcgggaa gaacaccatg   3180
atgcggtccc acggcgtgtc tgtgctgggc atcttcaacc tggagaagga tgacatgctg   3240
tacatcctgg ttgggcagca gggagaggac gcctgcccca gtacaaacca gttaatccag   3300
aaagtctgca ttggagagaa caatgtgata gaagaagaaa tccgtgtgaa cagaagcgtg   3360
catgagtggg caggaggcgg aggaggaggg ggtggagcca cctacgtatt taagatgaag   3420
gatggagtgc cggtgcccct gatcattgca gccggaggtg gtggcagggc ctacggggcc   3480
aagacagaca cgttccaccc agagagactg gagaataact cctcggttct agggctaaac   3540
ggcaattccg gagccgcagg tggtggaggt ggctggaatg ataacacttc cttgctctgg   3600
gccggaaaat ctttgcagga gggtgccacc ggaggacatt cctgccccca ggccatgaag   3660
aagtgggggt gggagacaag agggggtttc ggagggggtg gagggggtg ctcctcaggt   3720
ggaggaggcg gaggatatat aggcggcaat gcagcctcaa acaatgaccc cgaaatggat   3780
ggggaagatg ggtttccctt catcagtcca ctgggcatcc tgtacacccc agctttaaaa   3840
gtgatggaag gccacgggga agtgaatatt aagcattatc taaactgcag tcactgtgag   3900
gtagacgaat gtcacatgga ccctgaaagc cacaaggtca tctgcttctg tgaccacggg   3960
acggtgctgg ctgaggatgg cgtctcctgc attgtgtcac ccaccccgga gccacacctg   4020
ccactctcgc tgatcctctc tgtggtgacc tctgccctcg tggccgccct ggtcctggct   4080
ttctccggca tcatgattgt gtaccgccgg aagcaccagg agctgcaagc catgcagatg   4140
gagctgcaga gccctgagta caagctgagc aagctccgca cctcgaccat catgaccgac   4200
tacaacccca actactgctt tgctggcaag acctcctcca tcagtgacct gaaggaggtg   4260
ccgcggaaaa acatcaccct cattcggggt ctgggccatg gcgcctttgg ggaggtgtat   4320
gaaggccagg tgtccggaat gcccaacgac ccaagccccc tgcaagtggc tgtgaagacg   4380
ctgcctgaag tgtgctctga acaggacgaa ctggatttcc tcatggaagc cctgatcatc   4440
agcaaattca accaccagaa cattgttcgc tgcattgggg tgagcctgca atccctgccc   4500
cggttcatcc tgctggagct catggcgggg ggagacctca agtccttcct ccgagagacc   4560
cgccctcgcc cgagccagcc ctcctccctg gccatgctgg accttctgca cgtggctcgg   4620
gacattgcct gtggctgtca gtatttggag gaaaaccact tcatccaccg agacattgct   4680
gccagaaact gcctcttgac ctgtccaggc cctggaagag tggccaagat tggagacttc   4740
gggatggccc gagacatcta cagggcgagc tactatagaa agggaggctg tgccatgctg   4800
ccagttaagt ggatgccccc agaggccttc atggaaggaa tattcacttc taaaacagac   4860
acatggtcct ttggagtgct gctatgggaa atcttttctc ttggatatat gccatacccc   4920
agcaaaagca accaggaagt tctggagttt gtcaccagtg gaggccggat ggacccaccc   4980
aagaactgcc ctgggcctgt ataccggata atgactcagt gctggcaaca tcagcctgaa   5040
gacaggccca actttgccat cattttggag aggattgaat actgcaccca ggacccggat   5100
```

-continued gtaatcaaca ccgctttgcc gatagaatat ggtccacttg tggaagagga agagaaagtg 5160
cctgtgaggc ccaaggaccc tgagggggtt cctcctctcc tggtctctca acaggcaaaa 5220
cgggaggagg agcgcagccc agctgcccca ccacctctgc ctaccacctc ctctggcaag 5280
gctgcaaaga aacccacagc tgcagagatc tctgttcgag tccctagagg gccggccgtg 5340
gaagggggac acgtgaatat ggcattctct cagtccaacc ctccttcgga gttgcacaag 5400
gtccacggat ccagaaacaa gcccaccagc ttgtggaacc caacgtacgg ctcctggttt 5460
acagagaaac ccaccaaaaa gaataatcct atagcaaaga aggagccaca cgacaggggt 5520
aacctggggc tggagggaag ctgtactgtc ccacctaacg ttgcaactgg gagacttccg 5580
ggggcctcac tgctcctaga gccctcttcg ctgactgcca atatgaagga ggtacctctg 5640
ttcaggctac gtcacttccc ttgtgggaat gtcaattacg gctaccagca acagggcttg 5700
cccttagaag ccgctactgc ccctggagct ggtcattacg aggataccat tctgaaaagc 5760
aagaatagca tgaaccagcc tgggccctga gctcggtcgc acactcactt ctcttccttg 5820
ggatccctaa gaccgtggag gagagagagg caatggctcc ttcacaaacc agagaccaaa 5880
tgtcacgttt tgttttgtgc caacctattt tgaagtacca ccaaaaaagc tgtattttga 5940
aaatgcttta gaaaggtttt gagcatgggt tcatcctatt ctttcgaaag aagaaaatat 6000
cataaaaatg agtgataaat acaaggccca gatgtggttg cataaggttt ttatgcatgt 6060
ttgttgtata cttccttatg cttctttcaa attgtgtgtg ctctgcttca atgtagtcag 6120
aattagctgc ttctatgttt catagttggg gtcatagatg tttccttgcc ttgttgatgt 6180
ggacatgagc catttgaggg gagagggaac ggaaataaag gagttatttg taatgactaa 6240

<210> SEQ ID NO 2
<211> LENGTH: 1620
<212> TYPE: PRT
<213> ORGANISM: Homo sapiens

<400> SEQUENCE: 2

Met Gly Ala Ile Gly Leu Leu Trp Leu Leu Pro Leu Leu Leu Ser Thr
1 5 10 15

Ala Ala Val Gly Ser Gly Met Gly Thr Gly Gln Arg Ala Gly Ser Pro
20 25 30

Ala Ala Gly Pro Pro Leu Gln Pro Arg Glu Pro Leu Ser Tyr Ser Arg
35 40 45

Leu Gln Arg Lys Ser Leu Ala Val Asp Phe Val Val Pro Ser Leu Phe
50 55 60

Arg Val Tyr Ala Arg Asp Leu Leu Leu Pro Pro Ser Ser Ser Glu Leu
65 70 75 80

Lys Ala Gly Arg Pro Glu Ala Arg Gly Ser Leu Ala Leu Asp Cys Ala
85 90 95

Pro Leu Leu Arg Leu Leu Gly Pro Ala Pro Gly Val Ser Trp Thr Ala
100 105 110

Gly Ser Pro Ala Pro Ala Glu Ala Arg Thr Leu Ser Arg Val Leu Lys
115 120 125

Gly Gly Ser Val Arg Lys Leu Arg Arg Ala Lys Gln Leu Val Leu Glu
130 135 140

Leu Gly Glu Glu Ala Ile Leu Glu Gly Cys Val Gly Pro Pro Gly Glu
145 150 155 160

Ala Ala Val Gly Leu Leu Gln Phe Asn Leu Ser Glu Leu Phe Ser Trp
165 170 175

-continued

```
Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
    370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
        435                 440                 445

Leu Gln Leu Gly Gln Ala Cys Asp Phe His Gln Asp Cys Ala Gln Gly
    450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
    530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
```

-continued

```
        595                 600                 605

Leu Gln Met Val Ala Trp Trp Gly Gln Gly Ser Arg Ala Ile Val Ala
    610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670

Gln Thr Pro Ile Phe Asp Pro Thr Val His Trp Leu Phe Thr Thr Cys
        675                 680                 685

Gly Ala Ser Gly Pro His Gly Pro Thr Gln Ala Gln Cys Asn Asn Ala
    690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
            740                 745                 750

Arg Ser His Gly Val Ser Val Leu Gly Ile Phe Asn Leu Glu Lys Asp
        755                 760                 765

Asp Met Leu Tyr Ile Leu Val Gly Gln Gln Gly Glu Asp Ala Cys Pro
    770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Gly Ala Thr Tyr Val Phe Lys Met Lys Asp
            820                 825                 830

Gly Val Pro Val Pro Leu Ile Ile Ala Ala Gly Gly Gly Gly Arg Ala
        835                 840                 845

Tyr Gly Ala Lys Thr Asp Thr Phe His Pro Glu Arg Leu Glu Asn Asn
    850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
                885                 890                 895

Gln Glu Gly Ala Thr Gly Gly His Ser Cys Pro Gln Ala Met Lys Lys
            900                 905                 910

Trp Gly Trp Glu Thr Arg Gly Gly Phe Gly Gly Gly Gly Gly Gly Cys
        915                 920                 925

Ser Ser Gly Gly Gly Gly Gly Gly Tyr Ile Gly Gly Asn Ala Ala Ser
    930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
                965                 970                 975

Gly Glu Val Asn Ile Lys His Tyr Leu Asn Cys Ser His Cys Glu Val
            980                 985                 990

Asp Glu Cys His Met Asp Pro Glu  Ser His Lys Val Ile  Cys Phe Cys
        995                 1000                1005

Asp His  Gly Thr Val Leu Ala  Glu Asp Gly Val Ser  Cys Ile Val
    1010                1015                1020
```

-continued

```
Ser Pro  Thr Pro Glu Pro His  Leu Pro Leu Ser Leu  Ile Leu Ser
    1025                 1030                 1035

Val Val  Thr Ser Ala Leu Val  Ala Ala Leu Val Leu  Ala Phe Ser
    1040                 1045                 1050

Gly Ile  Met Ile Val Tyr Arg  Arg Lys His Gln Glu  Leu Gln Ala
    1055                 1060                 1065

Met Gln  Met Glu Leu Gln Ser  Pro Glu Tyr Lys Leu  Ser Lys Leu
    1070                 1075                 1080

Arg Thr  Ser Thr Ile Met Thr  Asp Tyr Asn Pro Asn  Tyr Cys Phe
    1085                 1090                 1095

Ala Gly  Lys Thr Ser Ser Ile  Ser Asp Leu Lys Glu  Val Pro Arg
    1100                 1105                 1110

Lys Asn  Ile Thr Leu Ile Arg  Gly Leu Gly His Gly  Ala Phe Gly
    1115                 1120                 1125

Glu Val  Tyr Glu Gly Gln Val  Ser Gly Met Pro Asn  Asp Pro Ser
    1130                 1135                 1140

Pro Leu  Gln Val Ala Val Lys  Thr Leu Pro Glu Val  Cys Ser Glu
    1145                 1150                 1155

Gln Asp  Glu Leu Asp Phe Leu  Met Glu Ala Leu Ile  Ile Ser Lys
    1160                 1165                 1170

Phe Asn  His Gln Asn Ile Val  Arg Cys Ile Gly Val  Ser Leu Gln
    1175                 1180                 1185

Ser Leu  Pro Arg Phe Ile Leu  Leu Glu Leu Met Ala  Gly Gly Asp
    1190                 1195                 1200

Leu Lys  Ser Phe Leu Arg Glu  Thr Arg Pro Arg Pro  Ser Gln Pro
    1205                 1210                 1215

Ser Ser  Leu Ala Met Leu Asp  Leu Leu His Val Ala  Arg Asp Ile
    1220                 1225                 1230

Ala Cys  Gly Cys Gln Tyr Leu  Glu Glu Asn His Phe  Ile His Arg
    1235                 1240                 1245

Asp Ile  Ala Ala Arg Asn Cys  Leu Leu Thr Cys Pro  Gly Pro Gly
    1250                 1255                 1260

Arg Val  Ala Lys Ile Gly Asp  Phe Gly Met Ala Arg  Asp Ile Tyr
    1265                 1270                 1275

Arg Ala  Ser Tyr Tyr Arg Lys  Gly Gly Cys Ala Met  Leu Pro Val
    1280                 1285                 1290

Lys Trp  Met Pro Pro Glu Ala  Phe Met Glu Gly Ile  Phe Thr Ser
    1295                 1300                 1305

Lys Thr  Asp Thr Trp Ser Phe  Gly Val Leu Leu Trp  Glu Ile Phe
    1310                 1315                 1320

Ser Leu  Gly Tyr Met Pro Tyr  Pro Ser Lys Ser Asn  Gln Glu Val
    1325                 1330                 1335

Leu Glu  Phe Val Thr Ser Gly  Gly Arg Met Asp Pro  Pro Lys Asn
    1340                 1345                 1350

Cys Pro  Gly Pro Val Tyr Arg  Ile Met Thr Gln Cys  Trp Gln His
    1355                 1360                 1365

Gln Pro  Glu Asp Arg Pro Asn  Phe Ala Ile Ile Leu  Glu Arg Ile
    1370                 1375                 1380

Glu Tyr  Cys Thr Gln Asp Pro  Asp Val Ile Asn Thr  Ala Leu Pro
    1385                 1390                 1395

Ile Glu  Tyr Gly Pro Leu Val  Glu Glu Glu Glu Lys  Val Pro Val
    1400                 1405                 1410
```

-continued

```
Arg Pro  Lys Asp Pro Glu Gly  Val Pro Pro Leu Leu  Val Ser Gln
    1415                1420                1425

Gln Ala  Lys Arg Glu Glu Glu  Arg Ser Pro Ala Ala  Pro Pro Pro
    1430                1435                1440

Leu Pro  Thr Thr Ser Ser Gly  Lys Ala Ala Lys Lys  Pro Thr Ala
    1445                1450                1455

Ala Glu  Ile Ser Val Arg Val  Pro Arg Gly Pro Ala  Val Glu Gly
    1460                1465                1470

Gly His  Val Asn Met Ala Phe  Ser Gln Ser Asn Pro  Pro Ser Glu
    1475                1480                1485

Leu His  Lys Val His Gly Ser  Arg Asn Lys Pro Thr  Ser Leu Trp
    1490                1495                1500

Asn Pro  Thr Tyr Gly Ser Trp  Phe Thr Glu Lys Pro  Thr Lys Lys
    1505                1510                1515

Asn Asn  Pro Ile Ala Lys Lys  Glu Pro His Asp Arg  Gly Asn Leu
    1520                1525                1530

Gly Leu  Glu Gly Ser Cys Thr  Val Pro Pro Asn Val  Ala Thr Gly
    1535                1540                1545

Arg Leu  Pro Gly Ala Ser Leu  Leu Leu Glu Pro Ser  Ser Leu Thr
    1550                1555                1560

Ala Asn  Met Lys Glu Val Pro  Leu Phe Arg Leu Arg  His Phe Pro
    1565                1570                1575

Cys Gly  Asn Val Asn Tyr Gly  Tyr Gln Gln Gln Gly  Leu Pro Leu
    1580                1585                1590

Glu Ala  Ala Thr Ala Pro Gly  Ala Gly His Tyr Glu  Asp Thr Ile
    1595                1600                1605

Leu Lys  Ser Lys Asn Ser Met  Asn Gln Pro Gly Pro
    1610                1615                1620


<210> SEQ ID NO 3
<211> LENGTH: 57
<212> TYPE: DNA
<213> ORGANISM: Artificial Sequence
<220> FEATURE:
<223> OTHER INFORMATION: shRNA

<400> SEQUENCE: 3

ccgggtgata aatacaaggc ccagactcga gtctgggcct tgtatttatc acttttt        57


<210> SEQ ID NO 4
<211> LENGTH: 57
<212> TYPE: DNA
<213> ORGANISM: Artificial Sequence
<220> FEATURE:
<223> OTHER INFORMATION: shRNA

<400> SEQUENCE: 4

ccggagaaga agaaatccgt gtgaactcga gttcacacgg atttcttctt ctttttt        57


<210> SEQ ID NO 5
<211> LENGTH: 57
<212> TYPE: DNA
<213> ORGANISM: Artificial Sequence
<220> FEATURE:
<223> OTHER INFORMATION: shRNA

<400> SEQUENCE: 5

ccgggctgga agaatagcaa agattctcga gaatctttgc tattcttcca gcttttt        57
```

<210> SEQ ID NO 6
<211> LENGTH: 57
<212> TYPE: DNA
<213> ORGANISM: Artificial Sequence
<220> FEATURE:
<223> OTHER INFORMATION: shRNA

<400> SEQUENCE: 6
ccggcggagg atatataggt ggcaactcga gttgccacct atatatcctc cgtttt 57

<210> SEQ ID NO 7
<211> LENGTH: 58
<212> TYPE: DNA
<213> ORGANISM: Artificial Sequence
<220> FEATURE:
<223> OTHER INFORMATION: shRNA

<400> SEQUENCE: 7
ccgggctgga tgatagatgc tgatactcga gtatcagcat ctatcatcca gctttttg 58

<210> SEQ ID NO 8
<211> LENGTH: 58
<212> TYPE: DNA
<213> ORGANISM: Artificial Sequence
<220> FEATURE:
<223> OTHER INFORMATION: shRNA

<400> SEQUENCE: 8
ccgggcctat caagtggatg gctttctcga gaaagccatc cacttgatag gctttttg 58

<210> SEQ ID NO 9
<211> LENGTH: 59
<212> TYPE: DNA
<213> ORGANISM: Artificial Sequence
<220> FEATURE:
<223> OTHER INFORMATION: shRNA

<400> SEQUENCE: 9
ccgggcctat caagtggatg gcattctcga gaatgccatc cacttgatag gcttttttg 59

<210> SEQ ID NO 10
<211> LENGTH: 59
<212> TYPE: DNA
<213> ORGANISM: Artificial Sequence
<220> FEATURE:
<223> OTHER INFORMATION: shRNA

<400> SEQUENCE: 10
ccggccaagc tctcttgagg atcttctcga gaagatcctc aagagagctt ggtttttg 59

<210> SEQ ID NO 11
<211> LENGTH: 22
<212> TYPE: DNA
<213> ORGANISM: Artificial Sequence
<220> FEATURE:
<223> OTHER INFORMATION: PCR primer

<400> SEQUENCE: 11
gcctttgcca tccaagagat gc 22

<210> SEQ ID NO 12
<211> LENGTH: 22
<212> TYPE: DNA
<213> ORGANISM: Artificial Sequence
<220> FEATURE:
<223> OTHER INFORMATION: PCR Primer

<400> SEQUENCE: 12
acactgtctg ctggtggagt tc 22

<210> SEQ ID NO 13
<211> LENGTH: 20
<212> TYPE: DNA
<213> ORGANISM: Artificial Sequence
<220> FEATURE:
<223> OTHER INFORMATION: PCR Primer

<400> SEQUENCE: 13
aaactcatga gcagtctgca 20

<210> SEQ ID NO 14
<211> LENGTH: 22
<212> TYPE: DNA
<213> ORGANISM: Artificial Sequence
<220> FEATURE:
<223> OTHER INFORMATION: PCR Primer

<400> SEQUENCE: 14
aggagatctt cagtttcgga gg 22

<210> SEQ ID NO 15
<211> LENGTH: 22
<212> TYPE: DNA
<213> ORGANISM: Artificial Sequence
<220> FEATURE:
<223> OTHER INFORMATION: PCR Primer

<400> SEQUENCE: 15
ggtgcctatg tctcagcctc tt 22

<210> SEQ ID NO 16
<211> LENGTH: 23
<212> TYPE: DNA
<213> ORGANISM: Artificial Sequence
<220> FEATURE:
<223> OTHER INFORMATION: PCR Primer

<400> SEQUENCE: 16
gccatagaac tgatgagagg gag 23

<210> SEQ ID NO 17
<211> LENGTH: 23
<212> TYPE: DNA
<213> ORGANISM: Artificial Sequence
<220> FEATURE:
<223> OTHER INFORMATION: PCR Primer

<400> SEQUENCE: 17
caggaactga tagtaattgc ccg 23

<210> SEQ ID NO 18
<211> LENGTH: 22
<212> TYPE: DNA
<213> ORGANISM: Artificial Sequence
<220> FEATURE:
<223> OTHER INFORMATION: PCR Primer

<400> SEQUENCE: 18
cttcaacttg cgagcagcac ga 22

<210> SEQ ID NO 19
<211> LENGTH: 22

-continued

<212> TYPE: DNA
<213> ORGANISM: Artificial Sequence
<220> FEATURE:
<223> OTHER INFORMATION: PCR Primer

<400> SEQUENCE: 19
gctacaagag gatcaccagc ag 22

<210> SEQ ID NO 20
<211> LENGTH: 22
<212> TYPE: DNA
<213> ORGANISM: Artificial Sequence
<220> FEATURE:
<223> OTHER INFORMATION: PCR Primer

<400> SEQUENCE: 20
gtctggaccc attccttctt gg 22

<210> SEQ ID NO 21
<211> LENGTH: 19
<212> TYPE: DNA
<213> ORGANISM: Artificial Sequence
<220> FEATURE:
<223> OTHER INFORMATION: PCR Primer

<400> SEQUENCE: 21
ctgtccctgt atgcctctg 19

<210> SEQ ID NO 22
<211> LENGTH: 18
<212> TYPE: DNA
<213> ORGANISM: Artificial Sequence
<220> FEATURE:
<223> OTHER INFORMATION: PCR Primer

<400> SEQUENCE: 22
atgtcacgca cgatttcc 18

<210> SEQ ID NO 23
<211> LENGTH: 20
<212> TYPE: DNA
<213> ORGANISM: Artificial Sequence
<220> FEATURE:
<223> OTHER INFORMATION: PCR Primer

<400> SEQUENCE: 23
agcgagcatc ccccaaagtt 20

<210> SEQ ID NO 24
<211> LENGTH: 21
<212> TYPE: DNA
<213> ORGANISM: Artificial Sequence
<220> FEATURE:
<223> OTHER INFORMATION: PCR Primer

<400> SEQUENCE: 24
agggcacgaa ggctcatcat t 21